(12) United States Patent
Chen et al.

(10) Patent No.: US 8,771,683 B2
(45) Date of Patent: Jul. 8, 2014

(54) THERAPEUTIC APYRASE CONSTRUCTS, APYRASE AGENTS, AND PRODUCTION METHODS

(75) Inventors: Ridong Chen, Naperville, IL (US); Soon Seog Jeong, Naperville, IL (US)

(73) Assignee: APT Therapeutics, Inc., St. Louis, MO (US)

( * ) Notice: Subject to any disclaimer, the term of this patent is extended or adjusted under 35 U.S.C. 154(b) by 13 days.

(21) Appl. No.: 13/522,311

(22) PCT Filed: Jan. 13, 2011

(86) PCT No.: PCT/US2011/021187
§ 371 (c)(1),
(2), (4) Date: Oct. 1, 2012

(87) PCT Pub. No.: WO2011/088244
PCT Pub. Date: Jul. 21, 2011

(65) Prior Publication Data
US 2013/0142775 A1   Jun. 6, 2013

Related U.S. Application Data

(60) Provisional application No. 61/294,695, filed on Jan. 13, 2010.

(51) Int. Cl.
*A61K 38/46*   (2006.01)
(52) U.S. Cl.
USPC .......................................................... 424/94.6
(58) Field of Classification Search
None
See application file for complete search history.

(56) References Cited

U.S. PATENT DOCUMENTS

| 5,322,678 | A | 6/1994 | Morgan et al. | |
|---|---|---|---|---|
| 7,247,300 | B1 | 7/2007 | Chen et al. | |
| 7,390,485 | B2 | 6/2008 | Jeong et al. | |
| 2005/0060762 | A1* | 3/2005 | Bleck | 800/8 |
| 2006/0121568 | A1* | 6/2006 | Drapeau et al. | 435/69.1 |

OTHER PUBLICATIONS

Supplementary European Search Report for EP 11733394.8, mailed May 8, 2013, 5 pages.
ExPASY ProtParam tool for US 7,390,485 SEQ ID No. 76; created Jan. 22, 2003 [online] [retrieved Apr. 19, 2011].
Gaddie, "Structural Elements that Regulate Interactions between the Extracellular and Transmembrane Domains of Human Nucleoside Triphosphate Diphosphohydrolase 3," Created 2009 [online], [retrieved Apr. 20, 2011].
International Preliminary Report on Patentability for International Application No. PCT/US2011/021187, mailed May 25, 2012, 6 pages.
International Search Report and Written Opinion for International Patent Application No. PCT/US2011/021187, mailed May 6, 2011, 9 pages.
Smith et al., "Cloning, Sequencing, and Expression of a Human Brain Ecto-Apyrase Related to Both the Ecto-ATPases and CD39 Ecto-Apyrases," Biochemica et Biophysica Acta (1998) 1386:65-78.

* cited by examiner

*Primary Examiner* — Suzanne M Noakes
(74) *Attorney, Agent, or Firm* — Morrison & Foerster LLP

(57) ABSTRACT

This invention provides a new class of enhanced apyrases (EN-apyrases) with superior pharmacokinetic, pharmacodynamic, and pharmacochemical properties and which can be purified using simplified procedures. The invention further provides constructs for transforming a cell to produce these EN-apyrases. The EN-apyrase construct comprises sequences encoding a signal sequence, a linker, and a soluble apyrase. Also provided are preparations of apyrases and methods for producing apyrase in culture cells and purification thereof.

18 Claims, 13 Drawing Sheets

A    B

THERAPEUTIC APYRASE CONSTRUCTS, APYRASE AGENTS, AND PRODUCTION METHODS

CROSS-REFERENCE TO RELATED APPLICATIONS

This application is the national phase of PCT application PCT/US2011/021187 having an international filing date of 13 Jan. 2011, which claims benefit of U.S. Application No. 61/294,695 filed 13 Jan. 2010. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 532602000800SeqList.txt, date recorded: Jan. 16, 2013 size: 94,269 bytes).

TECHNICAL FIELD

The present invention relates to novel apyrases and uses thereof to treat thrombotic or inflammation-related diseases.

BACKGROUND

Apyrases (Ecto-ATP diphosphohydrolases) constitute a group of enzymes catalyzing metabolism of ATP to ADP and ADP to AMP. The first known human apyrase, CD39, was originally identified as a cell-surface protein on activated lymphocytes and endothelial cells. Both the in vitro and in vivo studies clearly indicated that CD39 represents an important apyrase in cardiovascular health by regulating levels of ADP. For example, apyrase is known to inhibit platelet aggregation by metabolizing extracellular ADP. Different from clopidogrel (Plavix) strategies that irreversibly bind to ADP receptor on the platelet, human apyrase does not damage the platelets per se or interfere with normal platelet function providing a safer approach to patients with excessive platelet activation.

Among the known human CD39 family, CD39L3 is known as an ecto-apyrase (ecto-ATPDase) with biochemical activity between CD39 (ecto-ATDP'ase) and CD39L1 (ecto-ATP'ase). Smith and Kirley (*Biochemica et Biophysica Acta* (1998) 1386:65-78) determined CD39L3 is found primarily in human brain tissue.

Specifically human CD39L3 is a 529 amino acid protein shown in SEQ ID NO:1 with a predicted molecular weight of 59132.42 Daltons. The isoelectric point of CD39L3 is 6.233. There are seven putative glycosylation sites and 13 cysteine residues. Based on SEQ ID NO:1, the N-terminal 43 residues and C-terminal 44 residues are considered to be part of a transmembrane domain. The catalytic core of the enzyme roughly resides between amino acid 44 through amino acid 238, and soluble forms of this protein and related apyrases containing these residues have been prepared and described by Chen, et al. (U.S. Pat. No. 7,247,300). Additionally, substituting a glycine for an arginine at residue 67 and/or an arginine for a threonine at residue 69 is shown to confer additional desired properties including enhanced ADP'ase activity where the residue number refers to the wild-type human CD39L3 shown as SEQ ID NO:1, as described in U.S. Pat. No. 7,390,485.

ProtParam analysis shows that both CD39L3 and CD39 are composed of about 520 amino acids with the pI of about 6.0. CD39L3 and CD39 also share similar amino acid compositions to each other and common structural motifs including about 440 amino acid residues of the extracellular ATP/ADPase portion that resides between the N- and C-terminal transmembrane regions. Although CD39L3 is found in chromosome 3 and CD39 in chromosome 10, their overall intron and exon structures are identical with 10 exons each.

Bioinformatics analysis suggests that CD39L3 is a brain specific isozyme or isoenzyme of CD39. Isozymes or isoenzymes may not have the same regulatory properties of their respective counterpart, but rather have adjusted their enzymatic properties to be optimal for the precise environment to which they are subjected. Northern blot studies showed CD39L3 is highly expressed in brain and kidney, while CD39 is expressed in placenta and spleen. The analysis suggests that expression of the isoenzyme CD39L3 in human brain complements the activity of CD39 as the key thromboregulator.

The present invention provides a new class of apyrases compounds and preparations thereof with improved therapeutic properties such as longer half-life, higher stability, or higher solubility, or higher purity. Methods of making such improved preparations at a high concentration in a form that can be readily purified to substantial homogeneity are also disclosed.

DISCLOSURE OF THE INVENTION

A new class of apyrases ("EN-apyrase", for "enhanced apyrase") has been prepared that has superior pharmacokinetic properties and that is more easily purified from culture.

It has been found that appropriate design of an expression vector wherein a nucleotide sequence encoding a soluble form of CD39L3 glycoprotein is appropriately coupled to a signal sequence and expressed in Chinese hamster ovary cells under suitable conditions, enhanced forms of a apyrase are obtained. These enhanced apyrase are characterized by a lower isoelectric point presumably due to enhanced glycosylation and sialation and also by uniform cleavage at the N-terminus thus easing purification and providing a more homogenous sample. Typically, the EN-apyrase is a soluble form of SEQ ID NO:1, including mutants at position 67 and/or 69. The soluble forms span approximately positions 49 through position 485 of SEQ ID NO:1 and the foregoing mutants. Typically, they have isoelectric points in the range of 3-4.5 and are heavily glycosylated.

Thus in one aspect, the invention is directed to an EN-apyrase, wherein the EN-apyrase is a soluble CD39L3 or a homolog thereof, has a homogeneous N-terminus and has an average isoelectric point in the range of about 3.0 to about 4.5; and/or wherein said EN-apyrase has an in vivo half-life in rabbits or pigs at least twice that of HEK sol-CD39L3-01, measured by apyrase assay.

In another aspect, the invention is directed to a nucleic acid construct comprising a nucleotide sequence encoding a signal sequence, a linker, and a soluble apyrase, wherein the linker has the sequence EVLP at its C-terminus and wherein said linker or a portion thereof may represent a sequence present in the native soluble apyrase. The invention is also directed to CHO cells containing this construct and to methods to produce EN-apyrase by culturing these cells.

In still another aspect, the invention is directed to a CHO culture system for obtaining EN-apyrase, which culture system comprises providing a medium wherein during culturing the medium maintains a glutamine concentration at about 2 mM and a pH of 7.4 and wherein the temperature of the culture is shifted from 37° C. to 34° C. at day 5 of culturing.

MODES OF CARRYING OUT THE INVENTION

Figure 1:
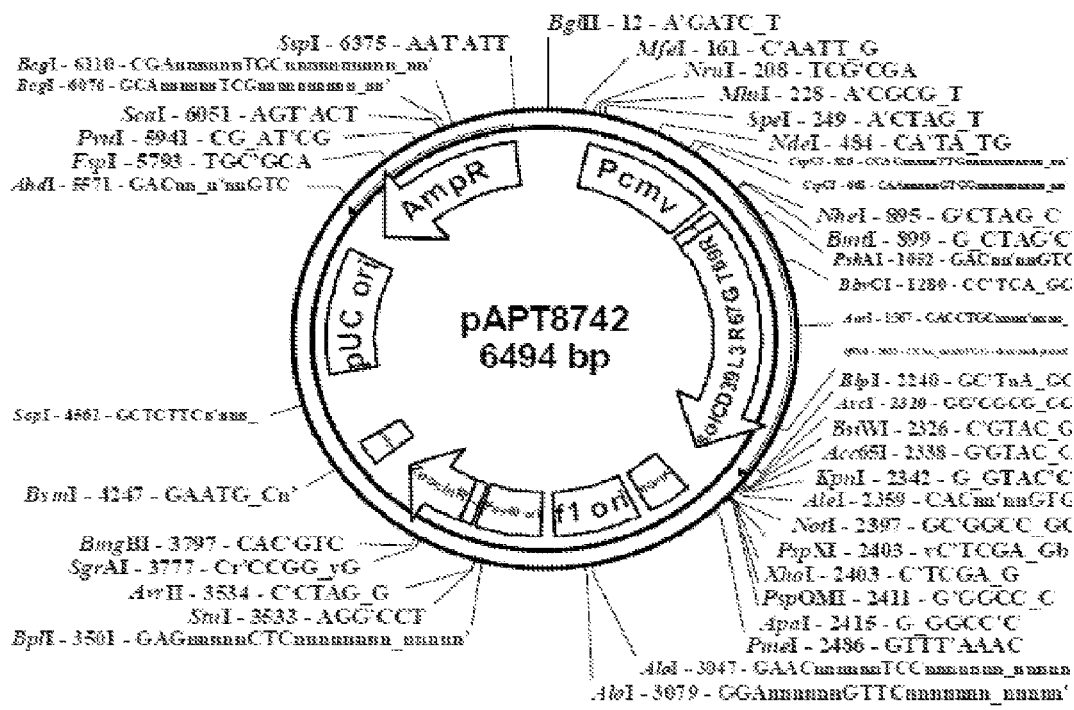
FIG. 1 is a map of pAPT8742 for expression of sol-CD39L3 R67G T69R.

Applicants have found that by employing specifically designed recombinant materials and methods, preparations of EN-apyrase can be obtained that have superior pharmacokinetic properties, putatively due to enhanced glycosylation. The resultant EN-apyrases have lower isoelectric points, homogeneous N-termini and enhanced glycosylation, as well as longer in vivo half-lives.

The EN-apyrase of the invention is a soluble CD39L3 or a homolog thereof. Soluble CD39L3 is represented by SEQ ID NO:1, absent at least about 43 amino acids from the N-terminus and at least about 44 amino acids from the C-terminus corresponding to the membrane spanning domains. The apyrase may be a soluble CD39L3 or an ADPase enhanced apyrase as taught by Jeong, et al. (U.S. Pat. No. 7,390,485), i.e., which contains a substitution of an arginine for a glycine at residue 67 and/or a threonine for an arginine at residue 69 (where the residue number refers to the CD39L3 SEQ ID NO:1).

A "homolog" of soluble CD39L3 includes sequences having 1 to 5 conservative substitutions, which retain ADP'se and ATP'ase activity and/or are of 80% or 90% or 95% identical to positions 49-485 of SEQ ID NO:1. In one embodiment, the homologs comprise tandem proline residues corresponding to residues 52 and 53 of CD39L3 SEQ ID NO:1.

Exemplary soluble CD39L3 apyrase homologs comprise amino acid residues of 49-485 of SEQ ID NO:1 with the following substitutions, referring to SEQ ID NO:1: R67G T69R; T69R; R67G; R69A T69R; R67A T69H; R67A P69K; R67G T69H; R69G T69K; T69H; T69K; and R69A. The homologs will include a portion of SEQ ID NO:1 or modifications as set forth above that include sequences beginning with the PPG residues starting at position 52.

The nucleotide sequence encoding CD39L3 is shown as SEQ ID NO:2. The amino acid sequence of soluble CD39L3 is shown in SEQ ID NO:3 and its encoding nucleotide sequence in SEQ ID NO:4. The amino acid sequence of soluble CD39L3 which is the R67G T69R mutant is shown in SEQ ID NO:5 and its coding sequence in SEQ ID NO:6. The amino acid sequence of the protein encoded by the construct used to prepare HEK-SOL-CD39L3-01, a non-enhanced form of apyrase is shown in SEQ ID NO:7 and its corresponding encoding nucleotide sequence in SEQ ID NO:8. The amino acid sequence encoded by the construct that produces one embodiment of EN-apyrase is shown in SEQ ID NO:9 and its encoding nucleotide sequence in SEQ ID NO:10.

Secretory Signal Sequence

The EN-apyrase of the invention are produced in a form that is secreted in to the medium, and thus the constructs for their production include a signal sequence.

The signal sequence of the present invention can be any signal sequence known to result in secretion of a protein in appropriate cell systems. Moreover, in silico methods exist to identify and predict sequences function as secretory signal sequences, for example as described by Otsuki, et al., *DNA Research* (2005) 12:117-126, "Signal Sequence and Keyword Trap in silico for Selection of Full-Length Human cDNAs Encoding Secretion or Membrane Proteins from Oligo-Capped cDNA Libraries."

By way of example, secretory signal sequences can be any of the sequences set forth in Table 1.

TABLE 1

Secretory Signal Sequences

| Accession Number | Entry Name | Protein Name | Organism | Length | Signal Sequence | SEQ ID NO: |
|---|---|---|---|---|---|---|
| P01892 | 1A02_HUMAN | HLA class I histocompatibility antigen, A-2 alpha chain | Homo sapiens | 24 | MAVMAPRTLVLLLSGALALT . . . | 11 |
| P23795 | ACES_BOVIN | Acetylcholinesterase | Bos taurus | 30 | MRPPWCPLHTPSLTPPLLLL . . . | 12 |
| Q9GLN7 | ACE_PANTR | Angiotensin-converting enzyme, somatic isoform | Pan troglodytes | 27 | MGAASGRRGPGLLLPLLLLL . . . | 13 |

TABLE 1-continued

Secretory Signal Sequences

| Accession Number | Entry Name | Protein Name | Organism | Length | Signal Sequence | SEQ ID NO: |
|---|---|---|---|---|---|---|
| Q28483 | ADAM5_MACFA | Disintegrin and metalloproteinase domain-containing protein 5 | Macaca fascicularis | 16 | MFLLLVLLTGLGGMHA | 14 |
| A2AJA7 | AEGP_MOUSE | Apical endosomal glycoprotein | Mus musculus | 21 | MCLPSIILLSTWVLFMAAQSL . . . | 15 |
| P00688 | AMYP_MOUSE | Pancreatic alpha-amylase | Mus musculus | 15 | MKFVLLLSLIGFCWA | 16 |
| P13205 | ANFB_RAT | Natriuretic peptides B | Rattus norvegicus | 26 | MDLQKVLPQMILLLLFLNLS . . . | 17 |
| Q5R9X1 | CADH2_PONAB | Cadherin-2 | Pongo abelii | 25 | MCRIAGALRTLLPLLAALLQ . . . | 18 |
| O54800 | CADH8_RAT | Cadherin-8 | Rattus norvegicus | 29 | MPERLAETLLDLWTPLIILW . . . | 19 |
| Q8MIT7 | CCL11_MACMU | Eotaxin | Macaca mulatta | 23 | MKVSTTLLWLLLVAAAFSPQ . . . | 20 |
| Q8HYP4 | CCL23_MACMU | C-C motif chemokine 23 | Macaca mulatta | 21 | MKVSVAALSCLMLVTALGSQ . . . | 21 |
| P28325 | CYTD_HUMAN | Cystatin-D | Homo sapiens | 20 | MMWPMHTPLLLLTALMVAVA | 22 |

Linker Moiety

It has been found that by providing a sequence at a desired N-terminus of an apyrase having the sequence EVLP (positions 20-23 of SEQ ID NO:24), cleavage may be effected in Chinese Hamster Ovary (CHO) cells such that a uniform N-terminus is produced immediately upstream of the glutamic acid residue represented by E. However, in this sequence, the glutamic acid residue may be replaced by aspartic (D) glutamine (Q) or asparagine (N). The linkages represented in these sequences are resistant to proteases in CHO cells.

It should be noted that the linker sequence may in fact be part of the apyrase sequence, as is the case in the constructs illustrated in the examples below. Thus, the EVLP sequence (positions 20-23 of SEQ ID NO:24) becomes the N-terminus of the EN-apyrase produced. This is within the amino acid sequence of the apyrase encoded by the illustrative constructs.

Regardless of the amino acid sequence of the soluble apyrase, including the linker sequence with the carboxyl terminus as described above ensures cleavage upstream of the E, D, Q or N residue when the apyrase is secreted into the culture medium. Additional sequence downstream of the signal sequence may be present upstream of the E, D, Q or N residue, including 0-10 amino acids, preferably 1-5 amino acids.

Thus, upon proper pairing with the signal sequence and linker moiety, an apyrase construct, when transformed into CHO cells, produces a translation product with a single, strong signal peptidase cleavage site, and secretes an apyrase with a homogeneous N-terminus. "Homogeneous" includes "substantially homogeneous", e.g., more than any of about 80% or 90%, 95% or 99% of the EN-apyrase molecules processed to have the same N-terminus.

The EN-apyrases comprise substantially more glycosylation than the apyrase produced by HEK cells transformed with a construct encoding SEQ ID NO:7 (i.e., HEK-sol-CD39L3-01 as described in Preparation A). EN-apyrases are produced and secreted in mammalian cell culture with a pI in a range of about 3.0 to about 4.5. Without being bound by theory, applicants believe that the N-terminal amino acid sequence modifications cause altered N-terminus endopeptidase processing, resulting in conformational changes sufficient to alter glycosylation. Moreover, a combination of conformational changes and glycosylation are responsible for the unexpected pharmacokinetic properties of EN-apyrase. The reduced isoelectric point is believed due to an increased sialic acid content in the increased glycosylation.

One of the superior, unexpected properties of the EN-apyrases of the present invention is a glycoprotein product that can readily be purified by ion exchange chromatography. As shown below, EN-apyrase can be purified to about 90% or higher in a two step ion exchange protocol.

The instant EN-apyrases have an extended circulating half-life, in comparison to HEK-sol-CD39L3-01 as shown below. EN-apyrases have a $T_{1/2}$ in rabbits or pigs of at least about 2× or at least about 4× or of at least about 5× or of at least about 8× that of HEK-sol-CD39L3-01. Such increased half-life is especially useful for therapeutic agents such as EN-apyrases that are typically administered parenterally.

Methods for Production of EN-Apyrases

The EN-apyrases of the invention may be produced in CHO cells under control of a signal sequence as set forth above, and under culture conditions that result in these enhanced properties. Optimally, these conditions include maintaining a glutamine content in the medium of about 2 mM, maintaining the pH at about 7.4 and altering the temperature from 37° C. to 34° C. after 5 days of culture. Variations in these parameters are permitted, but for optimal production of the EN-apyrases, these conditions are reliably successful. For example, the glutamine content should be maintained between about 1.5 mM and 4 mM, preferably 2-3 mM. The pH should be maintained between about 7.0 and 7.8, preferably between 7.2 and 7.6. The temperature should be lowered to between about 31° C.-36° C., preferably 33° C.-35° C. This can be done between 4 and 6 days after the start of culture.

Uses

The instant EN-apyrases are therapeutic agents useful for at least the uses of apyrases generally, CD39 compounds more specifically, and any of CD39L1-8, e.g., CD39L3 compounds. EN-apyrases are useful as anti-platelet, anti-thrombolytic agents and as anti-inflammatory and endothelial cell (EC) protective proteins. Additionally, EN-apyrases are therapeutically useful for conditions taught in U.S. provisional application 61/294,725 filed 13 Jan. 2010 entitled "Apyrase Therapy for Bleeding Conditions", incorporated by reference in its entirety. Conditions that can usefully be treated by EN-apyrases include conditions of bleeding from injury caused by mechanical or pharmacologic insult.

In some biologic conditions, EN-apyrases of the present invention serve a therapeutic role in a plurality of functions. For example, the anti-inflammation and anti-thrombosis function of EN-apyrases results in an unexpected therapeutic efficacy in various conditions.

Thrombosis also has a proinflammatory component whereby biologically functional substances are synthesized by interactions between platelets and neutrophils (In: *Inflammation: Basic principles and clinical correlates*, 3rd ed., Gallin, J. I., and Snyderman, R. (1999) pp. 77-95). Activation of platelets releases ADP as well as ATP. It has been demonstrated that extracellular ATP induces secretion of pro-inflammatory interferon-γ and IL-2 (Langston, H., et al., *J. Immunol.* (2003) 170:2962-2970). Recent studies show that CD39 on Langerhans cells modulates inflammation and immunity in the skin (Granstein, R., *Nature Medicine* (2002) 8:336-338). Therefore the ATP'ase activity of EN-apyrases and biologically active derivatives may indirectly lower inflammatory and/or immune responses at sites of vascular injury and provide a clinical benefit to patients receiving such treatment.

In adrenergic nerves, ATP and norepinephrine are stored together in vesicles, and both are released in parallel during neurotransmission. Excessive norepinephrine release is a major cause of ischemic cardiac dysfunction and reperfusion arrhythmias which can precipitate sudden cardiac death (Levi, R., and Smith, N., *J. Pharmacol Exp. Ther.* (2000) 292:825-830). Hydrolysis of ATP released by sympathetic nerve endings lead to inhibition of norepinephrine release (Sesti, C., et al., *J. Pharmacol. Exp. Ther.* (2002) 300:605-611). Hence, ATP'ase activity of EN-apyrases may provide cardioprotective effect and prevent fatal arrhythmia for patients receiving such treatment.

Certain clinical situations may require the slow and prolonged release of biologically active EN-apyrases or biological derivatives. Such situations may require the sequestrations of EN-apyrases or biological derivatives in, for example, hydrogel or other pharmaceutically acceptable polymerizable gels. Additionally, a polyethylene glycol (PEG) can be added to prolong the blood half-life to increase efficacy of a soluble EN-apyrases. In the case where EN-apyrases are used as a preventative medication, this may allow for single-bolus dose administration to maintain protective effects of EN-apyrases for longer periods. Other protein modifications to alter protein half-life include, for example, albumin conjugation, IgG fusion molecules and altering of the proteins glycosylation pattern.

It is also envisioned in the present invention that certain medical procedures or instances may require inhibition of circulating Instant apyrase activity. Such inhibitors could be, for example, pharmaceutically acceptable enzyme inhibitors (for example, ADP analogues), pharmaceutically acceptable calcium chelators, antibodies specific to Instant apyrase. Other medical procedures could also include, for example, blood transfusions or platelet transfusions. EN-apyrases and biologically active derivatives are useful in any clinical situation where the hydrolysis of ATP and/or ADP to AMP is clinically beneficent including disease states where ATP and/or ADP concentrations are abnormally high. EN-apyrases and biologically active derivatives are beneficial in clinical situations where platelets or activated platelets play an important role in disease progression, for example, tumor metastases (Bakewell, S. J., et al., *PNAS* (2003) 100:14205-14210).

The clinical and biological effectiveness of the administered EN-apyrases or biological derivative can be readily evaluated at given time intervals after administration. For example, administration of EN-apyrases or biological derivatives should promote longer bleeding times in the setting where platelet count remains unchanged. Additionally, direct measurement of blood samples for enzyme activity of EN-apyrases or metabolites will also indicate presence of the molecule in the circulating blood. Based on precise sampling of blood samples coupled with methods known in the art for assessing biochemical function of EN-apyrases the half life of the protein can be estimated. Additional clinically relevant assays for the presence of biologically active EN-apyrases or biologically active derivative may also be envisioned.

Methods for In Vitro and In Vivo Validation of Instant Apyrase Efficacy

Biochemical function of EN-apyrases may be assessed by numerous methods available to one skilled in the art. For example, ATP'ase and ADP'ase enzymatic activities of purified EN-apyrases can be determined at 37° C. in a 1 ml solution containing 8 mM CaCl2, 200 µM substrate (ATP for ATP'ase or ADP for ADP'ase), 50 mM imidazole, and 50 mM Tris, pH 7.5 (Picher, et al., *Biochem. Pharmacol.* (1988) 51:1453). The reaction can be stopped and inorganic phosphate released can be measured by addition of 0.25 ml of malachite green reagent (Baykov, et al., *Anal. Biochem.* (1988) 171:266). Based on the spectrophotometric analysis at 630 nm, one unit of ATP'ase (or ADP'se) corresponds to release of 1µ mole of inorganic phosphate/min at 37° C. Key kinetic constants for the enzyme such as K m and k cat may be obtained by fitting data into, for example, a Michaelis-Menten equation. Other assays useful for monitoring biochemical function include, but are not limited to, a radiometric assay, a HPLC assay both described by Gayle III, et al. (*J. Clin Invest.* (1998) 101:1851-1859) or a radio-TLC assay described by Marcus, A. J., et al. (*J. Clin Invest.* (1991) 88:1690-1696).

Biological function of EN-apyrases or derivatives may be assessed by ex vivo methods as well as in vivo methods. Ex vivo methods useful for monitoring the biological function of EN-apyrases and derivatives include, for example, platelet aggregation assays (Pinsky, D. J., et al., *J. Clin Invest.* (2002) 109:1031-1040; Ozaki, Y, *Sysmex J. Int.* (1998) 8:15-22).

In vivo methods useful for assessing the biological functions of EN-apyrases and derivatives include murine stroke model, measuring bleeding time, infarction volume, blood flow, neurological deficit, intracerebral hemorrhage, and mortality (Pinsky, D. J., et al., supra; Choudhri, T. F., et al., *J. Exp. Med.* (1999) 90:91-99), murine lung ischemia/reperfusion model (Fujita, T., et al., *Nature Med.* (2001) 7:598-604), baboon model of reperfused stroke (Huang, J., et al., *Stroke* (2000) 31:3054-3063), cd39−/−mice (Pinsky, D. J., et al., *J. Clin Invest.* (2002) 109:1031-1040) and Yorkshire-Hampshire Pig model (Maliszewski, C. R., et al., PCT WO00/23094 (2000)) and rabbit model (Herbertm, J-M., et al., *Thromb Haemost* (1998) 80:512-518; Fishman, J., et al., *Lab Invest* (1975) 32:339-351; Sarembock, et al., *Circulation* (1989) 80:1029-1040) of PCI. Other methods may be known to one skilled in the art for assessing the biological function of ADP'se enhanced apyrases and derivatives as a thromboregulator.

Therapeutic Compositions of EN-Apyrases

The present invention provides compositions comprising a biologically effective amount of EN-apyrase or biologically active derivative in a pharmaceutically acceptable dosage. Therapeutic composition of EN-apyrases or biologically active derivative may be administered clinically to a patient before symptoms, during symptoms, or after symptoms. After symptom administration of EN-apyrases or biologically active derivates may occur, for example, between 0 and 48 hours after the onset of stroke. Administration of EN-apyrases or biologically active derivatives to achieve therapeutic effect may be given by, for example, bolus injection, intramuscularly, subcutaneously, inhalation, continuous infusion, sustained release, or other pharmaceutically acceptable techniques. Certain clinical situations may require administration of EN-apyrases or biologically active derivatives as a single effective dose, or may be administered daily for up to a week or a much as a month or more. Ideally EN-apyrases will be administered to patients in a pharmaceutically acceptable form containing physiologically acceptable carriers, excipients or diluents. Such diluents and excipients may be comprised of neutral buffered saline solution, antioxidants (for example ascorbic acid), low molecular weight polypeptides (for example polypeptides ≤10 amino acids) amino acids, carbohydrates (for example, glucose, dextrose, sucrose, or dextrans), chelating agents such as EDTA, stabilizers (such as glutathione). Additionally, cosubstrates for the EN-apyrases or biologically active derivatives, for example, calcium (Ca 2+) may be administered at time of dosage for maximal activity of the enzyme. Such carriers and diluents are selected to be nontoxic to the patient at recommended dosages and concentrations. It is also envisioned in the present invention that EN-apyrases or biologically active derivatives may be administer with other agents that synergistically enhance the benefit of EN-apyrases or biologically active derivatives alone. For example, it is envisioned that administration of other antiplatelets or anticoagulants, such as aspirin, heparin or bivalirudin with EN-apyrases or biologically active derivative may have additional benefits such as improve reperfusion, extend therapeutic time window, prevent reocclusion, and prevent microvascular thrombosis. It is also envisioned that administration of EN-apyrases or biologically active derivatives may improve efficacy and lower the effective dosage of thrombolytics (Activase®, TNKase™, vampire bat plasminogen activator, urokinase, streptokinase, staphylokinase, and ancrod). It is still further envisioned in the present invention that operable fusion polypeptides between, for example, and ADP enhanced apyrase and thrombolytic (for example, TNKase) may provide an ideal therapeutic solution for acute myocardial infarction (AMI), percutaneous coronary intervention (PCI) and acute ischemic stroke (AIS).

Dosage requirements of EN-apyrases or biologically active derivatives may vary significantly depending on age, race, weight, height, gender, duration of treatment, methods of administration, biological activity of EN-apyrases, and severity of condition or other clinical variables. Effective dosages may be determined by a skilled physician or other skilled medical personnel.

The citations provided herein are hereby incorporated by reference for the cited subject matter.

Preparation A

Production of Sol CD39L3 in Human Kidney Cell-Derived HEK293T Cells

HEK 293T cell lines were stably transformed with a construct that provides for the expression of SEQ ID NO:7. This sequence shows soluble CD39L3 R676 T69R mutant coupled to an underlined signal sequence from mouse IgG kappa. This sequence was inserted to provide the plasmid pAPT8742 shown in FIG. 1. The secreted protein product designated here as "HEK-sol-CD39L3-01".

Transformants were adapted to serum-free suspension culture and continually split to larger flasks until a 3 L spinner was inoculated. The cells were split every 3-4 days and apyrase in conditioned medium was collected. To produce sufficient quantity of the protein for preclinical validation and determine viability of apyrase manufacturing in a commercial scale, a pilot study was carried out in 30 L bioreactors. A typical 30 L bioreactor was inoculated at $0.5 \times 10^6$ cells per mL and in 5 to 6 days HEK 293T cells grew typically over $3.5 \times 10^6$ cells per mL and produced 2-3 mg of apyrase/L. A purification process was developed involving DEAE, size exclusion and heparin affinity columns, which leads to 30% recovery yield of apyrase.

Conditioned medium harvested from the culture of HEK293T cells transformed loaded on to a DEAE column equilibrated with 10 mM Tris-HCl, pH 7.4 after the buffer exchanged to the equilibration buffer. The apyrase fraction was eluted with 10 mM Tris-HCl, pH 7.4/100 mM NaCl. After another buffer exchange to the equilibration buffer the eluted fraction was loaded on a Heparin column equilibrated with 10 mM Tris-HCL, pH 7.4. The apyrase was eluted with 10 mM Tris-HCl, pH 7.4/30 mM NaCl and concentrated using Amicon stirred cell concentrator (Millipore).

N-terminal analysis of the purified apyrase was performed by Edman degradation and showed three different N-terminal deletions. The predicted cleavage from signal would result in an N-terminal asp shown as position 21 of SEQ ID NO:7. The recovered protein was 27% N-terminal lys (position 30), 40% N-terminal glu (position 32) and 33% N-terminal val (position 33).

Example 1

Constructs for Production of an Enhanced Apyrase

An apyrase construct was designed to encode an EN-apyrase based upon sol-CD39L3 R67G T69R. The signal sequence was the bovine α-lactalbumin signal peptide. The apyrase moiety starts at residue 49 of SEQ ID NO:1, and the encoded signal—apyrase fusion is shown in SEQ ID NO:9.

The sequence of the EN-apyrase construct inserted in the final expression retrovector plasmid is shown in Table 2 below. This construct was inserted into a retroviral vector and is designated "APT" in the resulting vector shown in FIG. 2.

Figure 2:
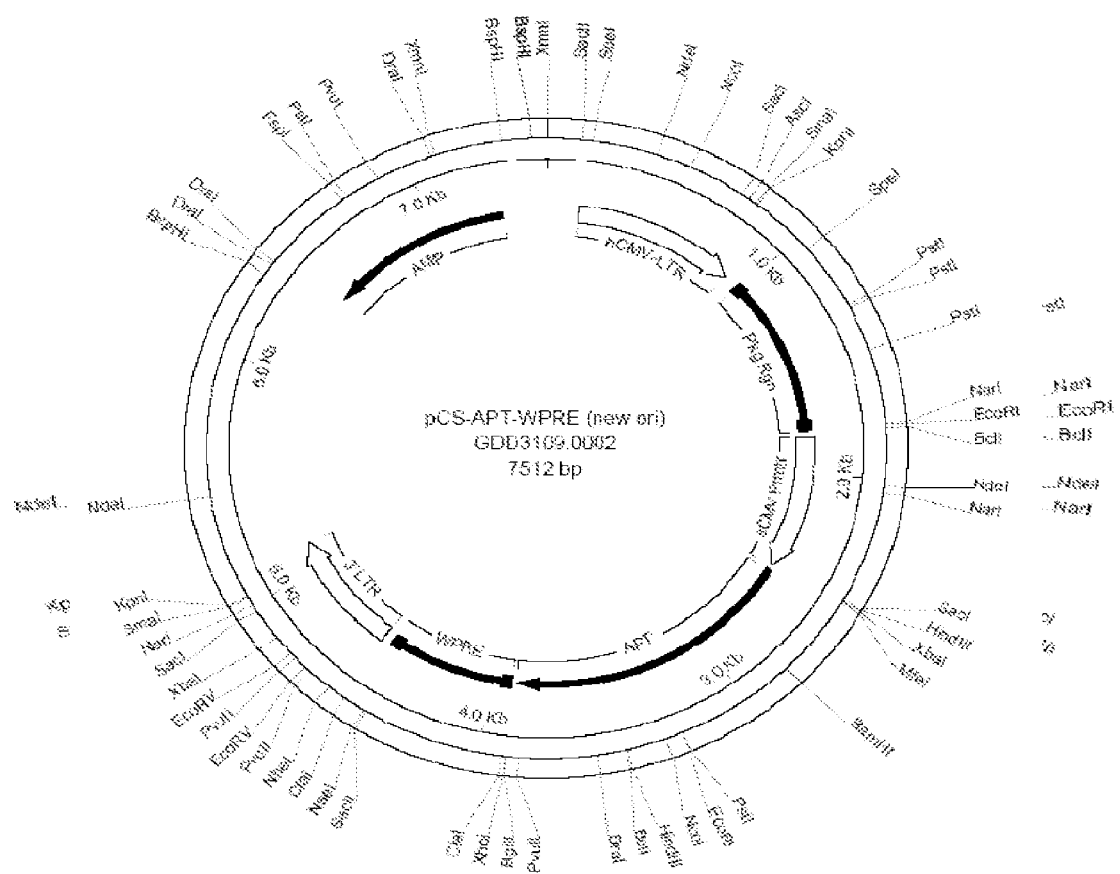
FIG. 2 depicts the expression retrovector construct pCS-APT-WPRE (new ori).
Figure 3:
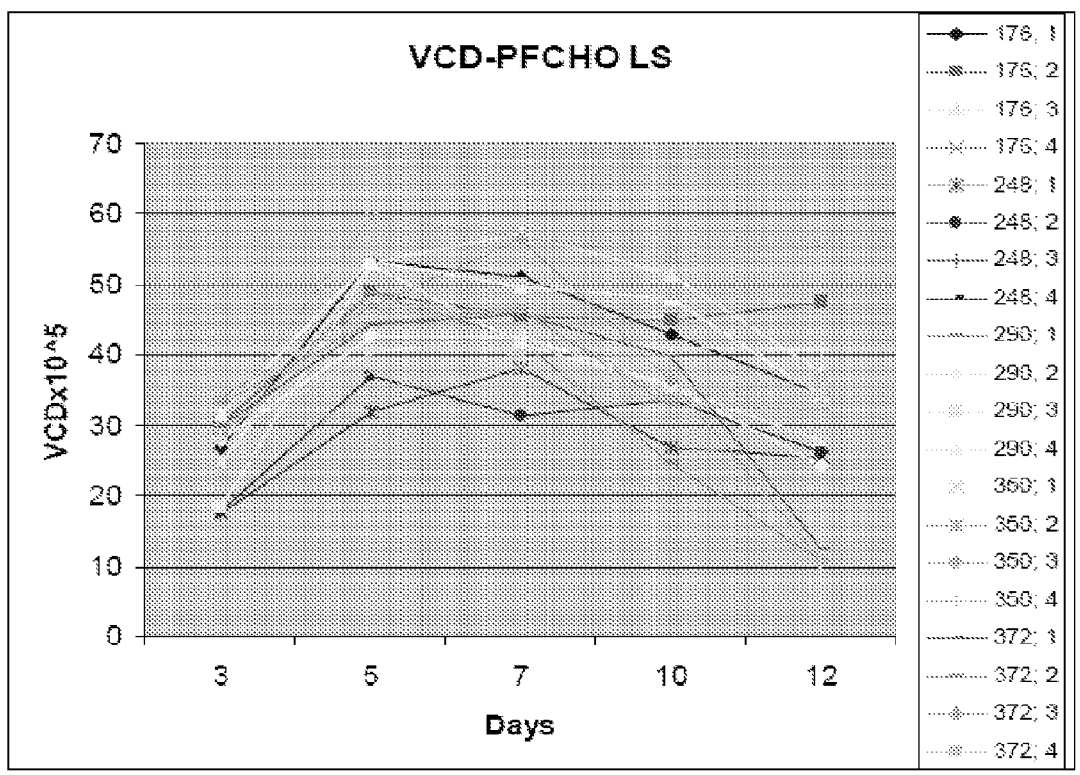
FIG. 3 depicts viable cell density in PFCHO LS medium of various apyrase-producing clones.
Figure 4:
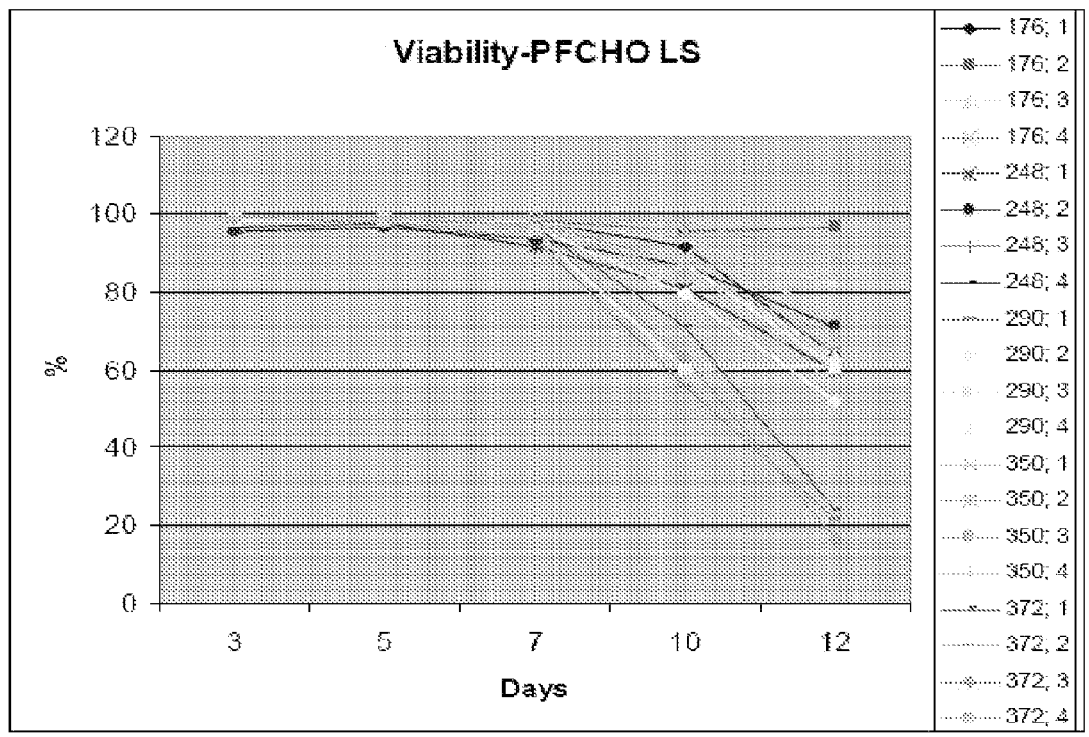
FIG. 4 depicts cell viability in PFCHO LS medium of various apyrase-producing clones.
Figure 5:
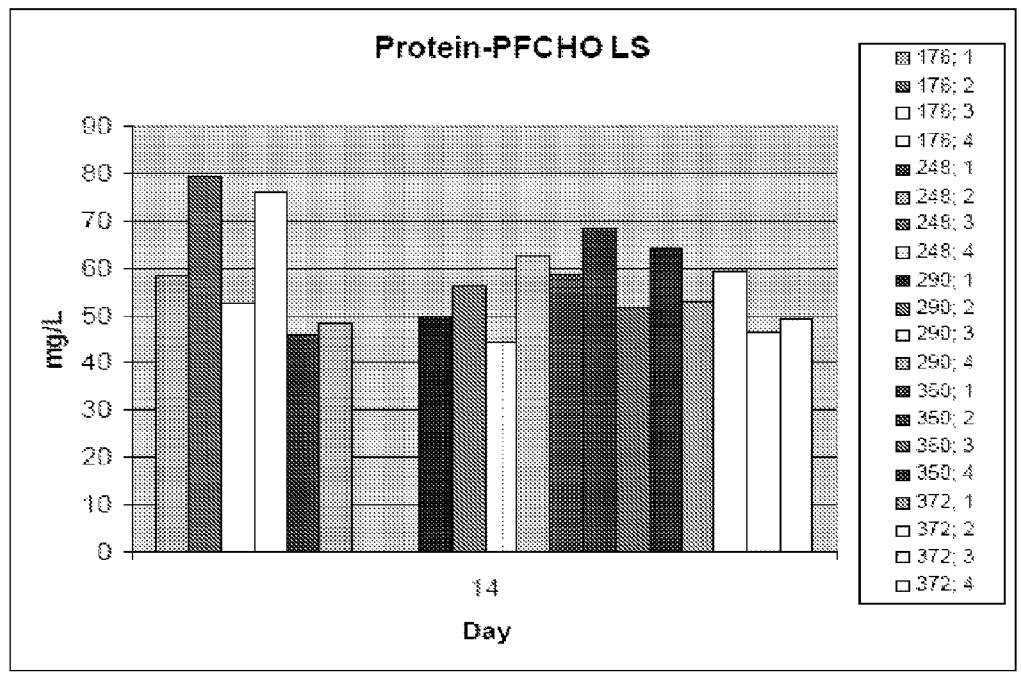
FIG. 5 depicts expression levels in PFCHO LS medium of various apyrase-producing clones.
Figure 6:
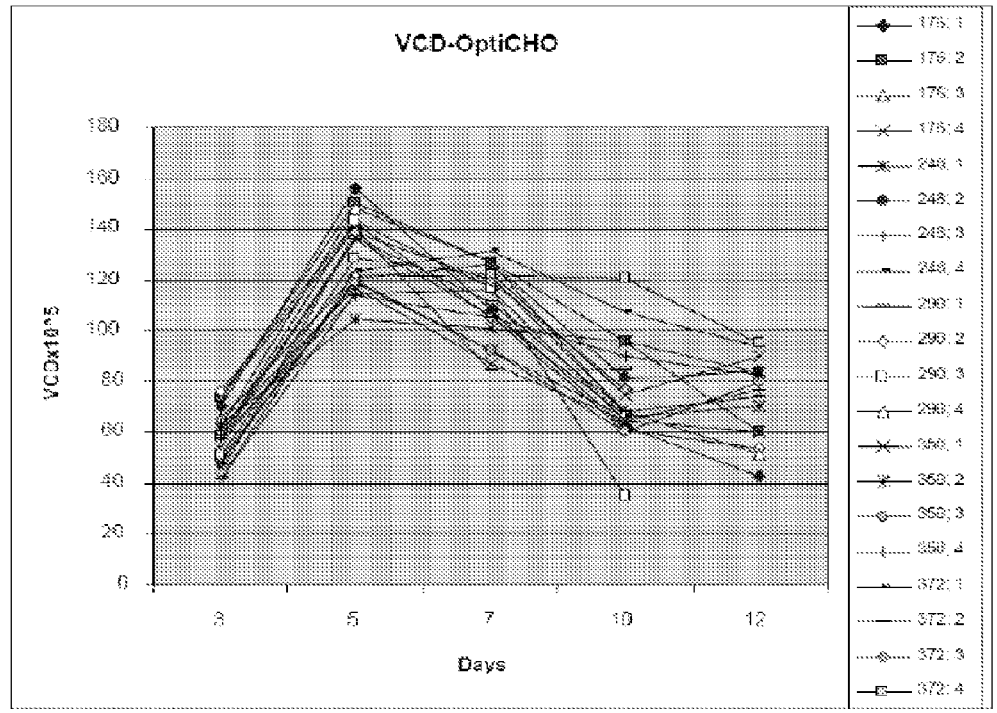
FIG. 6 depicts viable cell density in OptiCHO™ medium of various apyrase-producing clones.
Figure 7:
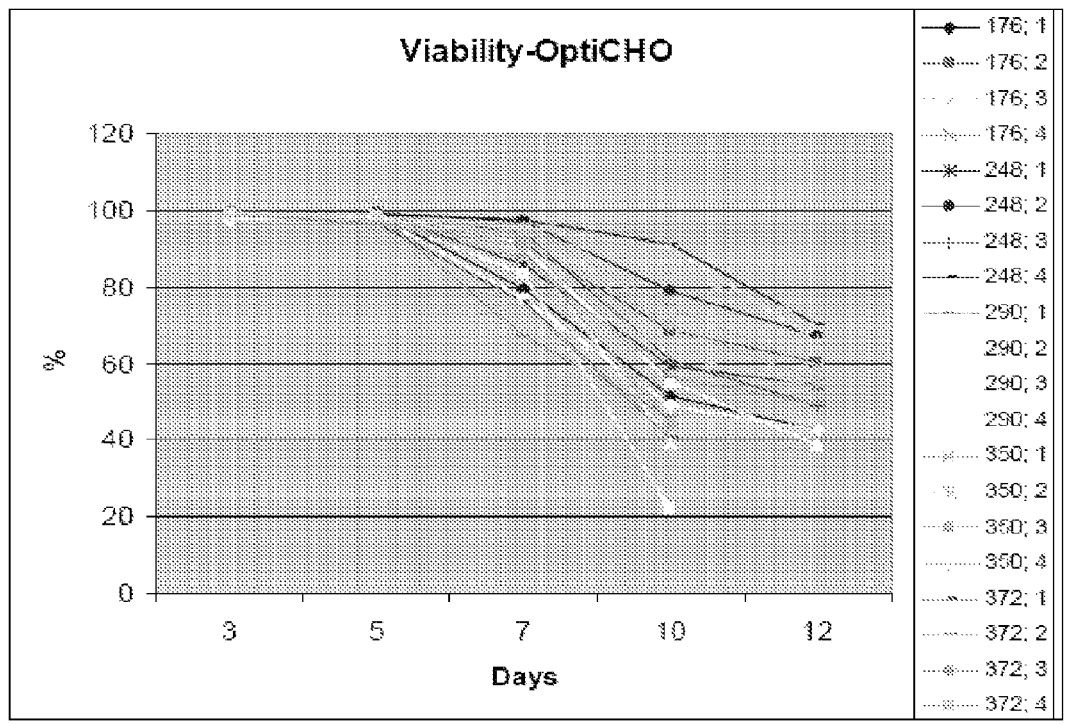
FIG. 7 depicts cell viability in OptiCHO™ medium of various apyrase-producing clones.
Figure 8:
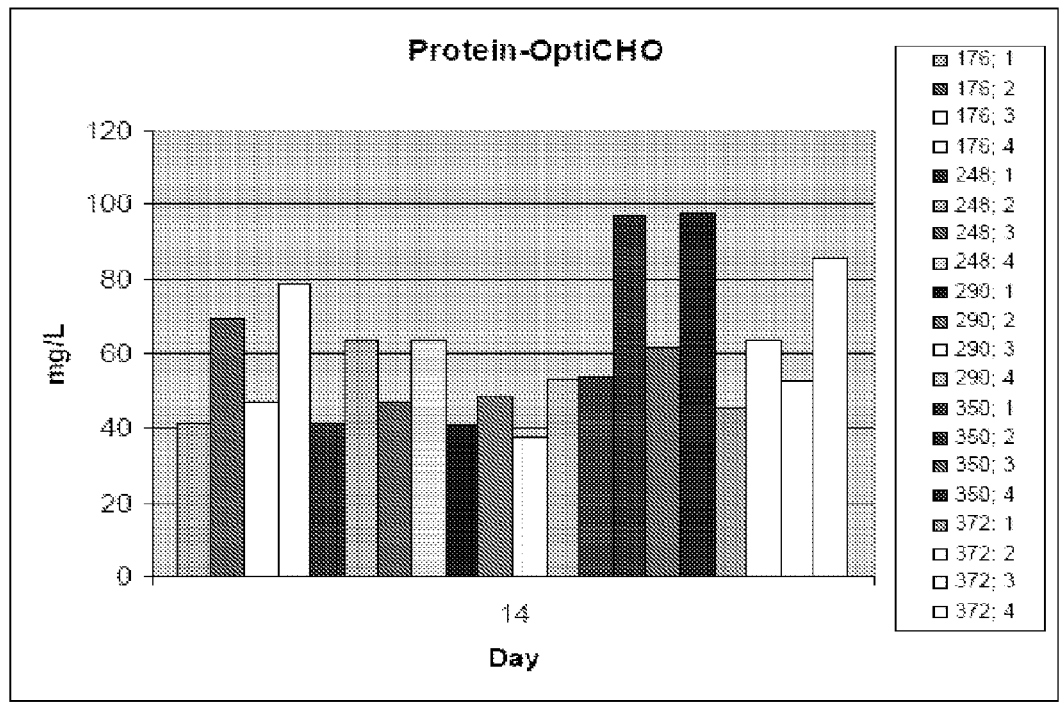
FIG. 8 depicts expression levels in PFCHO LS.

The position of Mfe1 and Xho I restriction sites used for cloning the DNA fragment into the host plasmid are shown. The first 19 codons encode the signal peptide. During DNA sequencing of the final construct, a silent mutation was detected at position 2879 (AAC instead of the predicted AAT). This codon is double underlined. The final vector was designated oCS-APT-WPRE (new ori) (FIG. 2).

TABLE 2

(SEQ ID NOS: 23-24)

```
                              Mfe I
2491 TCGAAAGCTT CTAGACAATT GCCGCCACC ATG ATG TCC TTT GTC TCT CTG 2540
                                   1 Met Met Ser Phe Val Ser Leu 7
                                     α-Lactalbumin Signal Peptide
2541 CTC CTG GTT GGC ATC CTA TTC CAT GCC ACC CAG GCC GAG GTC CTC 2585
   8 Leu Leu Val Gly Ile Leu Phe His Ala Thr Gln Ala Glu Val Leu 22
                                                  |EN-apyrase ->
2586 CCT CCA GGA CTG AAG TAT GGT ATT GTG CTG GAT GCC GGG TCT TCA 2630
  23 Pro Pro Gly Leu Lys Tyr Gly Ile Val Leu Asp Ala Gly Ser Ser 37
2631 GGG ACC CGC GTC TAC GTG TAT CAA TGG CCA GCA GAA AAA GAG AAT 2675
  38 Gly Thr Arg Val Tyr Val Tyr Gln Trp Pro Ala Glu Lys Glu Asn 52
2676 AAT ACC GGA GTG GTC AGT CAA ACC TTC AAA TGT AGT GTG AAA GGC 2720
  53 Asn Thr Gly Val Val Ser Gln Thr Phe Lys Cys Ser Val Lys Gly 67
2721 TCT GGA ATC TCC AGC TAT GGA AAT AAC CCC CAA GAT GTC CCC AGA 2765
  68 Ser Gly Ile Ser Ser Tyr Gly Asn Asn Pro Gln Asp Val Pro Arg 82
2766 GCC TTT GAG GAG TGT ATG CAA AAA GTC AAG GGG CAG GTT CCA TCC 2810
  83 Ala Phe Glu Glu Cys Met Gln Lys Val Lys Gly Gln Val Pro Ser 97
2811 CAC CTC CAC GGA TCC ACC CCC ATT CAC CTG GGA GCC ACG GCT GGG 2855
  98 His Leu His Gly Ser Thr Pro Ile His Leu Gly Ala Thr Ala Gly 112
2856 ATG CGC TTG CTG AGG TTG CAA AAC GAA ACA GCA GCT AAT GAA GTC 2900
 113 Met Arg Leu Leu Arg Leu Gln Asn Glu Thr Ala Ala Asn Glu Val 127
2901 CTT GAA AGC ATC CAA AGC TAC TTC AAG TCC CAG CCC TTT GAC TTT 2945
 128 Leu Glu Ser Ile Gln Ser Tyr Phe Lys Ser Gln Pro Phe Asp Phe 142
2946 AGG GGT GCT CAA ATC ATT TCT GGG CAA GAA GAA GGG GTA TAT GGA 2990
 143 Arg Gly Ala Gln Ile Ile Ser Gly Gln Glu Glu Gly Val Tyr Gly 157
2991 TGG ATT ACA GCC AAC TAT TTA ATG GGA AAT TTC CTG GAG AAG AAC 3035
 158 Trp Ile Thr Ala Asn Tyr Leu Met Gly Asn Phe Leu Glu Lys Asn 172
3036 CTG TGG CAC ATG TGG GTG CAC CCG CAT GGA GTG GAA ACC ACG GGT 3080
 173 Leu Trp His Met Trp Val His Pro His Gly Val Glu Thr Thr Gly 187
3081 GCC CTG GAC TTA GGT GGT GCC TCC ACC CAA ATA TCC TTC GTG GCA 3125
 188 Ala Leu Asp Leu Gly Gly Ala Ser Thr Gln Ile Ser Phe Val Ala 202
3126 GGA GAG AAG ATG GAT CTG AAC ACC AGC GAC ATC ATG CAG GTG TCC 3170
 203 Gly Glu Lys Met Asp Leu Asn Thr Ser Asp Ile Met Gln Val Ser 217
3171 CTG TAT GGC TAC GTA TAC ACG CTC TAC ACA CAC AGC TTC CAG TGC 3215
 218 Leu Tyr Gly Tyr Val Tyr Thr Leu Tyr Thr His Ser Phe Gln Cys 232
3216 TAT GGC CGG AAT GAG GCT GAG AAG AAG TTT CTG GCA ATG CTC CTG 3260
 233 Tyr Gly Arg Asn Glu Ala Glu Lys Lys Phe Leu Ala Met Leu Leu 247
3261 CAG AAT TCT CCT ACC AAA AAC CAT CTC ACC AAT CCC TGT TAC CCT 3305
 248 Gln Asn Ser Pro Thr Lys Asn His Leu Thr Asn Pro Cys Tyr Pro 262
```

TABLE 2-continued (SEQ ID NOS: 23-24)

```
3306 CGG GAT TAT AGC ATC AGC TTC ACC ATG GGC CAT GTA TTT GAT AGC 3350
 263 Arg Asp Tyr Ser Ile Ser Phe Thr Met Gly His Val Phe Asp Ser 277

3351 CTG TGC ACT GTG GAC CAG AGG CCA GAA AGT TAT AAC CCC AAT GAT 3395
 278 Leu Cys Thr Val Asp Gln Arg Pro Glu Ser Tyr Asn Pro Asn Asp 292

3396 GTC ATC ACT TTT GAA GGA ACT GGG GAC CCA TCT CTG TGT AAG GAG 3440
 293 Val Ile Thr Phe Glu Gly Thr Gly Asp Pro Ser Leu Cys Lys Glu 307

3441 AAG GTG GCT TCC ATA TTT GAC TTC AAA GCT TGC CAT GAT CAA GAA 3485
 308 Lys Val Ala Ser Ile Phe Asp Phe Lys Ala Cys His Asp Gln Glu 322

3486 ACC TGT TCT TTT GAT GGG GTT TAT CAG CCA AAG ATT AAA GGG CCA 3530
 323 Thr Cys Ser Phe Asp Gly Val Tyr Gln Pro Lys Ile Lys Gly Pro 337

3531 TTT GTG GCT TTT GCA GGA TTC TAC TAC ACA GCC AGT GCT TTA AAT 3575
 338 Phe Val Ala Phe Ala Gly Phe Tyr Tyr Thr Ala Ser Ala Leu Asn 352

3576 CTT TCA GGT AGC TTT TCC CTG GAC ACC TTC AAC TCC AGC ACC TGG 3620
 353 Leu Ser Gly Ser Phe Ser Leu Asp Thr Phe Asn Ser Ser Thr Trp 367

3621 AAT TTC TGC TCA CAG AAT TGG AGT CAG CTC CCA CTG CTG CTC CCC 3665
 368 Asn Phe Cys Ser Gln Asn Trp Ser Gln Leu Pro Leu Leu Leu Pro 382

3666 AAA TTT GAT GAG GTA TAT GCC CGC TCT TAC TGC TTC TCA GCC AAC 3710
 383 Lys Phe Asp Glu Val Tyr Ala Arg Ser Tyr Cys Phe Ser Ala Asn 397

3711 TAC ATC TAC CAC TTG TTT GTG AAC GGT TAC AAA TTC ACA GAG GAG 3755
 398 Tyr Ile Tyr His Leu Phe Val Asn Gly Tyr Lys Phe Thr Glu Glu 412

3756 ACT TGG CCC CAA ATA CAC TTT GAA AAA GAA GTG GGG AAT AGC AGC 3800
 413 Thr Trp Pro Gln Ile His Phe Glu Lys Glu Val Gly Asn Ser Ser 427

3801 ATA GCC TGG TCT CTT GGC TAC ATG CTC AGC CTG ACC AAC CAG ATC 3845
 428 Ile Ala Trp Ser Leu Gly Tyr Met Leu Ser Leu Thr Asn Gln Ile 442

3846 CCA GCT GAA AGC CCT CTG ATC CGT CTG CCC ATA GAA CCA CCT GTC 3890
 443 Pro Ala Glu Ser Pro Leu Ile Arg Leu Pro Ile Glu Pro Pro Val 457
                  Xho I           Cla I
3891 TGA TGAGATC TCGAGTTCGA CATCGATAAT CAACCTCTGG ATTACAAAAT 3940
 458 TRM 458
```

Example 2

Transformation of CHO Cells with oCS-APT-WPRE (New ori)

Chinese Hamster Ovary (CHO) production cell lines were made by two rounds of transduction of the CHO parental cell line with retrovector constructed in Example 1. The pooled population of transduced cells was named sCHO-S/sC-APT-R 2×. Samples of the pooled population cell lines were cryopreserved after each transduction. The pooled population of sCHO-S/sC-APT-R 2× cells was diluted to very low cell density (approximately 0.5 or 0.75 viable cells per 200 μL media) and plated in 96 well microtiter plates to establish clonal cell lines that originated from single cells. A total of 560 clones were screened for EN-apyrase production by Malachite Green assay after 14 days of incubation. Twenty four of the top clones based on EN-apyrase production were expanded from 96 well plates to 24 well plates. Twenty of the 24 clones survived expansion and were cryopreserved.

The 20 clones were screened in triplicate T175 flasks for productivity. The top 5 clones chosen were clones 176, 248, 290, 350 and 372. Selected clonal lines of sCHO-S/sC-APT-R 2× cells were tested for replication competent retrovirus (RCR), mycoplasma contamination and bioburden with negative results.

The cell lines prepared above were passaged every 3-4 days during exponential phase for all of the studies outlined below, maintaining a viability of 90% or better in both PFCHO LS (HyClone) and CD OptiCHO™ (Invitrogen) media. Cells were inoculated at a cell density of 300,000 cells/ml in each medium and incubated in a Multitron shaking incubator at a speed of 150 rpm. The initial temperature set point was 37° C. The temperature was shifted to 31° C. on Day 5 under Conditions 2 and 4. The $CO_2$ set point was 5% and the Feed Supplement: was HyClone supplements R15.4 and PS307 and glutamine.

Four different conditions, as outlined below, were performed in duplicate 125 mL shake flask (50 mL total volume) for each clone. There were only enough cells of clone #248 in PFCHO LS to be tested under Conditions 1 and 2. Shakers were harvested on Day 14.

Condition 1
  Day 0: 3 g/L PS307
  Day 2: 3 g/L PS307+3 mM glutamine
  Day 4: 3 g/L R15.4+3 mM glutamine
  Day 6: 12 g/L R15.4
Condition 2
  Day 0: 3 g/L PS307
  Day 2: 3 g/L PS307+3 mM glutamine
  Day 4: 3 g/L R15.4+3 mM glutamine
  Day 5: Temperature shift to 31° C.
  Day 6: 12 g/L R15.4
Condition 3
  Day 0: 1.5 g/L PS307+1.5 g/L R15.4
  Day 2: 1.5 g/L PS307+1.5 g/L R15.4+3 mM glutamine
  Day 4: 1.5 g/L PS307+1.5 g/L R15.4+3 mM glutamine
  Day 6: 5 g/L PS307+5 g/L R15.4
Condition 4
  Day 0: 1.5 g/L PS307+1.5 g/L R15.4
  Day 2: 1.5 g/L PS307+1.5 g/L R15.4+3 mM glutamine
  Day 4: 1.5 g/L PS307+1.5 g/L R15.4+3 mM glutamine
  Day 5: Temperature shift to 31° C.
  Day 6: 5 g/L PS307+5 g/L R15.4

The results from the various conditions and media are shown in FIG. 3 through FIG. 8 below. The cell densities peaked at $60 \times 10^5$ cells/mL in the PFCHO LS medium (Clone #176) and $160 \times 10^5$ cells/mL in the OptiCHO™ medium (Clone #176).

The results demonstrate various useful conditions for culturing the CHO cells for production of EN-apyrase. These results also indicate that the productivity was not directly related to cell density.

The addition of a temperature shift in the OptiCHO™ cultures generated a significant increase in the overall titer which led to the selection of either condition 2 or 4 in OptiCHO™ as the preferred method of culturing Clone #350.

Example 3

Improved Cell Culture Conditions to Increase Protein Yield in 10 L Bioreactors

Background:

Preliminary studies show that PowerCHO®-2 medium resulted in higher yield and better glycosylation of EN-apyrase in shaking flasks. Two different conditions were run in 10 L bioreactors (Vessel 1 and 2) in which the pH was maintained at 7.4. An additional 10 L bioreactor (Vessel 3) was run under the same condition as Vessel 2 but with a natural drift of the pH down to 7.0.

Materials and Methods:

Cell line CHO-S-APT-R Clone #350 was passaged every 3-4 days during the exponential growth phase for scale-up for the 10 L Braun bioreactors. Cells were inoculated at a cell density of approximately 300,000-400,000 cells/ml in PowerCHO®-2 (Lonza) medium into three 10 L bioreactors. Fed-batch supplements used for this study were HyClone PS307 (12% (w/v) solutions), AGT CD CHO 5× Feed Medium Complete (Invitrogen), AGT CD CHO 5× Feed Medium Complete+12.5 g/L galactose (Invitrogen), 45% glucose solution, 20% glucose/galactose solution, 200 mM L-glutamine, 50× solution of L-Asparagine (15 g/L)/L-Serine (10 g/L), 50× solution of L-Tyrosine (4 g/L)/L-Cystine (2 g/L).

Condition 1
  D0: 3 g/L PS307+2 mM glutamine
  D1: Maintain glutamine to 2 mM; Maintain glucose to 5 g/L
  D2: 3 g/L PS307+glucose (to 5 g/L)+glutamine (to 2 mM)
  D3: Maintain glutamine to 2 mM; Maintain glucose to 5 g/L
  D4: 3 g/L R15.4/PS307 (1:1)+glutamine (to 2 mM)+glucose (to 5 g/L)
  D5: Maintain glutamine to 2 mM; Maintain glucose to 5 g/L
  D5: Temperature shift to 34° C.
  D6: 12 g/L R15.4
  D6: Maintain glutamine to 2 mM; Maintain glucose to 4 g/L
  D7-D16: Maintain glutamine to 2 mM; Maintain glucose to 4 g/L
  pH 7.4 throughout the run
Condition 2
  D0: 3 g/L PS307
  D1: Maintain glutamine to 2 mM
  D 3: 30% v/v (AGT CD 5× Medium Complete+12.5 g/L galactose)+1× L-Asparagine (0.3 g/L)/L-Serine (0.2 g/L)+1× L-Tyrosine (80 mg/L)/L-Cystine (40 mg/L)+3 mM Glutamine if VCD≥$10 \times 10^5$ cells/ml on Day 2 or Day 3 by default
  D4-D5; Maintain glutamine to 2 mM
  Day 5: Temperature shift to 34° C.
  D6-D16: Feed 10% (v/v) (AGT CD 5× Feed Medium Complete+12.5 g/L galactose) when glucose levels are ~5 g/L
  D6-D16 Post 10% 5× Feed: Feed 3 g/L glucose/galactose when glucose levels are ~3 g/L
  pH 7.4 throughout the run
Condition 3
  D0: 3 g/L PS307
  D1: Maintain glutamine to 2 mM
  D3: 30% v/v (AGT CD 5× Medium Complete+12.5 g/L galactose)+1× L-Asparagine (0.3 g/L)/L-Serine (0.2 g/L)+1× L-Tyrosine (80 mg/L)/L-Cystine (40 mg/L)+3 mM Glutamine
  D4-D5; Maintain glutamine to 2 mM
  Day 5: Temperature shift to 34° C.
  D6-D16: Feed 10% (v/v) (AGT CD 5× Feed Medium Complete+12.5 g/L galactose) when glucose levels are ~5 g/L
  D6-D16 Post 10% 5× Feed: Feed 3 g/L glucose/galactose when glucose levels are ~3 g/L
  pH natural drift to 7.0±0.05

Results:

Vessel 3 had the highest peak cell density ($70 \times 10^5$ cells/mL). Vessels 1 and 2 peaked at $48 \times 10^5$ cells/mL. Vessel 1 harvested at day 14, Vessel 2 at day 16 and Vessel 3 at day 15. All the vessels were <50% viability at harvest. Maximum protein levels (activity assay) for Vessels 2 and 3 were 55 mg/L at harvest. Vessel 1 had a protein level of 51 mg/L at harvest. Glucose was not rate-limiting for any of the vessels. Glutamine levels were low at the end of the runs for Vessels 2 and 3. Lactate levels were high for Vessels 1 and 2 (~6 g/L) while vessel 3 was <2.5 g/L. Ammonium levels stayed below 10 mM for Vessels 1 and 2 and ~16 mM for Vessel 3.

Conclusion:

Overall, protein levels were better for conditions 2 and 3. Lactate levels were much higher in Vessels 1 and 2 which resulted in over 1 L of base added to help maintain the pH. Vessel 3 required only 200 mL of base to maintain pH throughout the entire run. The addition of the base also caused the osmolality (data not shown) to be much higher (~540 mmol/kg for Vessel 1 and ~500 mmol/kg for Vessel 2) than Vessel 3 (~365 mmol/kg). From the protein analysis, protein quality does not appear to differ between the three conditions used in this study.

Example 4

Stability of Transformed CHO Cells Expressing EN-Apyrase

A CHO cell line produced as in Example 2 was thawed and cultured in 125 ml shaker flasks using CD OptiCHO™ media. Since the CHO cells were previously grown in PF CHO LS media, the shaker flask was carried through five passages to adapt the culture to the new media. The cells after adaptation were designated generation 0 for this study. Cells were continuously cultured by serial passage. The plan for the study was to compare cells after approximately 10, 15 and 20 generations of continuous culture. At generations 9, 17 and 24, samples of cells were frozen. At the end of the culturing, samples of cells from generations 0, 9, 17 and 24 were thawed and used to conduct terminal batch culture runs to compare EN-apyrase production of the cell line at different generations in the same experiment. The terminal culture did not include feeds and temperature shifts, as done during process development. The expression level of apyrase as determined by the Malachite green ADP hydrolysis activity assay was shown to be comparable for generations 0 and 24, respectively.

To compare the stability of gene inserts, samples of CHO cells after 0, 9, 17 or 24 generations were used for DNA isolation. Using real-time PCR on genomic DNA, the number of genetic inserts remained steady in the cell line over the next 40 generations. The PCR based index of copy number for the different generations were not significantly different for the different generations.

Example 5

Stability of Protein Production in Cell Culture

The cultures of Example 2 were incubated in 125 ml shaker flasks in 50 mL of media. CD OptiCHO™ media (Gibco Cat. #12681-011, Lot 06291004, Exp. Aug. 30, 2007) medium with 6 mM L-glutamine (HyClone Cat. #SH30034.01, Lot 06263003) was used throughout. This cell line (Passage 6) was thawed and used to initiate the culture. Since the cell line had previously been cultured in PF CHO LS media, the culture was carried through five passages in the CD OptiCHO™ media to adapt the cells to the new media. Cultures were initially seeded at a target density of $2.5 \times 10^5$ viable cells/mL. Cells were passaged twice a week by taking a cell count with a Cedex™ instrument (Innovatis, Germany) and diluting the culture to the target density in fresh media. The weekly cell count data for the Research Cell Bank sample are shown in Table 3.

TABLE 3

| Passage Number | Cell Viability (%) | Cell Count (cells/ml) | Generation Number |
|---|---|---|---|
| 7 | 81.3 | 0.46 | Adaptation to CD OptiCHO ™ media |
| 8 | 95.4 | 4.39 | |
| 9 | 97.5 | 70.26 | |
| 10 | 98.6 | 23.65 | |
| 11 | 99.1 | 40.12 | |
| 12 | 98.9 | 32.31 | |
| 13 Freeze | 98.9 | 73.96 | 0.00 |
| 14 | 99.5 | 43.79 | 4.14 |
| 15 Freeze | 98.9 | 82.33 | 9.21 |
| 16 | 98.5 | 17.58 | 12.05 |
| 17 Freeze | 95.9 | 68.09 | 16.87 |
| 18 | 97.6 | 14.19 | 19.37 |
| 19 Freeze | 94.3 | 73.72 | 24.32 |

Calculations:

Generation Number (G): $G = LN$ (total cell count÷total cell count seeded) 0.69.

Direct Comparison of Generations 0, 10, 15 and 20.

After approximately 0, 10, 15 or 20 generations of culturing as described above, cells from each shaker flask were frozen down in freezing medium (46.25% conditioned media, 46.25% fresh media, 7.5% DMSO (Sigma Cat #D2650, lot 46K2381). The vials were placed at −80° C. for 1-7 days and then transferred to liquid nitrogen for storage.

Upon completion of the culturing for 20 generations, frozen cells from the starting cell line after adaptation to CD OptiCHO™ media (generation 0), generation 9, generation 17 and generation 24 vials were thawed. Each of the samples was inoculated into triplicate 125 mL shaker flasks starting with approximately 250,000 cells/mL, using CD OptiCHO™ medium. Cultures were grown at 37° C. in a 5% $CO_2$ atmosphere shaking at 140 rpm. Samples were collected on day 14 of culture for protein analysis. Levels of production of apyrase were estimated using the Malachite green activity assay previously described.

Results.

Terminal Culture with Cells at Generations 0, 9, 17 and 24.

Figure 9:
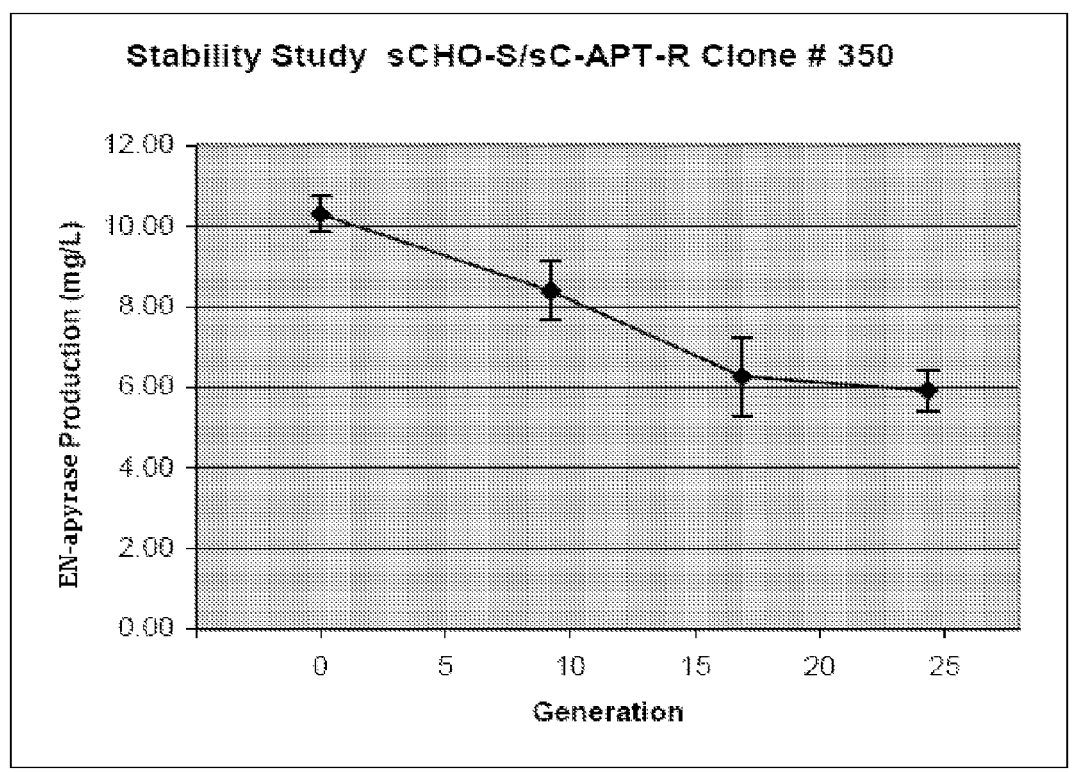
FIG. 9 shows the stability of EN-apyrase production over 25 generations of clone 350.

The results below show the analysis of samples for apyrase expression during the side by side comparison of the starting cell line (research cell bank at generation 0 after adaptation to CD OptiCHO™ media) and cell lines after 9, 17 and 24 generations. Each generation sample was cultured in triplicate and the results were averaged. The error bars show the standard deviation of the samples for each generation. FIG. 9 shows the average day 14-protein production for each of the four generation levels.

SDS PAGE Analysis.

Samples of media containing EN-apyrase protein were collected from day 14 of productivity tests. The proteins were separated on polyacrylamide gel electrophoresis. Briefly, media samples (20 μL) were prepared in reducing sample buffer and heated at 70° C. for 5 min. Size standards were SeeBlue® Plus 2 protein standards. (Invitrogen Cat #LC5925). Samples were loaded on to a 4-12% Bis-Tris NuPage® gel (Invitrogen, Cat. #NP0321) and electrophoresed at 200V for 60 minutes. The gel was stained with Gelcode™ Blue stain (Pierce Cat. #24592) at room temperature for 45 minutes. Production of EN-apyrase remained constant over 24 generations.

The stability of gene inserts from cells of various generations was compared using a gene copy index assay.

A sample of the EN-apyrase producing CHO cell line, Clone #350, from the research cell bank after adaptation to CD OptiCHO™ media was used to isolate genomic DNA for a generation 0 sample. Samples of the generation 9, 17 and 24 EN-apyrase producing CHO cell lines for clone #350, were also used to isolate genomic DNA. The gene copy index of the EPR relative to the control β 1, 4 gal actosyltransferase was measured using real time PCR. The results shown below demonstrate that there is no significant change in the gene copy index values over the 20 generations. This indicates that the number of transgene inserts does not change over extended passage of the cell line.

| Generation | Gene index | Std. Dev. |
|---|---|---|
| 0.0 | 3.67 | 0.25 |
| 9.2 | 3.83 | 0.12 |
| 16.9 | 3.47 | 0.21 |
| 24.3 | 3.77 | 0.06 |

Values represent the mean and standard deviation of triplicates.

Example 6

Homogeneous N-Terminal Amino Acid Sequence of EN-Apyrase

Among the top 5 clones clone 350 was chosen to produce EN-apyrase from the CHO cell line. Conditioned medium was harvested from the sCHO-S/sC-APT-R 2× cell culture of clone 350 harboring pCS-APT-WPRE (new ori) to purify EN-apyrase. Purification was performed in the same way using DEAE and Heparin chromatographies as in Preparation A. Purified EN-apyrase was subjected to 4-12% SDS-PAGE gel in the presence of 2-mercaptoethanol and gave a single band at 70 kDa associated with apyrase activity. After completion of electrophoresis, the gel was immersed into a transfer buffer (25 mM Bicine, 25 mM Bis-Tris, 1 mM EDTA, 0.05 mM chlorobutanol, 10% methanol, pH 7.2) for 5 minutes, overlaid to PVDF membrane (Immovilon, Millipore), which has previously been immersed successively into 100% methanol and the transfer buffer, and the protein was transferred with XCell II™ Blot Module (Invitrogen) at 160 mA for 1 hour. The PVDF membrane after transfer was washed with water, stained with Coomassie° Brilliant Blue R-250 Staining Solution (Bio-Rad) for 1 minute and washed with distilled water.

The stained band at 70 kDa was excised and the membrane segment was analyzed by Edman Sequence Analysis. The N-terminal amino acid sequence was a single species and its N-terminal amino acid residues were determined as: Glu-Val-Leu-Pro-Pro-Gly-Leu-Lys-Tyr-Gly-Ile (positions 20-30 of SEQ ID NO:24); thus cleavage occurs at position 28 of SEQ ID NO:9. This represented only 40% of the product in HEK293T cells producing HEK-sol-CD39L3-01.

Example 7

Carbohydrate Analysis of EN-Apyrase

Figure 10:
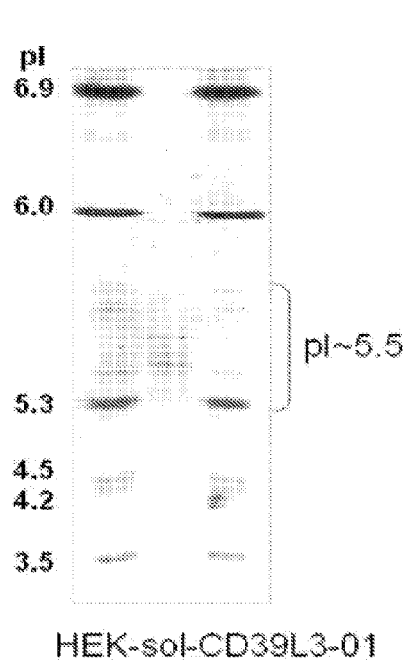
FIGS. 10A and 10B show the isoelectric points of HEK-sol-CD39L3-01 and EN-apyrase.
Figure 10:
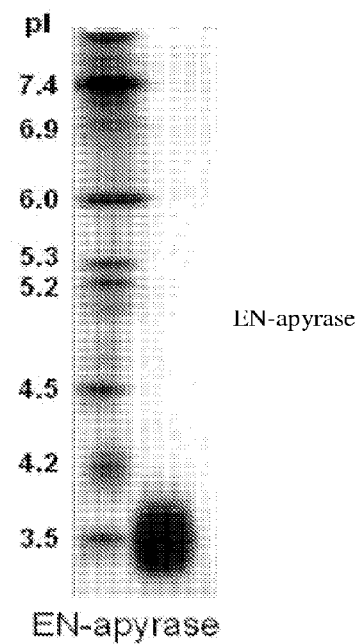

Carbohydrates from EN-apyrase vs. sol CD39L3 (HEK-sol-CD39L3-01) were analyzed by isoelectric focusing. EN-apyrases show substantially more glycosylation and with less heterogeneity as demonstrated by a pI in a range of about 3.0 to about 4.5 vs. a range of about 5.0 to about 6.0 for CD39L3-01. See FIGS. 10A and B. The higher molecular weight due to enhanced glycosylation was confirmed by SDS-PAGE.

Example 8

Improved Purification Protocol

An improved purification protocol was developed based upon new properties of the EN-apyrases. A two-ion exchange chromatography (ANX and SP) protocol was used instead of an ion exchange (DEAE) and an affinity chromatography (Heparin) as used in Preparation A and Example 6.

CHO cells transformed with an EN-apyrase construct comprising SEQ ID NO:10 were cultured generally as described above and the media was harvested through a 1.4 ft$^2$ 60M02 Depth Filter (Cuno, Conn.). The filter was washed prior to use with WFI water and was blown down with compressed air to maximize volumetric recovery. Clarified media was then filtered through a 0.2 μm filter and collected in a sterile bag.

For viral inactivation, the load (1.6 L clarified media, V17) was diluted with an equal volume (1.6 L) of WFI water. A solution of Triton® X-100 (320 mL of 11%) was added (1% final) and the resulting solution was incubated at ambient temperature for 30 minutes.

Anion Exchange Chromatography.

The viral inactivated culture media (3.52 L) was applied at a flow rate of 13 ml/min to 80 mL ANX Sepharose FF (GE Healthcare) column equilibrated with 10 mM Tris-HCl, pH 7.4. The load was applied to the column and the flow-thru, plus wash, was collected (3.7 L). A second wash of 10 mM Tris, 140 mM NaCl, pH 7.4 was performed and collected (580 mL). The protein was eluted with 10 mM Tris, 230 mM NaCl, pH 7.4 and collected (500 mL). Finally, the column was stripped of remaining protein with 1 M NaCl and this too, was collected (450 mL).

Buffer Exchange and Cation Exchange Chromatography.

The collected ANX 140 mM-230 mM elution volume was buffer exchanged (~10 volumes) in continuous mode using a Pellicon Biomax 30 50 cm$^2$ into 20 mM citrate, pH 4.80. The buffer exchanged load (1.0 L) was applied to 80 mL SP-Sepharose FF (GE Healthcare) column equilibrated in 20 mM citrate, pH 4.80 and the flow-thru, plus wash, collected (1.2 L). A wash step was performed with 20 mM citrate, pH 5.10, collected (220 mL). The column was stripped of remaining protein with 20 mM citrate, pH 6.0 and this too, was collected (200 mL).

Yield and Purity Analysis.

EN-apyrase yield was calculated to be greater than 80% by UV/vis absorption and by ELISA as presented.

| Sample | Volume (mL) | [Protein] (mg/mL) | Total Protein (mg) | Step Yield (%) | Overall Yield (%) |
|---|---|---|---|---|---|
| Clarified media | 1600 | *0.0458 | *73.3 | 100 | 100 |
| ANX 140 wash | 580 | 0.26 | 150.8 | — | — |
| ANX 230 elute pool | 500 | 0.32 | 160 | 218 | 218 |
| BE ANX elute/SP load | 1000 | 0.10 | 100 | 62.5 | 136 |
| SP pH 4.8 flow-thru | 1200 | 0.05 | 60 | 60.0 | 81.9 |
| SP pH 5.1 wash | 220 | 0.01 | 2.2 | — | — |
| SP pH 6.0 strip | 200 | 0.10 | 20 | — | — |

Figure 11:
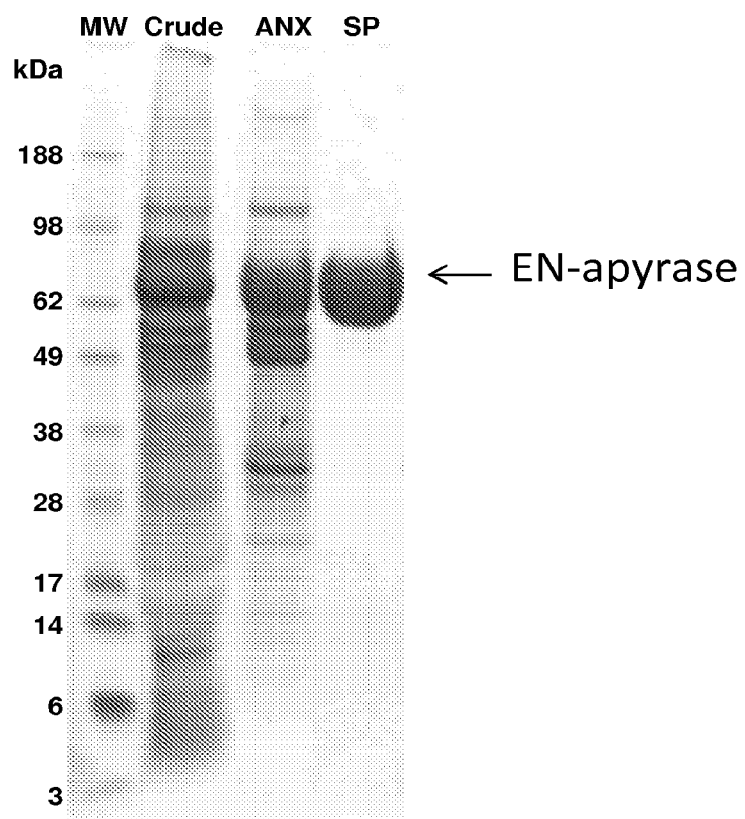
FIG. 11 shows the progress of purification protocol of EN-apyrase using two ion exchange chromatography steps.

SDS-PAGE analysis on each purification step was performed (FIG. 11). Purity was analyzed in SD-PAGE gel after 20× concentration using YM-30 2 ml centrifuge concentrators.

Example 9

Purification of EN-Apyrase with Improved Recovery of Heterogeneously Glycosylated EN-Apyrase The media from cells cultured as described in Example 2 was harvested through a 1.4 ft$^2$ 60M02 Depth Filter (Cuno, Conn.). The filter was washed prior to use with WFI water and was blown down with compressed air to maximize volumetric recovery. Clarified media was then filtered through a 0.2 μm filter and collected in a sterile bag.

For viral inactivation, the load (100 mL clarified media, V19) was diluted with an equal volume (100 mL) of Milli-Q water. A solution of Triton® X-100 (20 mL of 11%) was added (1% final) and the resulting solution was incubated at ambient temperature for 30 minutes.

Anion Exchange Chromatography.

Viral inactivated culture media (220 mL) of EN-apyrase was applied at a flow rate of 5 ml/min to 5 mL ANX Sepharose FF (GE Healthcare) column equilibrated with 10 mM Tris-HCl, pH 7.4. The load was applied to the column and the flow-thru, plus wash, was collected (260 mL). The protein was eluted with 10 mM Tris, 230 mM NaCl, pH 7.4 and collected (50 mL). By skipping the wash step and direct elution with 230 mM NaCl there was no significant loss of apyrase from the anion exchange chromatography. Finally, the column was stripped of remaining protein with 1 M NaCl and this too, was collected (30 mL). Western blot analysis on 1 M NaCl strip showed almost no detection of apyrase in the fraction.

Buffer Exchange and Cation Exchange Chromatography.

The collected ANX 230 mM elution volume was buffer exchanged (~3 volumes) through 1 L G25 column into 20 mM citrate, pH 4.6. The buffer exchanged load (150 mL) was applied to 5 mL SP-Sepharose FF (GE Healthcare) column equilibrated in 20 mM citrate, pH 4.6 and the flow-thru, plus wash, collected (170 mL). A wash step was performed with 20 mM citrate, pH 4.8, collected (40 mL). It was additional achievement that lower molecular weight impurities were removed by lowering flow-thru pH from 4.8 to 4.6. Although a portion of apyrase was in pH 4.8 elute the total amount was less than 10% of pH 4.6 flow-thru. Another wash step was performed with 20 mM citrate, pH 5.1, collected (40 mL). The column was stripped of remaining protein with 20 mM citrate, pH 6.0 and this too, was collected (40 mL).

Its purity was analyzed on 4-12% SDS-PAGE gel after 20× concentration using Omega 3 kDa 2 ml centrifuge concentrators.

With this purification scheme almost all of heterogeneously glycosylated EN-apyrase was collected from ANX chromatography by omitting 120 mM and/or 140 mM NaCl wash step. Also by reducing 0.2 pH unit on SP chromatography achieved additionally was a higher purity of apyrase (>95%). From this two step purification the overall recovery of apyrase was greater than 90%.

Example 10

EN-Apyrase Shows Prolonged Half Life and Improved Pharmacodynamics

5CHO-S/sC-APT-R 2× cells were cultured at pH 7.4, 34° C. in the presence of glucose at 4 g/L and glutamine at 2 mM. The EN-apyrase was purified via the 2-step ion exchange process of Example 9 and demonstrated a higher average molecular weight vs. HEK-sol-CD39L3-01, resulting from more abundant glycosylation.

Figure 12:
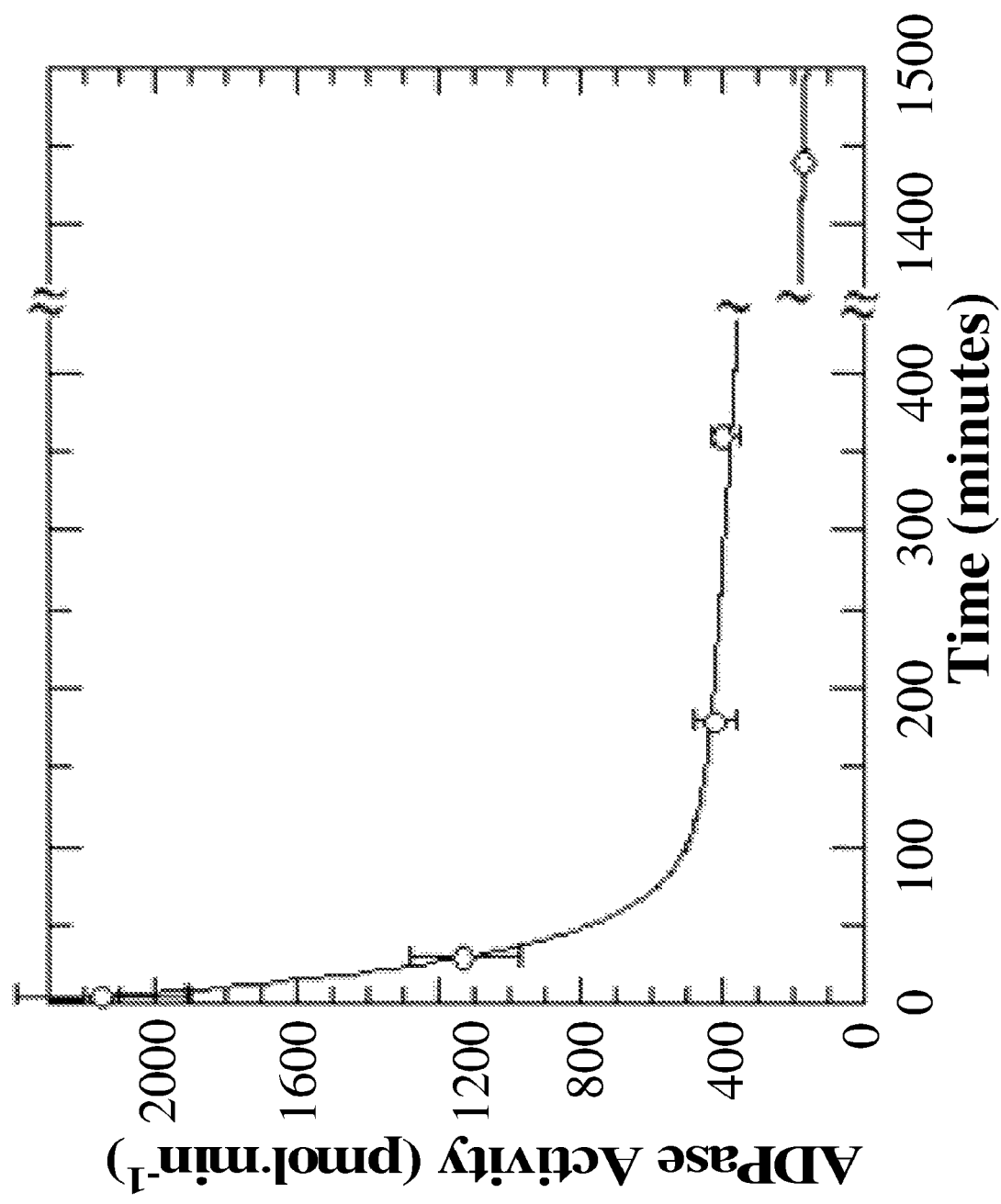
FIG. 12 shows the results of the determination of in vivo half-life of HEK-sol-CD39L3-01 in rabbits.
Figure 13:
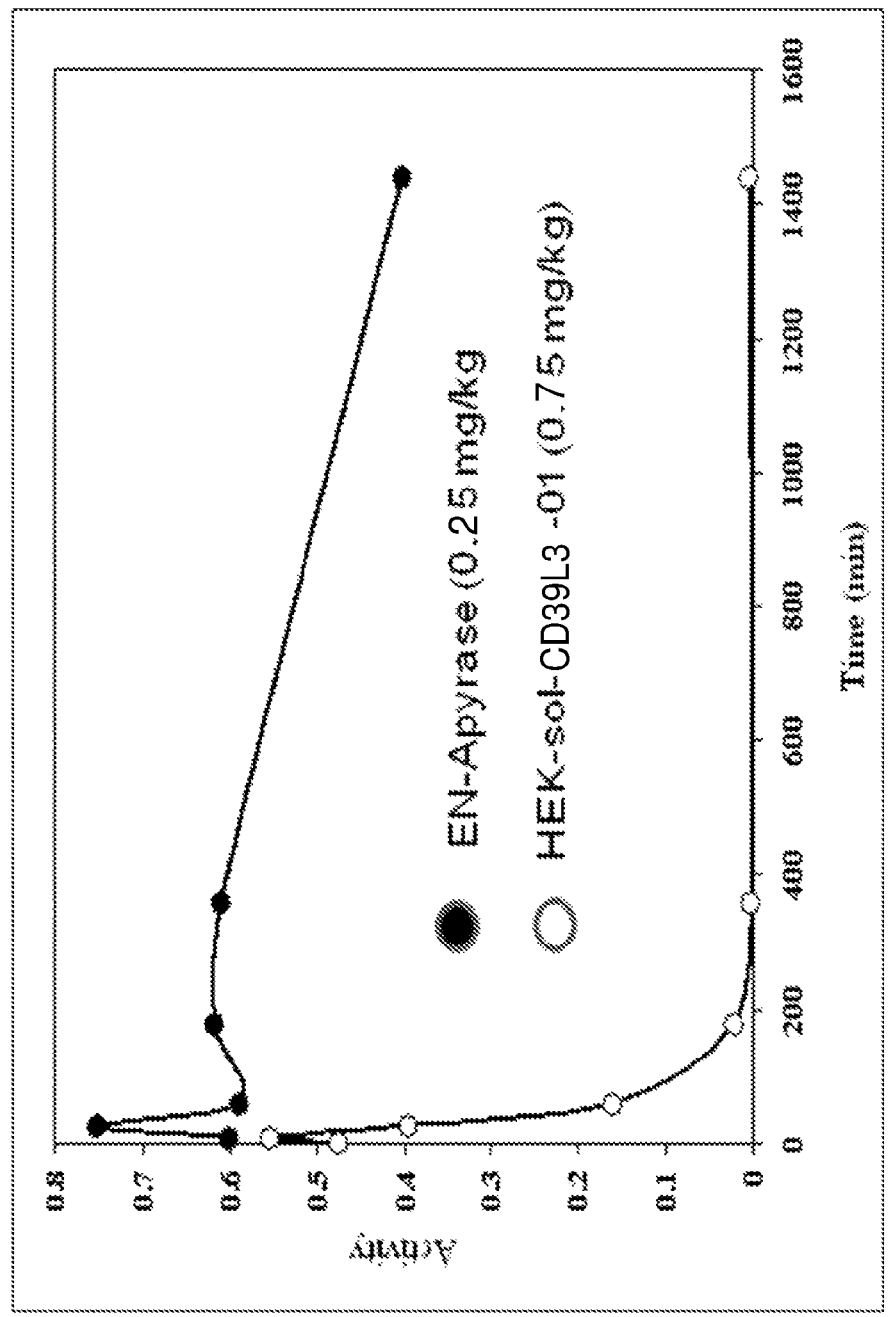
FIG. 13 shows the half-life of HEK-sol-CD39L3-01 in rabbits as compared to half-life of EN-apyrase.

As a control, pharmacokinetic studies were conducted in rats where single bolus sol-CD39L3 expressed in HEK cells, was intravenously injected (0.75 mg/kg, n=3 per time point). Serum samples were examined for ADPase and ATPase activity. The experimental data best fit biphasic exponential curves for either enzyme activity. The distribution phase half-life ($T_{1/2}$) of this apyrase was calculated to be 40 min (FIG. 12). Approximately 50% of apyrase activity was cleared from the circulation during this phase. This apyrase has a plasma elimination $T_{1/2}$ of 20 h. In contrast, EN-apyrase (administered at 0.25 mg/kg) retained >50% of the initial activity at 24 h, increasing the effective in vivo activity by >10× as shown in FIG. 13.

Figure 14:
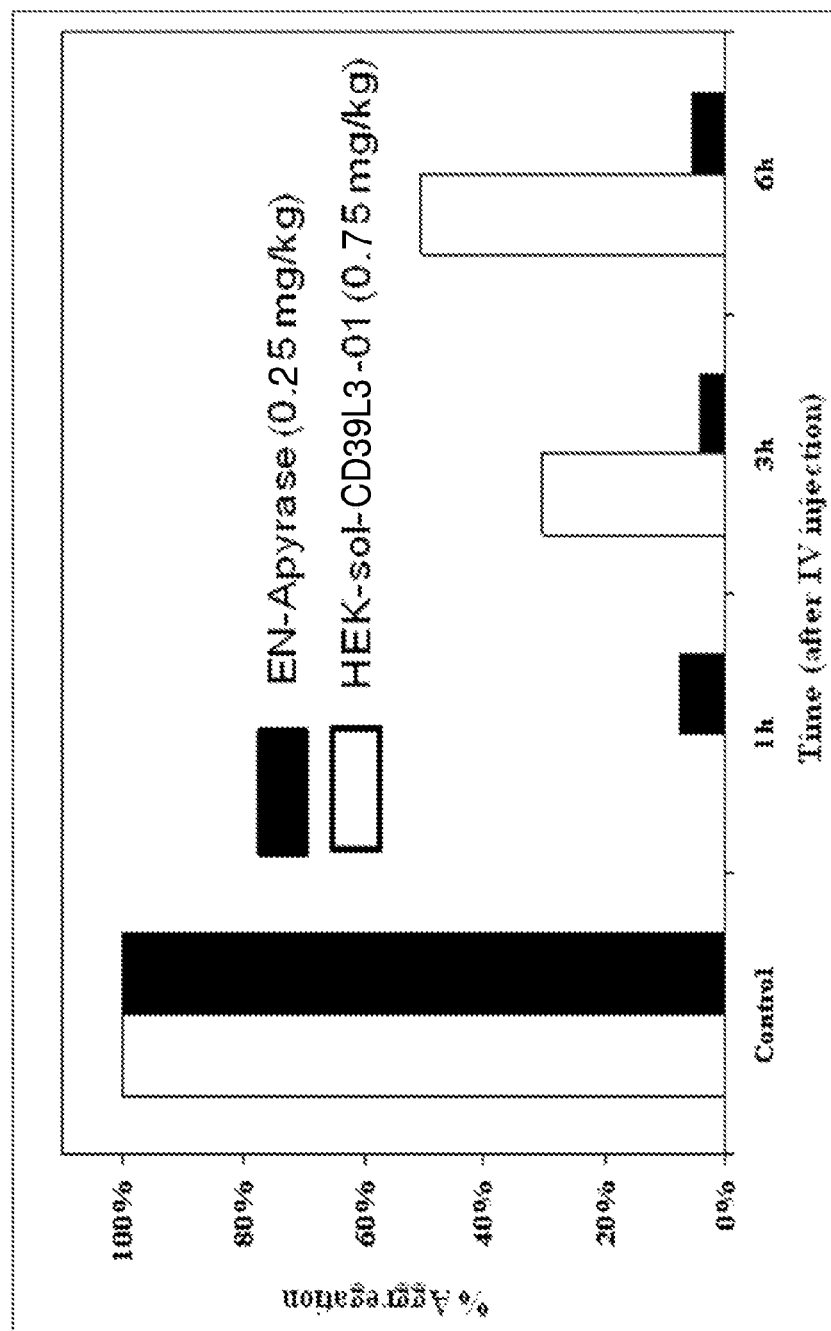
FIG. 14 depicts the results of FIG. 13 using an ex vivo test for ability to inhibit platelet aggregation.

The levels of active apyrase as measured by the effect of the EN-apyrase vs. HEK-sol-CDL3-sol on ADP-induced platelet aggregation in platelet rich plasma were determined at various time points after single bolus administration to rabbits (0.75 and 0.25 mg/kg of HEK-sol-CD39L3-01 and EN-apyrase respectively). To estimate inhibition of platelet aggregation by the apyrases more accurately, blood samples were heparinized, rather than citrated, in order to maintain physiological calcium concentrations. The data demonstrate that while soluble CD39L3 (e.g., HEK-sol-CD39L3-01) retained only 50% inhibition of ADP-induced platelet aggregation at 6 h, a 3× lower concentration (0.25 vs. 0.75 mg/kg) of EN-apyrase retained 90% inhibition of ADP-induced platelet aggregation at 6 h as shown in FIG. 14.

Figure 15:
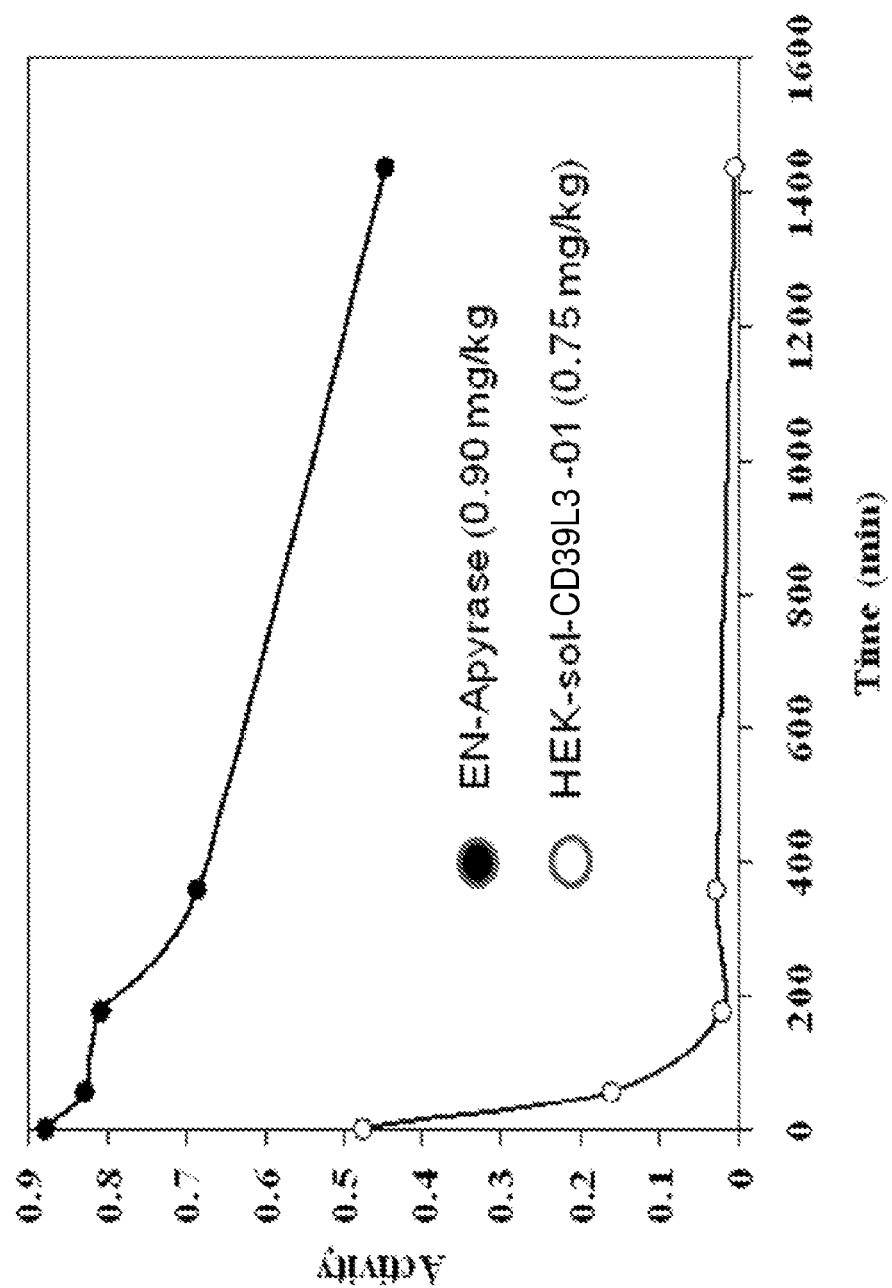
FIG. 15 shows results comparable to those in FIG. 13 but in pigs.
Figure 16:
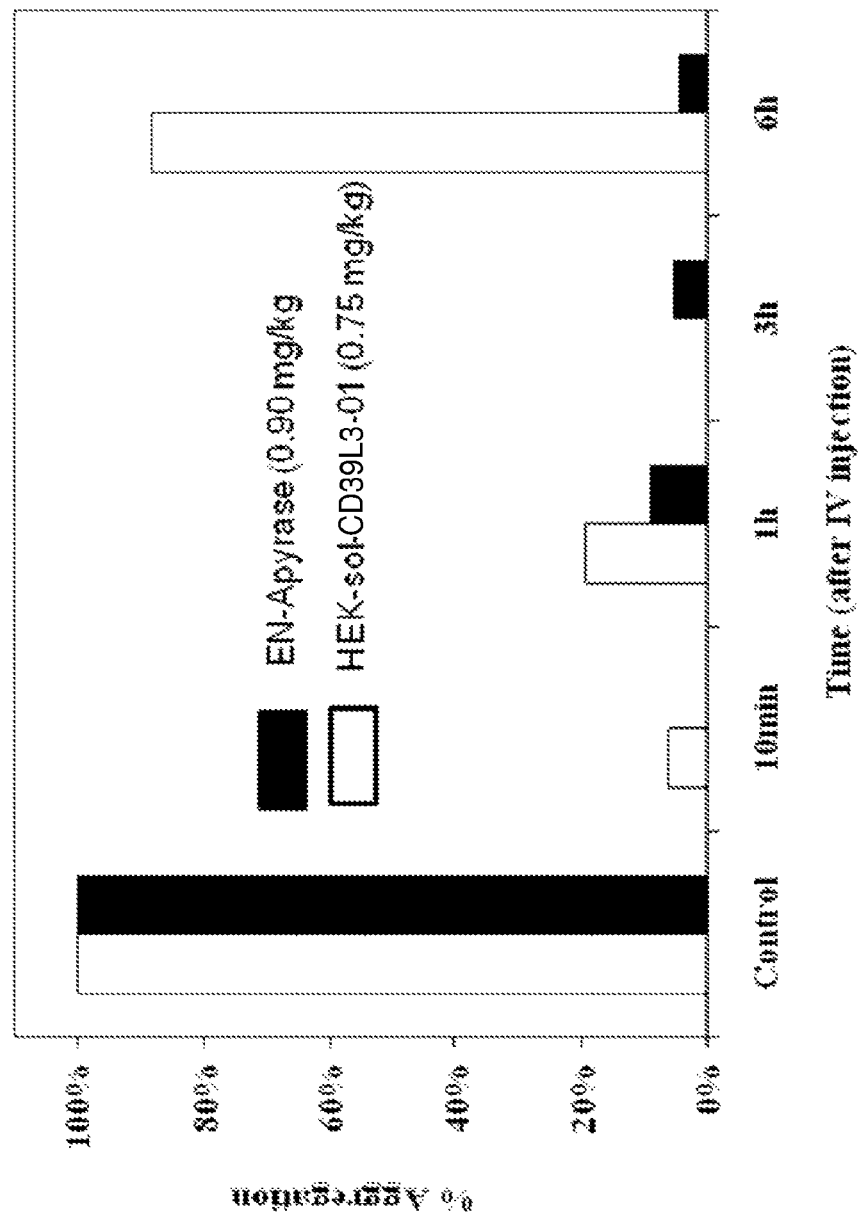
FIG. 16 shows results comparable to those of FIG. 14 but in pigs.

Similar improvement of pharmacokinetics by EN-apyrase was observed in pigs as shown in FIGS. 15 and 16. The >10 fold improvement in the pharmacokinetics of EN-apyrase would likely reduce the effective dose.

The invention claimed is:

1. A composition comprising an EN-apyrase, wherein the EN-apyrase is a soluble CD39L3 or a homolog thereof, which has a homogeneous N-terminus wherein more than 80% of the EN-apyrase molecules and homologs have the same N-terminus beginning with EVLP (positions 20-23 of SEQ ID NO:24) and wherein
   (a) the EN-apyrase has an average isoelectric point in the range of about 3.0 to about 4.5; and/or
   (b) the EN-apyrase has an in vivo half life in rabbits or pigs at least twice that of HEK sol-CD39L3-01, measured by apyrase assay,
   wherein the homolog of soluble CD39L3 is a sequence having 1 to 5 conservative substitutions with respect to positions 49-485 of SEQ ID NO:1 and/or is at least 80% identical to positions 49-485 of SEQ ID NO:1, and
   which retains ADP'ase and ATP'ase activity.

2. The EN-apyrase of claim 1 which is produced by a transformed CHO cell line.

3. The EN apyrase of claim 1 wherein the EN-apyrase consists of the amino acid sequence of positions 20-457 of SEQ ID NO:24.

4. A nucleic acid construct for production of an EN-apyrase of claim 1 comprising a nucleotide sequence encoding a signal sequence, a linker, and said soluble CD39L3 apyrase or homolog,
   wherein the linker has the sequence EVLP as its C-terminus and wherein said linker or a portion thereof may represent a sequence present in the native soluble apyrase, and
   an operably linked promoter functional in CHO cells so as to generate said EN-apyrase.

5. CHO cells comprising the construct of claim 4.

6. The construct of claim 4 wherein the EN-apyrase has the amino acid sequence of positions 20-457 of SEQ ID NO:24.

7. A method to prepare an EN-apyrase which method comprises culturing the cells of claim 5, and collecting the cultured medium.

8. The method of claim 7 wherein during culturing the medium maintains a glutamine concentration at about 1.5-4 mM and a pH of between 7.0 and 7.8 and wherein the temperature is shifted from 37° C. to 31° C.-35° C. at days 4-6 of culturing.

9. The method of claim 8, wherein during culturing the medium maintains a glutamine concentration at about 2 mM and a pH of 7.4 and wherein the temperature of the culture is shifted from 37° C. to 34° C. at day 5 of culturing.

10. An EN-apyrase prepared by the method of claim 7.

11. An EN-apyrase prepared by the method of claim 8.

12. An EN-apyrase prepared by the method of claim 9.

13. A pharmaceutical composition comprising the EN-apyrase of claim 1.

14. A pharmaceutical composition comprising the EN-apyrase of claim 10.

15. A method to treat conditions benefited by apyrase activity, which method comprises administering to a subject in need of such treatment an effective amount of the pharmaceutical composition of claim 13.

16. A method to treat conditions benefited by apyrase activity, which method comprises administering to a subject in need of such treatment an effective amount of the pharmaceutical composition of claim 14.

17. A method to purify the EN-apyrase of claim 1 which method comprises subjecting culture medium containing said EN-apyrase to anion exchange chromatography, followed by treating EN-apyrase containing eluate from said anion exchange chromatography to purification by cation exchange chromatography.

18. The EN-apyrase of claim 1, wherein more than 90% of the EN-apyrase molecules have the same N-terminus.

* * * * *

SEQUENCE LISTING

```
<160> NUMBER OF SEQ ID NOS: 24

<210> SEQ ID NO 1
<211> LENGTH: 529
<212> TYPE: PRT
<213> ORGANISM: Homo sapiens
<220> FEATURE:
<221> NAME/KEY: misc_feature
<222> LOCATION: (1)...(529)
<223> OTHER INFORMATION: CD39L3

<400> SEQUENCE: 1

Met Val Thr Val Leu Thr Arg Gln Pro Cys Glu Gln Ala Gly Leu Lys
 1               5                   10                  15

Ala Leu Tyr Arg Thr Pro Thr Ile Ile Ala Leu Val Val Leu Leu Val
            20                  25                  30

Ser Ile Val Val Leu Val Ser Ile Thr Val Ile Gln Ile His Lys Gln
```

-continued

```
                35                  40                  45
Glu Val Leu Pro Pro Gly Leu Lys Tyr Gly Ile Val Leu Asp Ala Gly
 50                  55                  60

Ser Ser Arg Thr Thr Val Tyr Val Tyr Gln Trp Pro Ala Glu Lys Glu
 65                  70                  75                  80

Asn Asn Thr Gly Val Val Ser Gln Thr Phe Lys Cys Ser Val Lys Gly
                 85                  90                  95

Ser Gly Ile Ser Ser Tyr Gly Asn Asn Pro Gln Asp Val Pro Arg Ala
                100                 105                 110

Phe Glu Glu Cys Met Gln Lys Val Lys Gly Gln Val Pro Ser His Leu
                115                 120                 125

His Gly Ser Thr Pro Ile His Leu Gly Ala Thr Ala Gly Met Arg Leu
                130                 135                 140

Leu Arg Leu Gln Asn Glu Thr Ala Ala Asn Glu Val Leu Glu Ser Ile
145                 150                 155                 160

Gln Ser Tyr Phe Lys Ser Gln Pro Phe Asp Phe Arg Gly Ala Gln Ile
                165                 170                 175

Ile Ser Gly Gln Glu Glu Gly Val Tyr Gly Trp Ile Thr Ala Asn Tyr
                180                 185                 190

Leu Met Gly Asn Phe Leu Glu Lys Asn Leu Trp His Met Trp Val His
                195                 200                 205

Pro His Gly Val Glu Thr Thr Gly Ala Leu Asp Leu Gly Gly Ala Ser
                210                 215                 220

Thr Gln Ile Ser Phe Val Ala Gly Glu Lys Met Asp Leu Asn Thr Ser
225                 230                 235                 240

Asp Ile Met Gln Val Ser Leu Tyr Gly Tyr Val Tyr Thr Leu Tyr Thr
                245                 250                 255

His Ser Phe Gln Cys Tyr Gly Arg Asn Glu Ala Glu Lys Lys Phe Leu
                260                 265                 270

Ala Met Leu Leu Gln Asn Ser Pro Thr Lys Asn His Leu Thr Asn Pro
                275                 280                 285

Cys Tyr Pro Arg Asp Tyr Ser Ile Ser Phe Thr Met Gly His Val Phe
                290                 295                 300

Asp Ser Leu Cys Thr Val Asp Gln Arg Pro Glu Ser Tyr Asn Pro Asn
305                 310                 315                 320

Asp Val Ile Thr Phe Glu Gly Thr Gly Asp Pro Ser Leu Cys Lys Glu
                325                 330                 335

Lys Val Ala Ser Ile Phe Asp Phe Lys Ala Cys His Asp Gln Glu Thr
                340                 345                 350

Cys Ser Phe Asp Gly Val Tyr Gln Pro Lys Ile Lys Gly Pro Phe Val
                355                 360                 365

Ala Phe Ala Gly Phe Tyr Tyr Thr Ala Ser Ala Leu Asn Leu Ser Gly
                370                 375                 380

Ser Phe Ser Leu Asp Thr Phe Asn Ser Ser Thr Trp Asn Phe Cys Ser
385                 390                 395                 400

Gln Asn Trp Ser Gln Leu Pro Leu Leu Pro Lys Phe Asp Glu Val
                405                 410                 415

Tyr Ala Arg Ser Tyr Cys Phe Ser Ala Asn Tyr Ile Tyr His Leu Phe
                420                 425                 430

Val Asn Gly Tyr Lys Phe Thr Glu Glu Thr Trp Pro Gln Ile His Phe
                435                 440                 445

Glu Lys Glu Val Gly Asn Ser Ser Ile Ala Trp Ser Leu Gly Tyr Met
450                 455                 460
```

```
Leu Ser Leu Thr Asn Gln Ile Pro Ala Glu Ser Pro Leu Ile Arg Leu
465                 470                 475                 480

Pro Ile Glu Pro Pro Val Phe Val Gly Thr Leu Ala Phe Phe Thr Ala
            485                 490                 495

Ala Ala Leu Leu Cys Leu Ala Phe Leu Ala Tyr Leu Cys Ser Ala Thr
            500                 505                 510

Arg Arg Lys Arg His Ser Glu His Ala Phe Asp His Ala Val Asp Ser
        515                 520                 525

Asp

<210> SEQ ID NO 2
<211> LENGTH: 1590
<212> TYPE: DNA
<213> ORGANISM: Homo sapiens
<220> FEATURE:
<221> NAME/KEY: misc_feature
<222> LOCATION: (1)...(1590)
<223> OTHER INFORMATION: CD39L3

<400> SEQUENCE: 2
atggtcactg tgctgacccg ccaaccatgt gagcaagcag gcctcaaggc cctctaccga      60
actccaacca tcattgcctt ggtggtcttg cttgtgagta ttgtggtact tgtgagtatc     120
actgtcatcc agatccacaa gcaagaggtc ctccctccag gactgaagta tggtattgtg     180
ctggatgccg ggtcttcaag aaccacagtc tacgtgtatc aatggccagc agaaaaagag     240
aataataccg gagtggtcag tcaaaccttc aaatgtagtg tgaaaggctc tggaatctcc     300
agctatggaa ataacccca gatgtcccc agagcctttg aggagtgtat gcaaaaagtc     360
aaggggcagg ttccatccca cctccacgga tccaccccca ttcacctggg agccacggct     420
gggatgcgct tgctgaggtt gcaaaatgaa acagcagcta atgaagtcct tgaaagcatc     480
caaagctact tcaagtccca gcctttgac tttaggggtg ctcaaatcat ttctgggcaa     540
gaagaagggg tatatggatg gattacagcc aactatttaa tgggaaattt cctggagaag     600
aacctgtggc acatgtgggt gcacccgcat ggagtgaaa ccacgggtgc cctggactta     660
ggtggtgcct ccacccaaat atccttcgtg gcaggagaga gatggatct gaacaccagc     720 gacatcatgc aggtgtccct gtatggctac gtatacacgc tctacacaca cagcttccag     780
tgctatggcc ggaatgaggc tgagaagaag tttctggcaa tgctcctgca gaattctcct     840
accaaaaacc atctcaccaa tccctgttac cctcgggatt atagcatcag cttcaccatg     900
ggccatgtat ttgatagcct gtgcactgtg gaccagaggc agaaagtta taccccaat     960 gatgtcatca ctttgaagg aactgggac ccatctctgt gtaaggagaa ggtggcttcc    1020
atatttgact tcaaagcttg ccatgatcaa gaaacctgtt cttttgatgg ggtttatcag    1080
ccaaagatta aggggccatt tgtggctttt gcaggattct actacacagc cagtgcttta    1140
aatctttcag gtagcttttc cctggacacc ttcaactcca gcacctggaa tttctgctca    1200
cagaattgga gtcagctccc actgctgctc cccaaatttg atgaggtata tgcccgctct    1260
tactgcttct cagccaacta catctaccac ttgtttgtga acggttacaa attcacagag    1320
gagacttggc cccaaataca ctttgaaaaa gaagtgggga tagcagcat gcctggtct    1380 cttggctaca tgctcagcct gaccaaccag atcccagctg aaagccctct gatccgtctg    1440
cccatagaac cacctgtctt gtgggcacc ctcgctttct tcacagcggc agccttgctg    1500
tgtctggcat tccttgcata cctgtgttca gcaaccagaa gaaagaggca ctccgagcat    1560
```
gcctttgacc atgcagtgga ttctgactga                                        1590

<210> SEQ ID NO 3
<211> LENGTH: 444
<212> TYPE: PRT
<213> ORGANISM: Homo sapiens
<220> FEATURE:
<221> NAME/KEY: misc_feature
<222> LOCATION: (1)...(444)
<223> OTHER INFORMATION: Soluble CD39L3

<400> SEQUENCE: 3

```
Met Gln Ile His Lys Gln Glu Val Leu Pro Gly Leu Lys Tyr Gly
 1               5                  10                  15

Ile Val Leu Asp Ala Gly Ser Ser Arg Thr Thr Val Tyr Val Tyr Gln
                20                  25                  30

Trp Pro Ala Glu Lys Glu Asn Asn Thr Gly Val Val Ser Gln Thr Phe
            35                  40                  45

Lys Cys Ser Val Lys Gly Ser Gly Ile Ser Ser Tyr Gly Asn Asn Pro
50                  55                  60

Gln Asp Val Pro Arg Ala Phe Glu Glu Cys Met Gln Lys Val Lys Gly
65                  70                  75                  80

Gln Val Pro Ser His Leu His Gly Ser Thr Pro Ile His Leu Gly Ala
                85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Glu Gly Val Tyr Gly
130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
    210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
        275                 280                 285

Pro Ser Leu Cys Lys Glu Lys Val Ala Ser Ile Phe Asp Phe Lys Ala
    290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350
```

```
Thr Trp Asn Phe Cys Ser Gln Asn Trp Ser Gln Leu Pro Leu Leu Leu
        355                 360                 365

Pro Lys Phe Asp Glu Val Tyr Ala Arg Ser Tyr Cys Phe Ser Ala Asn
    370                 375                 380

Tyr Ile Tyr His Leu Phe Val Asn Gly Tyr Lys Phe Thr Glu Thr
385                 390                 395                 400

Trp Pro Gln Ile His Phe Glu Lys Glu Val Gly Asn Ser Ser Ile Ala
                405                 410                 415

Trp Ser Leu Gly Tyr Met Leu Ser Leu Thr Asn Gln Ile Pro Ala Glu
            420                 425                 430

Ser Pro Leu Ile Arg Leu Pro Ile Glu Pro Pro Val
        435                 440

<210> SEQ ID NO 4
<211> LENGTH: 1335
<212> TYPE: DNA
<213> ORGANISM: Homo sapiens
<220> FEATURE:
<221> NAME/KEY: misc_feature
<222> LOCATION: (1)...(1335)
<223> OTHER INFORMATION: Soluble CD39L3

<400> SEQUENCE: 4
atgcagatcc acaagcaaga ggtcctccct ccaggactga agtatggtat tgtgctggat      60
gccgggtctt caagaaccac agtctacgtg tatcaatggc agcagaaaa agagaataat     120 accggagtgg tcagtcaaac cttcaaatgt agtgtgaaag ctctggaat ctccagctat     180 ggaaataacc cccaagatgt ccccagagcc tttgaggagt gtatgcaaaa agtcaagggg     240
caggttccat cccacctcca cggatccacc cccattcacc tgggagccac ggctgggatg     300
cgcttgctga ggttgcaaaa tgaaacagca gctaatgaag tccttgaaag catccaaagc     360
tacttcaagt cccagccctt tgactttagg ggtgctcaaa tcatttctgg caagaagaa     420 ggggtatatg gatggattac agccaactat ttaatgggaa atttcctgga agagaacctg     480
tggcacatgt gggtgcaccc gcatggagtg gaaaccacgg tgccctgga cttaggtggt     540 gcctccaccc aaatatcctt cgtggcagga gagaagatgg atctgaacac cagcgacatc     600
atgcaggtgt ccctgtatgg ctacgtatac acgctctaca cacacagctt ccagtgctat     660
ggccggaatg aggctgagaa gagtttctg caatgctcc tgcagaattc tcctaccaaa     720
aaccatctca ccaatccctg ttaccctcgg gattatagca tcagcttcac catgggccat     780
gtatttgata gcctgtgcac tgtggaccag aggccagaaa gttataaccc caatgatgtc     840
atcacttttg aaggaactgg ggacccatct ctgtgtaagg agaaggtggc ttccatattt     900
gacttcaaag cttgccatga tcaagaaacc tgttctttg atggggttta tcagccaaag     960
attaaagggc catttgtggc ttttgcagga ttctactaca cagccagtgc tttaaatctt    1020
tcaggtagct tttcccctgga caccttcaac tccagcacct ggaatttctg ctcacagaat    1080
tggagtcagc tcccactgct gctccccaaa tttgatgagg tatatgcccg ctcttactgc    1140
ttctcagcca actacatcta ccacttgttt gtgaacggtt acaaattcac agaggagact    1200
tggccccaaa tacactttga aaagaagtg gggaatagca gcatagcctg gtctcttggc    1260
tacatgctca gcctgaccaa ccagatccca gctgaaagcc ctctgatccg tctgcccata    1320
gaaccacctg tctga                                                    1335

<210> SEQ ID NO 5
```

<211> LENGTH: 444
<212> TYPE: PRT
<213> ORGANISM: Homo sapiens
<220> FEATURE:
<221> NAME/KEY: misc_feature
<222> LOCATION: (1)...(444)
<223> OTHER INFORMATION: R67G T69R mutant of soluble CD39L3

<400> SEQUENCE: 5

```
Met Gln Ile His Lys Gln Glu Val Leu Pro Gly Leu Lys Tyr Gly
1               5                   10                  15

Ile Val Leu Asp Ala Gly Ser Ser Gly Thr Arg Val Tyr Val Tyr Gln
            20                  25                  30

Trp Pro Ala Glu Lys Glu Asn Asn Thr Gly Val Val Ser Gln Thr Phe
            35                  40                  45

Lys Cys Ser Val Lys Gly Ser Gly Ile Ser Ser Tyr Gly Asn Asn Pro
    50                  55                  60

Gln Asp Val Pro Arg Ala Phe Glu Glu Cys Met Gln Lys Val Lys Gly
65                  70                  75                  80

Gln Val Pro Ser His Leu His Gly Ser Thr Pro Ile His Leu Gly Ala
                85                  90                  95

Thr Ala Gly Met Arg Leu Leu Arg Leu Gln Asn Glu Thr Ala Ala Asn
            100                 105                 110

Glu Val Leu Glu Ser Ile Gln Ser Tyr Phe Lys Ser Gln Pro Phe Asp
        115                 120                 125

Phe Arg Gly Ala Gln Ile Ile Ser Gly Gln Glu Glu Gly Val Tyr Gly
130                 135                 140

Trp Ile Thr Ala Asn Tyr Leu Met Gly Asn Phe Leu Glu Lys Asn Leu
145                 150                 155                 160

Trp His Met Trp Val His Pro His Gly Val Glu Thr Thr Gly Ala Leu
                165                 170                 175

Asp Leu Gly Gly Ala Ser Thr Gln Ile Ser Phe Val Ala Gly Glu Lys
            180                 185                 190

Met Asp Leu Asn Thr Ser Asp Ile Met Gln Val Ser Leu Tyr Gly Tyr
        195                 200                 205

Val Tyr Thr Leu Tyr Thr His Ser Phe Gln Cys Tyr Gly Arg Asn Glu
    210                 215                 220

Ala Glu Lys Lys Phe Leu Ala Met Leu Leu Gln Asn Ser Pro Thr Lys
225                 230                 235                 240

Asn His Leu Thr Asn Pro Cys Tyr Pro Arg Asp Tyr Ser Ile Ser Phe
                245                 250                 255

Thr Met Gly His Val Phe Asp Ser Leu Cys Thr Val Asp Gln Arg Pro
            260                 265                 270

Glu Ser Tyr Asn Pro Asn Asp Val Ile Thr Phe Glu Gly Thr Gly Asp
        275                 280                 285

Pro Ser Leu Cys Lys Glu Lys Val Ala Ser Ile Phe Asp Phe Lys Ala
290                 295                 300

Cys His Asp Gln Glu Thr Cys Ser Phe Asp Gly Val Tyr Gln Pro Lys
305                 310                 315                 320

Ile Lys Gly Pro Phe Val Ala Phe Ala Gly Phe Tyr Tyr Thr Ala Ser
                325                 330                 335

Ala Leu Asn Leu Ser Gly Ser Phe Ser Leu Asp Thr Phe Asn Ser Ser
            340                 345                 350

Thr Trp Asn Phe Cys Ser Gln Asn Trp Ser Gln Leu Pro Leu Leu Leu
        355                 360                 365
```

-continued

Pro Lys Phe Asp Glu Val Tyr Ala Arg Ser Tyr Cys Phe Ser Ala Asn
        370                 375                 380

Tyr Ile Tyr His Leu Phe Val Asn Gly Tyr Lys Phe Thr Glu Glu Thr
385                 390                 395                 400

Trp Pro Gln Ile His Phe Glu Lys Glu Val Gly Asn Ser Ser Ile Ala
                405                 410                 415

Trp Ser Leu Gly Tyr Met Leu Ser Leu Thr Asn Gln Ile Pro Ala Glu
                420                 425                 430

Ser Pro Leu Ile Arg Leu Pro Ile Glu Pro Pro Val
        435                 440

<210> SEQ ID NO 6
<211> LENGTH: 1335
<212> TYPE: DNA
<213> ORGANISM: Homo sapiens
<220> FEATURE:
<221> NAME/KEY: misc_feature
<222> LOCATION: (1)...(1335)
<223> OTHER INFORMATION: R67G T69R mutant of soluble CD39L3

<400> SEQUENCE: 6
atgcagatcc acaagcaaga ggtcctccct ccaggactga agtatggtat tgtgctggat     60
gccgggtctt cagggacccg cgtctacgtg tatcaatggc agcagaaaaa agagaataat    120
accggagtgg tcagtcaaac cttcaaatgt agtgtgaaag ctctggaat ctccagctat     180 ggaaataacc cccaagatgt ccccagagcc tttgaggagt gtatgcaaaa agtcaagggg    240
caggttccat cccacctcca cggatccacc cccattcacc tgggagccac ggctgggatg    300
cgcttgctga ggttgcaaaa tgaaacagca gctaatgaag tccttgaaag catccaaagc    360
tacttcaagt cccagccctt tgactttagg ggtgctcaaa tcatttctgg caagaagaa     420 ggggtatatg atggagttac agccaactat ttaatgggaa atttcctgga agagaacctg    480
tggcacatgt gggtgcaccc gcatggagtg gaaaccacgg tgccctgga cttaggtggt     540 gcctccaccc aaatatcctt cgtggcagga gagaagatgg atctgaacac cagcgacatc    600
atgcaggtgt ccctgtatgg ctacgtatac acgctctaca cacacagctt ccagtgctat    660
ggccggaatg aggctgagaa aagtttctg caatgctcc tgcagaattc tcctaccaaa      720
aaccatctca ccaatccctg ttaccctcgg gattatagca tcagcttcac catgggccat    780
gtatttgata gcctgtgcac tgtggaccag aggccagaaa gttataaccc caatgatgtc    840 atcactttg aaggaactgg ggacccatct ctgtgtaagg agaaggtggc ttccatattt     900
gacttcaaag cttgccatga tcaagaaacc tgttcttttg atggggttta tcagccaaag    960
attaaagggc catttgtggc ttttgcagga ttctactaca cagccagtgc tttaaatctt   1020
tcaggtagct tttcctgga caccttcaac tccagcacct ggaatttctg ctcacagaat     1080
tggagtcagc tcccactgct gctccccaaa tttgatgagg tatatgcccg ctcttactgc   1140
ttctcagcca actacatcta ccacttgttt gtgaacggtt acaaattcac agaggagact   1200
tggccccaaa tacactttga aaaagaagtg gggaatagca gcatagcctg gtctcttggc   1260
tacatgctca gcctgaccaa ccagatccca gctgaaagcc ctctgatccg tctgcccata   1320
gaaccacctg tctga                                                    1335

<210> SEQ ID NO 7
<211> LENGTH: 469
<212> TYPE: PRT
<213> ORGANISM: Homo sapiens
<220> FEATURE:

<221> NAME/KEY: misc_feature
<222> LOCATION: (1)...(469)
<223> OTHER INFORMATION: HEK SOL CD39L3-01

<400> SEQUENCE: 7

```
Met Glu Thr Asp Thr Leu Leu Leu Trp Val Leu Leu Leu Trp Val Pro
 1               5                  10                  15

Gly Ser Thr Gly Asp Ala Pro Gly Pro Met Gln Ile His Lys Gln Glu
             20                  25                  30

Val Leu Pro Pro Gly Leu Lys Tyr Gly Ile Val Leu Asp Ala Gly Ser
         35                  40                  45

Ser Gly Thr Arg Val Tyr Val Tyr Gln Trp Pro Ala Glu Lys Glu Asn
 50                  55                  60

Asn Thr Gly Val Val Ser Gln Thr Phe Lys Cys Ser Val Lys Gly Ser
 65                  70                  75                  80

Gly Ile Ser Ser Tyr Gly Asn Asn Pro Gln Asp Val Pro Arg Ala Phe
             85                  90                  95

Glu Glu Cys Met Gln Lys Val Lys Gly Gln Val Pro Ser His Leu His
            100                 105                 110

Gly Ser Thr Pro Ile His Leu Gly Ala Thr Ala Gly Met Arg Leu Leu
        115                 120                 125

Arg Leu Gln Asn Glu Thr Ala Ala Asn Glu Val Leu Glu Ser Ile Gln
130                 135                 140

Ser Tyr Phe Lys Ser Gln Pro Phe Asp Phe Arg Gly Ala Gln Ile Ile
145                 150                 155                 160

Ser Gly Gln Glu Glu Gly Val Tyr Gly Trp Ile Thr Ala Asn Tyr Leu
            165                 170                 175

Met Gly Asn Phe Leu Glu Lys Asn Leu Trp His Met Trp Val His Pro
        180                 185                 190

His Gly Val Glu Thr Thr Gly Ala Leu Asp Leu Gly Gly Ala Ser Thr
    195                 200                 205

Gln Ile Ser Phe Val Ala Gly Glu Lys Met Asp Leu Asn Thr Ser Asp
210                 215                 220

Ile Met Gln Val Ser Leu Tyr Gly Tyr Val Tyr Thr Leu Tyr Thr His
225                 230                 235                 240

Ser Phe Gln Cys Tyr Gly Arg Asn Glu Ala Glu Lys Lys Phe Leu Ala
            245                 250                 255

Met Leu Leu Gln Asn Ser Pro Thr Lys Asn His Leu Thr Asn Pro Cys
        260                 265                 270

Tyr Pro Arg Asp Tyr Ser Ile Ser Phe Thr Met Gly His Val Phe Asp
    275                 280                 285

Ser Leu Cys Thr Val Asp Gln Arg Pro Glu Ser Tyr Asn Pro Asn Asp
290                 295                 300

Val Ile Thr Phe Glu Gly Thr Gly Asp Pro Ser Leu Cys Lys Glu Lys
305                 310                 315                 320

Val Ala Ser Ile Phe Asp Phe Lys Ala Cys His Asp Gln Glu Thr Cys
            325                 330                 335

Ser Phe Asp Gly Val Tyr Gln Pro Lys Ile Lys Gly Pro Phe Val Ala
        340                 345                 350

Phe Ala Gly Phe Tyr Tyr Thr Ala Ser Ala Leu Asn Leu Ser Gly Ser
    355                 360                 365

Phe Ser Leu Asp Thr Phe Asn Ser Ser Thr Trp Asn Phe Cys Ser Gln
370                 375                 380

Asn Trp Ser Gln Leu Pro Leu Leu Leu Pro Lys Phe Asp Glu Val Tyr
```

```
                385                 390                 395                 400
Ala Arg Ser Tyr Cys Phe Ser Ala Asn Tyr Ile Tyr His Leu Phe Val
                    405                 410                 415

Asn Gly Tyr Lys Phe Thr Glu Glu Thr Trp Pro Gln Ile His Phe Glu
                420                 425                 430

Lys Glu Val Gly Asn Ser Ser Ile Ala Trp Ser Leu Gly Tyr Met Leu
            435                 440                 445

Ser Leu Thr Asn Gln Ile Pro Ala Glu Ser Pro Leu Ile Arg Leu Pro
        450                 455                 460

Ile Glu Pro Asp Ile
465

<210> SEQ ID NO 8
<211> LENGTH: 1410
<212> TYPE: DNA
<213> ORGANISM: Homo sapiens
<220> FEATURE:
<221> NAME/KEY: misc_feature
<222> LOCATION: (1)...(1410)
<223> OTHER INFORMATION: HEK SOL CD39L3-01

<400> SEQUENCE: 8
atggagacag acacactcct gctatgggta ctgctgctct gggttccagg ttccactggt        60
gacgcgcccg ggccgatgca gatccacaag caagaggtcc tccctccagg actgaagtat      120
ggtattgtgc tggatgccgg gtcttcaggg accgcgtct acgtgtatca atggccagca       180
gaaaaagaga ataataccgg agtggtcagt caaaccttca atgtagtgt gaaaggctct       240 ggaatctcca gctatggaaa taaccccaa gatgtcccca gagcctttga ggagtgtatg       300
caaaaagtca gggggcaggt tccatcccac ctccacggat ccaccccat tcacctggga      360 gccacggctg ggatgcgctt gctgaggttg caaaatgaaa cagcagctaa tgaagtcctt       420
gaaagcatcc aaagctactt caagtcccag cccttttgact ttaggggtgc tcaaatcatt     480
tctgggcaag aagaaggggt atatggatgg attacagcca actatttaat gggaaatttc     540
ctggagaaga acctgtggca catgtgggtg cacccgcatg gagtggaaac cacgggtgcc     600
ctggacttag gtggtgcctc cacccaaata tccttcgtgg caggagagaa gatggatctg     660
aacaccagcg acatcatgca ggtgtccctg tatggctacg tatacacgct ctacacacac     720
agcttccagt gctatggccg aatgaggct gagaagaagt ttctggcaat gctcctgcag     780
aattctccta ccaaaaacca tctcaccaat ccctgttacc ctcgggatta tagcatcagc     840
ttcaccatgg gccatgtatt tgatagcctg tgcactgtgg accagaggcc agaaagttat     900
aaccccaatg atgtcatcac ttttgaagga actggggacc catctctgtg taaggagaag     960
gtggcttcca tatttgactt caaagcttgc catgatcaag aaacctgttc ttttgatggg    1020
gtttatcagc caaagattaa agggccattt gtggcttttg caggattcta ctacacagcc    1080
agtgctttaa atcttcagg tagcttttcc ctggacacct tcaactccag cacctggaat    1140
ttctgctcac agaattggag tcagctccca ctgctgctcc ccaaatttga tgaggtatat     1200
gcccgctctt actgcttctc agccaactac atctaccact tgtttgtgaa cggttacaaa    1260
ttcacagagg agacttggcc ccaaatacac tttgaaaaag aagtggggaa tagcagcata    1320
gcctggtctc ttggctacat gctcagcctg accaaccaga tcccagctga aagccctctg    1380
atccgtctgc ccatagaacc agatatctga                                     1410

<210> SEQ ID NO 9
```

-continued

<211> LENGTH: 457
<212> TYPE: PRT
<213> ORGANISM: Homo sapiens
<220> FEATURE:
<221> NAME/KEY: misc_feature
<222> LOCATION: (1)...(457)
<223> OTHER INFORMATION: EN-apyrase including signal

<400> SEQUENCE: 9

```
Met Met Ser Phe Val Ser Leu Leu Val Gly Ile Leu Phe His Ala
1               5                   10                  15

Thr Gln Ala Glu Val Leu Pro Pro Gly Leu Lys Tyr Gly Ile Val Leu
            20                  25                  30

Asp Ala Gly Ser Ser Gly Thr Arg Val Tyr Val Tyr Gln Trp Pro Ala
        35                  40                  45

Glu Lys Glu Asn Asn Thr Gly Val Val Ser Gln Thr Phe Lys Cys Ser
    50                  55                  60

Val Lys Gly Ser Gly Ile Ser Ser Tyr Gly Asn Asn Pro Gln Asp Val
65                  70                  75                  80

Pro Arg Ala Phe Glu Glu Cys Met Gln Lys Val Lys Gly Gln Val Pro
                85                  90                  95

Ser His Leu His Gly Ser Thr Pro Ile His Leu Gly Ala Thr Ala Gly
            100                 105                 110

Met Arg Leu Leu Arg Leu Gln Asn Glu Thr Ala Ala Asn Glu Val Leu
        115                 120                 125

Glu Ser Ile Gln Ser Tyr Phe Lys Ser Gln Pro Phe Asp Phe Arg Gly
130                 135                 140

Ala Gln Ile Ile Ser Gly Gln Glu Glu Gly Val Tyr Gly Trp Ile Thr
145                 150                 155                 160

Ala Asn Tyr Leu Met Gly Asn Phe Leu Glu Lys Asn Leu Trp His Met
                165                 170                 175

Trp Val His Pro His Gly Val Glu Thr Thr Gly Ala Leu Asp Leu Gly
            180                 185                 190

Gly Ala Ser Thr Gln Ile Ser Phe Val Ala Gly Glu Lys Met Asp Leu
        195                 200                 205

Asn Thr Ser Asp Ile Met Gln Val Ser Leu Tyr Gly Tyr Val Tyr Thr
210                 215                 220

Leu Tyr Thr His Ser Phe Gln Cys Tyr Gly Arg Asn Glu Ala Glu Lys
225                 230                 235                 240

Lys Phe Leu Ala Met Leu Leu Gln Asn Ser Pro Thr Lys Asn His Leu
                245                 250                 255

Thr Asn Pro Cys Tyr Pro Arg Asp Tyr Ser Ile Ser Phe Thr Met Gly
            260                 265                 270

His Val Phe Asp Ser Leu Cys Thr Val Asp Gln Arg Pro Glu Ser Tyr
        275                 280                 285

Asn Pro Asn Asp Val Ile Thr Phe Glu Gly Thr Gly Asp Pro Ser Leu
290                 295                 300

Cys Lys Glu Lys Val Ala Ser Ile Phe Asp Phe Lys Ala Cys His Asp
305                 310                 315                 320

Gln Glu Thr Cys Ser Phe Asp Gly Val Tyr Gln Pro Lys Ile Lys Gly
                325                 330                 335

Pro Phe Val Ala Phe Ala Gly Phe Tyr Tyr Thr Ala Ser Ala Leu Asn
            340                 345                 350

Leu Ser Gly Ser Phe Ser Leu Asp Thr Phe Asn Ser Ser Thr Trp Asn
        355                 360                 365
```

```
Phe Cys Ser Gln Asn Trp Ser Gln Leu Pro Leu Leu Leu Pro Lys Phe
    370                 375                 380
Asp Glu Val Tyr Ala Arg Ser Tyr Cys Phe Ser Ala Asn Tyr Ile Tyr
385                 390                 395                 400
His Leu Phe Val Asn Gly Tyr Lys Phe Thr Glu Glu Thr Trp Pro Gln
                405                 410                 415
Ile His Phe Glu Lys Glu Val Gly Asn Ser Ser Ile Ala Trp Ser Leu
            420                 425                 430
Gly Tyr Met Leu Ser Leu Thr Asn Gln Ile Pro Ala Glu Ser Pro Leu
        435                 440                 445
Ile Arg Leu Pro Ile Glu Pro Asp Ile
    450                 455
```

<210> SEQ ID NO 10
<211> LENGTH: 1374
<212> TYPE: DNA
<213> ORGANISM: Homo sapiens
<220> FEATURE:
<221> NAME/KEY: misc_feature
<222> LOCATION: (1)...(1374)
<223> OTHER INFORMATION: EN-apyrase construct including signal

<400> SEQUENCE: 10

```
atgatgtcct ttgtctctct gctcctggtt ggcatcctat tccatgccac ccaggccgag     60
gtcctccctc caggactgaa gtatggtatt gtgctggatg ccgggtcttc agggacccgc    120
gtctacgtgt atcaatggcc agcagaaaaa gagaataata ccggagtggt cagtcaaacc    180
ttcaaatgta gtgtgaaagg ctctggaatc tccagctatg aaataacccc caagatgtc    240
cccagagcct tgaggagtg tatgcaaaaa gtcaaggggc aggttccatc ccacctccac    300
ggatccaccc ccattcacct gggagccacg gctgggatgc gcttgctgag gttgcaaaat    360
gaaacagcag ctaatgaagt ccttgaaagc atccaaagct acttcaagtc ccagcccttt    420
gactttaggg gtgctcaaat catttctggg caagaagaag gggtatatgg atggattaca    480
gccaactatt taatgggaaa tttcctggag aagaacctgt ggcacatgtg ggtgcacccg    540
catggagtga aaaccacggg tgccctggac ttaggtggtg cctccaccca aatatccttc    600
gtggcaggag agaagatgga tctgaacacc agcgacatca tgcaggtgtc cctgtatggc    660
tacgtataca cgctctacac acacagcttc cagtgctatg ccggaatgaa ggctgagaag    720
aagtttctgg caatgctcct gcagaattct cctaccaaaa accatctcac caatccctgt    780
tacccctcggg attatagcat cagcttcacc atgggccatg tatttgatag cctgtgcact    840
gtggaccaga ggccagaaag ttataacccc aatgatgtca tcacttttga aggaactggg    900
gacccatctc tgtgtaagga aaggtggct tccatatttg acttcaaagc ttgccatgat    960
caagaaacct gttcttttga tggggtttat cagccaaaga ttaaagggcc atttgtggct   1020
tttgcaggat tctactacac agccagtgct ttaaatcttt caggtagctt ttccctggac   1080
accttcaact ccagcacctg gaatttctgc tcacagaatt ggagtcagct cccactgctg   1140
ctccccaaat tgatgaggt atatgcccgc tcttactgct ctcagccaa ctacatctac   1200
cacttgtttg tgaacggtta caaattcaca gaggagactt ggccccaaat cactttgaa   1260
aaagaagtgg ggaatagcag catagcctgg tctcttggct acatgctcag cctgaccaac   1320
cagatcccag ctgaaagccc tctgatccgt ctgcccatag aaccagatat ctga          1374
```

<210> SEQ ID NO 11
<211> LENGTH: 365

```
<212> TYPE: PRT
<213> ORGANISM: Homo sapiens
<220> FEATURE:
<221> NAME/KEY: misc_feature
<222> LOCATION: (1)...(365)
<223> OTHER INFORMATION: 1A02_HUMAN (P01892)

<400> SEQUENCE: 11
```

| | | | | | | | | | | | | | | |
|---|---|---|---|---|---|---|---|---|---|---|---|---|---|---|
|Met|Ala|Val|Met|Ala|Pro|Arg|Thr|Leu|Val|Leu|Leu|Leu|Ser|Gly|Ala|
|1| | | |5| | | | |10| | | | |15|

Met Ala Val Met Ala Pro Arg Thr Leu Val Leu Leu Leu Ser Gly Ala
 1               5                  10                  15

Leu Ala Leu Thr Gln Thr Trp Ala Gly Ser His Ser Met Arg Tyr Phe
             20                  25                  30

Phe Thr Ser Val Ser Arg Pro Gly Arg Gly Glu Pro Arg Phe Ile Ala
         35                  40                  45

Val Gly Tyr Val Asp Asp Thr Gln Phe Val Arg Phe Asp Ser Asp Ala
 50                  55                  60

Ala Ser Gln Arg Met Glu Pro Arg Ala Pro Trp Ile Glu Gln Glu Gly
 65              70                  75                  80

Pro Glu Tyr Trp Asp Gly Glu Thr Arg Lys Val Lys Ala His Ser Gln
             85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
            115                 120                 125

Ser Asp Trp Arg Phe Leu Arg Gly Tyr His Gln Tyr Ala Tyr Asp Gly
            130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

-continued

```
<210> SEQ ID NO 12
<211> LENGTH: 613
<212> TYPE: PRT
<213> ORGANISM: Bos taurus
<220> FEATURE:
<221> NAME/KEY: misc_feature
<222> LOCATION: (1)...(613)
<223> OTHER INFORMATION: ACES_BOVIN (P23795)

<400> SEQUENCE: 12
```

Met Arg Pro Pro Trp Cys Pro Leu His Thr Pro Ser Leu Thr Pro Pro
1               5                   10                  15

Leu Leu Leu Leu Leu Phe Leu Ile Gly Gly Ala Glu Ala Glu Gly
            20                  25                  30

Pro Glu Asp Pro Glu Leu Leu Val Met Val Arg Gly Gly Arg Leu Arg
                35                  40                  45

Gly Leu Arg Leu Met Ala Pro Arg Gly Pro Val Ser Ala Phe Leu Gly
    50                  55                  60

Ile Pro Phe Ala Glu Pro Pro Val Gly Pro Arg Arg Phe Leu Pro Pro
65                  70                  75                  80

Glu Pro Lys Arg Pro Trp Pro Gly Val Leu Asn Ala Thr Ala Phe Gln
                85                  90                  95

Ser Val Cys Tyr Gln Tyr Val Asp Thr Leu Tyr Pro Gly Phe Glu Gly
            100                 105                 110

Thr Glu Met Trp Asn Pro Asn Arg Glu Leu Ser Glu Asp Cys Leu Tyr
        115                 120                 125

Leu Asn Val Trp Thr Pro Tyr Pro Arg Pro Ser Ser Pro Thr Pro Val
    130                 135                 140

Leu Val Trp Ile Tyr Gly Gly Gly Phe Tyr Ser Gly Ala Ser Ser Leu
145                 150                 155                 160

Asp Val Tyr Asp Gly Arg Phe Leu Thr Gln Ala Glu Gly Thr Val Leu
                165                 170                 175

Val Ser Met Asn Tyr Arg Val Gly Ala Phe Gly Phe Leu Ala Leu Pro
            180                 185                 190

Gly Ser Arg Glu Ala Pro Gly Asn Val Gly Leu Leu Asp Gln Arg Leu
        195                 200                 205

Ala Leu Gln Trp Val Gln Glu Asn Val Ala Ala Phe Gly Gly Asp Pro
    210                 215                 220

Thr Ser Val Thr Leu Phe Gly Glu Ser Ala Gly Ala Ala Ser Val Gly
225                 230                 235                 240

Met His Leu Leu Ser Pro Pro Ser Arg Gly Leu Phe His Arg Ala Val
                245                 250                 255

Leu Gln Ser Gly Ala Pro Asn Gly Pro Trp Ala Thr Val Gly Val Gly
            260                 265                 270

Glu Ala Arg Arg Arg Ala Thr Leu Leu Ala Arg Leu Val Gly Cys Pro
        275                 280                 285

Pro Gly Gly Ala Gly Gly Asn Asp Thr Glu Leu Val Ala Cys Leu Arg
    290                 295                 300

Ala Arg Pro Ala Gln Asp Leu Val Asp His Glu Trp Arg Val Leu Pro
305                 310                 315                 320

Gln Glu Ser Val Phe Arg Phe Ser Phe Val Pro Val Val Asp Gly Asp
                325                 330                 335

Phe Leu Ser Asp Thr Pro Glu Ala Leu Ile Asn Ala Gly Asp Phe His
            340                 345                 350

Gly Leu Gln Val Leu Val Gly Val Val Lys Asp Glu Gly Ser Tyr Phe
        355                 360                 365

-continued

```
Leu Val Tyr Gly Ala Pro Gly Phe Ser Lys Asp Asn Glu Ser Leu Ile
            370                 375                 380

Ser Arg Ala Gln Phe Leu Ala Gly Val Arg Val Gly Val Pro Gln Ala
385                 390                 395                 400

Ser Asp Leu Ala Ala Glu Ala Val Val Leu His Tyr Thr Asp Trp Leu
                405                 410                 415

His Pro Glu Asp Pro Ala Arg Leu Arg Glu Ala Leu Ser Asp Val Val
            420                 425                 430

Gly Asp His Asn Val Val Cys Pro Val Ala Gln Leu Ala Gly Arg Leu
        435                 440                 445

Ala Ala Gln Gly Ala Arg Val Tyr Ala Tyr Ile Phe Glu His Arg Ala
450                 455                 460

Ser Thr Leu Ser Trp Pro Leu Trp Met Gly Val Pro His Gly Tyr Glu
465                 470                 475                 480

Ile Glu Phe Ile Phe Gly Leu Pro Leu Glu Pro Ser Leu Asn Tyr Thr
                485                 490                 495

Ile Glu Glu Arg Thr Phe Ala Gln Arg Leu Met Arg Tyr Trp Ala Asn
            500                 505                 510

Phe Ala Arg Thr Gly Asp Pro Asn Asp Pro Arg Asp Pro Lys Ala Pro
        515                 520                 525

Gln Trp Pro Pro Tyr Thr Ala Gly Ala Gln Gln Tyr Val Ser Leu Asn
530                 535                 540

Leu Arg Pro Leu Glu Val Arg Arg Gly Leu Arg Ala Gln Ala Cys Ala
545                 550                 555                 560

Phe Trp Asn Arg Phe Leu Pro Lys Leu Leu Ser Ala Thr Asp Thr Leu
                565                 570                 575

Asp Glu Ala Glu Arg Gln Trp Lys Ala Glu Phe His Arg Trp Ser Ser
            580                 585                 590

Tyr Met Val His Trp Lys Asn Gln Phe Asp His Tyr Ser Lys Gln Asp
        595                 600                 605

Arg Cys Ser Asp Leu
    610
```

```
<210> SEQ ID NO 13
<211> LENGTH: 1304
<212> TYPE: PRT
<213> ORGANISM: Pan troglodytes
<220> FEATURE:
<221> NAME/KEY: misc_feature
<222> LOCATION: (1)...(1304)
<223> OTHER INFORMATION: ACE_PANTR (Q9GLN7)

<400> SEQUENCE: 13

Met Gly Ala Ala Ser Gly Arg Arg Gly Pro Gly Leu Leu Leu Pro Leu
1               5                   10                  15

Leu Leu Leu Leu Pro Pro Gln Pro Ala Leu Ala Leu Asp Pro Gly Leu
                20                  25                  30

Gln Pro Gly Asn Phe Ser Ala Asp Glu Ala Gly Ala Gln Leu Phe Ala
            35                  40                  45

Gln Ser Tyr Asn Ser Ser Ala Glu Gln Val Leu Phe Gln Ser Val Ala
        50                  55                  60

Ala Ser Trp Ala His Asp Thr Asn Ile Thr Ala Glu Asn Ala Arg Arg
65                  70                  75                  80

Gln Glu Glu Ala Ala Leu Leu Ser Gln Glu Phe Ala Glu Ala Trp Gly
                85                  90                  95
```

```
Gln Lys Ala Lys Glu Leu Tyr Glu Pro Val Trp Gln Asn Phe Thr Asp
            100                 105                 110

Pro Gln Leu Arg Arg Ile Ile Gly Ala Val Arg Thr Leu Gly Ser Ala
        115                 120                 125

Asn Leu Pro Leu Ala Lys Arg Gln Gln Tyr Asn Ala Leu Leu Ser Asn
    130                 135                 140

Met Ser Arg Ile Tyr Ser Thr Ala Lys Val Cys Leu Pro Asn Lys Thr
145                 150                 155                 160

Ala Thr Cys Trp Ser Leu Asp Pro Asp Leu Thr Asn Ile Leu Ala Ser
                165                 170                 175

Ser Arg Ser Tyr Ala Met Leu Leu Phe Ala Trp Glu Gly Trp His Asn
        180                 185                 190

Ala Ala Gly Ile Pro Leu Lys Pro Leu Tyr Glu Asp Phe Thr Ala Leu
    195                 200                 205

Ser Asn Glu Ala Tyr Lys Gln Asp Gly Phe Thr Asp Thr Gly Ala Tyr
    210                 215                 220

Trp Arg Ser Trp Tyr Asn Ser Pro Thr Phe Glu Asp Asp Leu Glu His
225                 230                 235                 240

Leu Tyr Gln Gln Leu Glu Pro Leu Tyr Leu Asn Leu His Ala Phe Val
                245                 250                 255

Arg Arg Ala Leu His Arg Arg Tyr Gly Asp Arg Tyr Ile Asn Leu Arg
        260                 265                 270

Gly Pro Ile Pro Ala His Leu Leu Gly Asp Met Trp Ala Gln Ser Trp
    275                 280                 285

Glu Asn Ile Tyr Asp Met Val Val Pro Phe Pro Asp Lys Pro Asn Leu
    290                 295                 300

Asp Val Thr Ser Thr Met Leu Gln Gln Gly Trp Asn Ala Thr His Met
305                 310                 315                 320

Phe Arg Val Ala Glu Glu Phe Phe Thr Ser Leu Glu Leu Ser Pro Met
                325                 330                 335

Pro Pro Glu Phe Trp Glu Gly Ser Met Leu Glu Lys Pro Ala Asp Gly
        340                 345                 350

Arg Glu Val Val Cys His Ala Ser Ala Trp Asp Phe Tyr Asn Arg Lys
    355                 360                 365

Asp Phe Arg Ile Lys Gln Cys Thr Arg Val Thr Met Asp Gln Leu Ser
    370                 375                 380

Thr Val His His Glu Met Gly His Ile Gln Tyr Tyr Leu Gln Tyr Lys
385                 390                 395                 400

Asp Leu Pro Val Ser Leu Arg Gly Gly Ala Asn Pro Gly Phe His Glu
                405                 410                 415

Ala Ile Gly Asp Val Leu Ala Leu Ser Val Ser Thr Pro Ala His Leu
        420                 425                 430

His Lys Ile Gly Leu Leu Asp Asn Val Thr Asn Asp Thr Glu Ser Asp
    435                 440                 445

Ile Asn Tyr Leu Leu Lys Met Ala Leu Glu Lys Ile Ala Phe Leu Pro
    450                 455                 460

Phe Gly Tyr Leu Val Asp Gln Trp Arg Trp Gly Val Phe Ser Gly Arg
465                 470                 475                 480

Thr Pro Asn Ser Arg Tyr Asn Phe Asp Trp Trp Tyr Leu Arg Thr Lys
                485                 490                 495

Tyr Gln Gly Ile Cys Pro Pro Val Thr Arg Asn Glu Thr His Phe Asp
        500                 505                 510

Ala Gly Ala Lys Phe His Val Pro Asn Val Thr Pro Tyr Ile Arg Tyr
```

```
            515                 520                 525
    Phe Val Ser Phe Val Leu Gln Phe Gln Phe His Glu Ala Leu Cys Lys
            530                 535                 540
    Glu Ala Gly Tyr Glu Gly Pro Leu His Gln Cys Asp Ile Tyr Gln Ser
545                 550                 555                 560
    Thr Lys Ala Gly Ala Lys Leu Arg Lys Val Leu Gln Ala Gly Ser Ser
                565                 570                 575
    Arg Pro Trp Gln Glu Val Leu Lys Asp Met Val Gly Leu Asp Ala Leu
                580                 585                 590
    Asp Ala Gln Pro Leu Leu Lys Tyr Phe Gln Pro Val Thr Gln Trp Leu
                595                 600                 605
    Gln Glu Gln Asn Gln Gln Asn Gly Glu Val Leu Gly Trp Pro Glu Tyr
            610                 615                 620
    Gln Trp His Pro Pro Leu Pro Asp Asn Tyr Pro Glu Gly Ile Asp Leu
625                 630                 635                 640
    Val Thr Asp Glu Ala Glu Ala Ser Lys Phe Val Glu Glu Tyr Asp Arg
                645                 650                 655
    Thr Ser Gln Val Val Trp Asn Glu Tyr Ala Glu Ala Asn Trp Asn Tyr
                660                 665                 670
    Asn Thr Asn Ile Thr Thr Glu Thr Ser Lys Ile Leu Leu Gln Lys Asn
                675                 680                 685
    Met Gln Ile Ala Asn His Thr Leu Lys Tyr Gly Thr Gln Ala Arg Arg
            690                 695                 700
    Phe Asp Val Asn Gln Leu Gln Asn Thr Thr Ile Lys Arg Ile Ile Lys
705                 710                 715                 720
    Lys Val Gln Asp Leu Glu Arg Ala Ala Leu Pro Ala Gln Glu Leu Glu
                725                 730                 735
    Glu Tyr Asn Lys Ile Leu Leu Asp Met Glu Thr Thr Tyr Ser Val Ala
                740                 745                 750
    Thr Val Cys His Thr Asn Gly Ser Cys Leu Gln Leu Glu Pro Asp Leu
                755                 760                 765
    Thr Asn Val Met Ala Thr Ser Arg Lys Tyr Glu Asp Leu Leu Trp Ala
            770                 775                 780
    Trp Glu Gly Trp Arg Asp Lys Ala Gly Arg Ala Ile Leu Gln Phe Tyr
785                 790                 795                 800
    Pro Lys Tyr Val Glu Leu Ile Asn Gln Ala Ala Arg Leu Asn Gly Tyr
                805                 810                 815
    Val Asp Ala Gly Asp Ser Trp Arg Ser Met Tyr Glu Thr Pro Ser Leu
                820                 825                 830
    Glu Gln Asp Leu Glu Arg Leu Phe Gln Glu Leu Gln Pro Leu Tyr Leu
                835                 840                 845
    Asn Leu His Ala Tyr Val Arg Arg Ala Leu His Arg His Tyr Gly Ala
            850                 855                 860
    Gln His Ile Asn Leu Glu Gly Pro Ile Pro Ala His Leu Leu Gly Asn
865                 870                 875                 880
    Met Trp Ala Gln Thr Trp Ser Asn Ile Tyr Asp Leu Val Val Pro Phe
                885                 890                 895
    Pro Ser Ala Pro Ser Met Asp Thr Thr Glu Ala Met Leu Lys Gln Gly
                900                 905                 910
    Trp Thr Pro Arg Arg Met Phe Lys Glu Ala Asp Asp Phe Phe Thr Ser
                915                 920                 925
    Leu Gly Leu Leu Pro Val Pro Pro Glu Phe Trp Asn Lys Ser Met Leu
            930                 935                 940
```

Glu Lys Pro Thr Asp Gly Arg Glu Val Val Cys His Ala Ser Ala Trp
945                 950                 955                 960

Asp Phe Tyr Asn Gly Lys Asp Phe Arg Ile Lys Gln Cys Thr Thr Val
                965                 970                 975

Asn Leu Glu Asp Leu Val Val Ala His His Glu Met Gly His Ile Gln
            980                 985                 990

Tyr Phe Met Gln Tyr Lys Asp Leu Pro Val Ala Leu Arg Glu Gly Ala
        995                 1000                1005

Asn Pro Gly Phe His Glu Ala Ile Gly Asp Val Leu Ala Leu Ser Val
    1010                1015                1020

Ser Thr Pro Lys His Leu His Ser Leu Asn Leu Leu Ser Glu Gly
1025                1030                1035                1040

Gly Ser Asp Glu His Asp Ile Asn Phe Leu Met Lys Met Ala Leu Asp
                1045                1050                1055

Lys Ile Ala Phe Ile Pro Phe Ser Tyr Leu Val Asp Gln Trp Arg Trp
            1060                1065                1070

Arg Val Phe Asp Gly Ser Ile Thr Lys Glu Asn Tyr Asn Gln Glu Trp
        1075                1080                1085

Trp Ser Leu Arg Leu Lys Tyr Gln Gly Leu Cys Pro Pro Val Pro Arg
    1090                1095                1100

Thr Gln Gly Asp Phe Asp Pro Gly Ala Lys Phe His Ile Pro Ser Ser
1105                1110                1115                1120

Val Pro Tyr Ile Arg Tyr Phe Val Ser Phe Ile Ile Gln Phe Gln Phe
                1125                1130                1135

His Glu Ala Leu Cys Gln Ala Ala Gly His Thr Gly Pro Leu His Lys
            1140                1145                1150

Cys Asp Ile Tyr Gln Ser Lys Glu Ala Gly Gln Arg Leu Ala Thr Ala
        1155                1160                1165

Met Lys Leu Gly Phe Ser Arg Pro Trp Pro Glu Ala Met Gln Leu Ile
    1170                1175                1180

Thr Gly Gln Pro Asn Met Ser Ala Ser Ala Met Leu Ser Tyr Phe Lys
1185                1190                1195                1200

Pro Leu Leu Asp Trp Leu Arg Thr Glu Asn Glu Leu His Gly Glu Lys
                1205                1210                1215

Leu Gly Trp Pro Gln Tyr Asn Trp Thr Pro Asn Ser Ala Arg Ser Glu
            1220                1225                1230

Gly Pro Leu Pro Asp Ser Gly Arg Val Ser Phe Leu Gly Leu Asp Leu
        1235                1240                1245

Asp Ala Gln Gln Ala Arg Val Gly Gln Trp Leu Leu Leu Phe Leu Gly
    1250                1255                1260

Ile Ala Leu Leu Val Ala Thr Leu Gly Leu Ser Gln Arg Leu Phe Ser
1265                1270                1275                1280

Ile Arg His Arg Ser Leu His Arg His Ser His Gly Pro Gln Phe Asp
                1285                1290                1295

Ser Glu Val Glu Leu Arg His Ser
            1300

<210> SEQ ID NO 14
<211> LENGTH: 756
<212> TYPE: PRT
<213> ORGANISM: Macaca fascicularis
<220> FEATURE:
<221> NAME/KEY: misc_feature
<222> LOCATION: (1)...(756)
<223> OTHER INFORMATION: ADAM5_MACFA (Q28483)

```
<400> SEQUENCE: 14

Met Phe Leu Leu Leu Val Leu Leu Thr Gly Leu Gly Gly Met His Ala
 1               5                   10                  15

Asp Leu Asn Pro His Lys Thr Phe Leu Gln Thr Thr Ile Pro Glu Lys
             20                  25                  30

Ile Ser Ser Ser Asp Ala Lys Thr Asp Pro Glu His Asn Val Val Tyr
         35                  40                  45

Met Ile Thr Ile Glu Gly Lys Pro Tyr Phe Val His Leu Lys Lys Gln
 50                  55                  60

Ser Ile Leu Ser Ser Ala Ser Phe Ile His Ser Tyr Asp Lys Asn Asp
65                  70                  75                  80

Ile Arg His Ser Lys Pro Leu Leu Val Gln Met Asp Cys Asn Tyr Asn
                 85                  90                  95

Gly Tyr Val Ala Gly Ile Pro Asn Ser Leu Val Thr Leu Ser Val Cys
            100                 105                 110

Ser Gly Leu Arg Gly Thr Met Gln Leu Lys Asn Ile Ser Tyr Gly Ile
            115                 120                 125

Glu Pro Met Glu Ala Val Ser Gly Phe Ile His Lys Ile Tyr Glu Glu
130                 135                 140

Lys Phe Ala Asp Thr Asn Ile Leu Leu Glu Glu Asn Asp Thr Tyr Ser
145                 150                 155                 160

Trp Phe Asn Ser Glu Tyr Gln Val Arg Lys Ser Ser Glu Lys Thr Asp
                165                 170                 175

Phe Ile Lys Leu Phe Pro Arg Tyr Ile Glu Met His Ile Val Val Asp
            180                 185                 190

Lys Asn Leu Phe Asp Tyr Met Gly Ser Asp Ile Asn Ala Val Thr Gln
            195                 200                 205

Lys Val Ile Gln Ile Ile Gly Leu Val Asn Thr Met Leu Thr Gln Leu
210                 215                 220

Gln Leu Thr Val Ile Ile Ser Ser Ile Glu Ile Trp Ser Asn Lys Asn
225                 230                 235                 240

Lys Ile Ser Thr Thr Gly His Ala Glu Tyr Val Leu Leu Glu Phe Phe
                245                 250                 255

Glu Trp Lys Lys Asp His Leu Asn Phe Lys Pro His Gln Ile Ala Tyr
            260                 265                 270

Leu Phe Val Tyr Arg Lys Leu Pro Thr Leu Ile Gly Ala Thr Phe Pro
            275                 280                 285

Gly Gln Val Cys Asn Lys Asp Phe Ala Ala Val Ala Leu Tyr Pro
290                 295                 300

Glu Gly Leu Ser Leu Glu Ser Tyr Thr Val Ile Ile Val Gln Leu Leu
305                 310                 315                 320

Gly Leu Asn Leu Gly Leu Thr Tyr Asp Lys Thr Asp Thr Cys His Cys
                325                 330                 335

Ser Gly Asp Val Cys Thr Met Thr Pro Lys Ala Val Tyr Ser Gly Gly
            340                 345                 350

Val Lys Asp Phe Ser Val Cys Ser Leu Asp Asp Phe Lys Tyr Ile Ser
            355                 360                 365

Ser His Asn Gly Leu Thr Cys Leu Gln Thr Asn Pro Leu Glu Met Pro
            370                 375                 380

Thr Tyr Thr Gln Arg Arg Ile Cys Gly Asn Gly Leu Leu Glu Gly Gly
385                 390                 395                 400

Glu Glu Cys Asp Cys Gly Asn Lys Asp Asn Cys Thr His Lys Leu Cys
```

```
                     405                 410                 415

Cys Asp Ala Leu Thr Cys Arg Leu Lys Asp Asn Ala Gln Cys Gly Ser
            420                 425                 430

Gly Asp Cys Cys Ser Lys Asp Cys Lys Phe Lys Pro Ala Asn Thr Ile
        435                 440                 445

Cys Arg Lys Ser Val Asp Val Glu Cys Asp Phe Thr Glu Phe Cys Asn
    450                 455                 460

Gly Ser Tyr Pro Tyr Cys Leu Leu Asp Thr Tyr Val Arg Asp Gly Glu
465                 470                 475                 480

Tyr Cys Asp Ser Gly Gly Ala Phe Cys Phe Gln Gly Arg Cys Arg Thr
                485                 490                 495

Phe Asp Lys Gln Cys Asp Asp Leu Ile Gly Arg Gly Ser Arg Gly Ala
            500                 505                 510

Pro Ile Phe Cys Tyr Asp Glu Ile Asn Thr Arg Gly Asp Lys Phe Gly
        515                 520                 525

Asn Cys Gly Thr Glu Tyr Cys Leu Phe Gln His Ile Leu Cys Gly Lys
    530                 535                 540

Leu Val Cys Thr Trp Glu His Lys Asp Leu Ile Ser Arg Pro Asn Leu
545                 550                 555                 560

Ser Val Ile Tyr Ala His Val Arg Asp Gln Thr Cys Val Ser Thr Tyr
                565                 570                 575

Leu Pro Ser Arg Lys Pro Pro Val Ala Ser Thr Val Ser Lys Thr
            580                 585                 590

Ser Tyr Tyr Ser Val Asp Asp Arg Asp Glu Thr Phe Val Gln Asp Gly
        595                 600                 605

Ser Val Cys Gly Pro Asp Met Tyr Cys Phe Lys Met Arg Cys Lys His
    610                 615                 620

Val Arg Phe Leu Met Asp Phe Glu Thr Cys Glu Ala Ser Ile Glu Cys
625                 630                 635                 640

Ser Gly His Gly Ile Cys Asn Asn Phe Asn His Cys His Cys Glu Lys
                645                 650                 655

Gly Tyr Asn Pro Pro His Cys Lys Pro Lys Lys Glu Ala Phe Gly Ser
            660                 665                 670

Thr Asp Asp Gly His Leu Val Pro Ala Glu Lys Ser Tyr Met Glu Glu
        675                 680                 685

Gly Arg His Ala Pro Phe Gln Lys Gln Arg Phe Gln Leu Ile Phe Tyr
    690                 695                 700

Ile Ser Leu Pro Val Leu Ile Ile Thr Thr Ala Ile Leu Ile Lys Arg
705                 710                 715                 720

Lys Lys Leu Arg Glu Leu Cys Tyr Arg Gly Glu Thr Glu Ser Glu Ser
                725                 730                 735

Ser Val Ser Gln Glu Ser Ser Ser Asn Ser Lys Ser Ser Leu Ser Glu
            740                 745                 750

Ser Thr Ser Leu
            755

<210> SEQ ID NO 15
<211> LENGTH: 1228
<212> TYPE: PRT
<213> ORGANISM: Mus muscularis
<220> FEATURE:
<221> NAME/KEY: misc_feature
<222> LOCATION: (1)...(1228)
<223> OTHER INFORMATION: AEGP_MOUSE (A2AJA7)

<400> SEQUENCE: 15
```

-continued

```
Met Cys Leu Pro Ser His Leu Ser Thr Trp Val Leu Phe Met Ala
1               5                   10                  15

Ala Gln Ser Leu Gly Lys Thr Trp Leu Pro Asn His Cys Arg Ser Pro
            20                  25                  30

Ile Lys Ala Val Cys Asn Phe Val Cys Asp Cys Gly Asp Cys Ser Asp
            35                  40                  45

Glu Thr Gln Cys Gly Phe His Gly Ala Ser Thr Ile Pro Ser Thr Ser
        50                  55                  60

Phe Thr Cys Asn Phe Glu Gln Asp Ser Cys Gly Trp Gln Asp Ile Ser
65                  70                  75                  80

Thr Ser Gly Tyr Arg Trp Leu Arg Asp Arg Ala Gly Ala Val Leu His
                85                  90                  95

Gly Pro Gly Pro His Ser Asp His Thr His Gly Thr Asp Leu Gly Trp
                100                 105                 110

Tyr Met Ala Val Gly Thr His Ser Gly Lys Glu Pro Ser Thr Ala Thr
            115                 120                 125

Leu Arg Ser Pro Val Met Arg Glu Ala Ala Pro Thr Cys Glu Leu Arg
        130                 135                 140

Leu Trp Tyr His Ile Ala Ser Arg Asp Val Ala Glu Leu Arg Leu Asp
145                 150                 155                 160

Leu Thr His Gly Val Glu Thr Leu Thr Leu Trp Gln Thr Ser Gly Pro
                165                 170                 175

Trp Gly Pro Gly Trp Gln Glu Leu Ala Val Asn Thr Gly Arg Ile Gln
                180                 185                 190

Gly Asp Phe Lys Val Thr Phe Ser Ala Thr Arg Asn Ala Thr His Arg
            195                 200                 205

Gly Ala Val Ala Leu Asp Asp Val Glu Phe Arg Asp Cys Gly Leu Pro
        210                 215                 220

Ile Pro Gln Ala Arg Cys Pro Leu Gly His His Cys Gln Asn Lys
225                 230                 235                 240

Ala Cys Val Glu Pro His Gln Leu Cys Asp Gly Glu Asp Asn Cys Gly
                245                 250                 255

Asp Arg Ser Asp Glu Asp Pro Leu Ile Cys Ser His His Met Ala Thr
            260                 265                 270

Asp Phe Glu Thr Gly Leu Gly Pro Trp Asn Gln Leu Glu Gly Trp Thr
        275                 280                 285

Arg Asn His Ser Ala Gly Ser Met Val Ser Pro Ala Trp Pro His Arg
        290                 295                 300

Asp His Ser Arg Asn Ser Ala Tyr Gly Phe Phe Leu Ile Ser Val Ala
305                 310                 315                 320

Lys Pro Gly Thr Thr Ala Val Leu Tyr Ser Pro Glu Phe Gln Gly Ser
                325                 330                 335

Val Ser Asn Asn Cys Ser Phe Thr Phe Tyr Tyr Tyr Leu His Gly Ser
            340                 345                 350

Glu Ala Ser His Phe Gln Leu Phe Leu Gln Ala Gln Gly Leu Asn Thr
        355                 360                 365

Pro Gln Val Pro Val Leu Leu Arg Ser Arg His Gly Glu Leu Gly Thr
    370                 375                 380

Ala Trp Val Arg Asp Arg Val Asp Ile Gln Ser Ala His Pro Phe Arg
385                 390                 395                 400

Ile Leu Leu Ala Gly Glu Thr Gly Pro Gly Val Val Gly Leu Asp
                405                 410                 415
```

```
Asp Leu Ile Met Ser Ser His Cys Met Leu Val Pro Ala Met Ser Thr
                420                 425                 430

Leu Gln Ser Ser Leu Ser Gly Pro Val Pro Leu Ala Leu Tyr Pro Gln
        435                 440                 445

Thr Ser Ile Lys Leu Pro Gln Gln Thr Cys Glu Pro Gly His Leu Ser
        450                 455                 460

Cys Gly Asp Leu Cys Val Pro Pro Glu Gln Leu Cys Asp Phe Gln Lys
465                 470                 475                 480

His Cys Ala Glu Gly Glu Asp Glu His Lys Cys Gly Thr Thr Asp Phe
                485                 490                 495

Glu Ser Ala Ser Ala Gly Gly Trp Glu Asp Ile Ser Val Gly Lys Leu
        500                 505                 510

Gln Trp Gln Trp Val Glu Ala Gln Lys Ser Lys Pro Ala Gly Asp
        515                 520                 525

Ala Asn Arg Asp Ala Pro Gly His Phe Leu Ser Leu Gln Lys Ala Trp
        530                 535                 540

Gly Gln Leu Arg Ser Glu Ala Arg Ala Leu Thr Pro Ala Leu Gly Pro
545                 550                 555                 560

Ser Gly Pro His Cys Glu Leu His Met Ala Tyr Tyr Phe Gln Ser His
                565                 570                 575

Pro Gln Gly Phe Leu Ala Leu Val Val Val Glu Asn Gly Phe Arg Glu
        580                 585                 590

Leu Leu Trp Gln Ala Pro Gly Gly Ser Gly Ser Trp Thr Glu Glu
        595                 600                 605

Lys Ile Ile Leu Gly Ala Arg Arg Pro Phe Gln Leu Glu Phe Val
610                 615                 620

Ser Leu Val Asp Leu Asp Gly Pro Gly Gln Gln Gly Ala Gly Val Asp
625                 630                 635                 640

Asn Val Thr Leu Arg Asp Cys Asn Pro Met Val Thr Thr Glu Ser Asp
                645                 650                 655

Gln Glu Leu Ser Cys Asn Phe Glu Arg Asp Ser Cys Ser Trp His Thr
        660                 665                 670

Gly His Leu Thr Asp Ala His Trp His Arg Ile Lys Ser His Gly Ser
        675                 680                 685

Gln Leu Asp His Thr Thr Gly Gln Gly Phe Phe Met Phe Leu Asp Pro
        690                 695                 700

Thr Asp Pro Pro Ala Arg Gly Gln Gly Ala Leu Leu Leu Thr Arg Pro
705                 710                 715                 720

Gln Val Pro Val Val Pro Lys Glu Cys Leu Ser Phe Trp Tyr Arg Leu
                725                 730                 735

Tyr Gly Pro Gln Ile Gly Thr Leu Cys Leu Ala Met Arg Arg Glu Arg
        740                 745                 750

Glu Glu Asp Ile Leu Leu Trp Ser Arg Ser Gly Thr His Gly Asn Arg
        755                 760                 765

Trp His Gln Ala Trp Val Thr Leu His His Gln Pro Glu Ala Ser Thr
        770                 775                 780

Lys Tyr Gln Leu Leu Phe Glu Gly Leu Arg Asn Gly Tyr His Gly Thr
785                 790                 795                 800

Met Ala Leu Asp Asp Ile Ala Val Arg Pro Gly Pro Cys Trp Ala Pro
                805                 810                 815

Lys Ser Cys Ser Phe Glu Asp Ser Asp Cys Gly Phe Ser Pro Gly Gly
        820                 825                 830

Trp Gly Leu Trp Thr His Gln Ser Asn Ala Ser Gly Leu Ala Ser Trp
```

```
            835                 840                 845
Gly Pro Trp Ile Asp His Thr Thr Gly Thr Ala Gln Gly His Tyr Met
850                 855                 860

Val Val Asp Thr Ser Pro Asn Val Leu Pro Lys Gly His Val Ala Ala
865                 870                 875                 880

Leu Thr Ser Glu Glu His Gln Pro Leu Ser Gln Pro Ala Cys Leu Thr
                    885                 890                 895

Phe Trp Tyr His Met Ser Val Pro Asn Pro Gly Thr Leu Arg Val His
                900                 905                 910

Val Glu Glu Ser Thr Arg Arg Gln Glu Leu Ser Ile Ser Ala His Gly
            915                 920                 925

Arg Ser Ala Trp Arg Leu Gly Ser Val Asn Val Gln Ala Glu Gln Ala
930                 935                 940

Trp Lys Val Val Phe Glu Ala Val Ala Ala Gly Val Glu Tyr Ser Tyr
945                 950                 955                 960

Met Ala Leu Asp Asp Ile Ser Leu Gln Asp Gly Pro Cys Pro Gln Pro
                965                 970                 975

Gly Ser Cys Asp Phe Glu Thr Gly Leu Cys Gly Trp Ser His Leu Pro
                980                 985                 990

Trp Pro Ser Leu Gly Gly Tyr Ser Trp Asp Trp Ser Ser Gly Ala Thr
            995                 1000                1005

Pro Ser Arg Tyr Pro Gln Pro Ser Val Asp His Thr Leu Gly Thr Glu
    1010                1015                1020

Ala Gly His Phe Ala Phe Phe Glu Thr Ser Val Leu Gly Pro Gly Gly
1025                1030                1035                1040

Gln Ala Ala Trp Leu Arg Ser Glu Pro Leu Pro Ala Thr Thr Val Ser
                1045                1050                1055

Cys Leu Arg Phe Trp Tyr Tyr Met Gly Phe Pro Glu His Phe Tyr Lys
                1060                1065                1070

Gly Glu Leu Arg Val Leu Leu Ser Ser Ala Arg Gly Gln Leu Ala Val
            1075                1080                1085

Trp Tyr Gln Gly Gly His Leu Arg Asp Gln Trp Leu Gln Val Gln Ile
    1090                1095                1100

Glu Leu Ser Asn Ser Glu Glu Phe Gln Ile Val Phe Glu Ala Thr Leu
1105                1110                1115                1120

Gly Gly Gln Pro Ala Leu Gly Pro Ile Ala Ile Asp Asp Val Gln Tyr
                1125                1130                1135

Leu Ala Gly Gln Gln Cys Lys Gln Pro Ser Pro Ser Gln Gly Glu Val
                1140                1145                1150

Ala Ala Pro Val Ser Val Pro Val Ala Val Gly Gly Ala Leu Leu Phe
                1155                1160                1165

Phe Met Phe Leu Val Leu Met Gly Leu Gly Gly Trp His Trp Leu Gln
                1170                1175                1180

Lys Gln His Cys Pro Gly Gln Arg Ser Thr Asp Ala Ala Ala Ser Gly
1185                1190                1195                1200

Phe Ala Asn Ile Leu Phe Asn Ala Asp His Val Thr Leu Pro Glu Ser
                1205                1210                1215

Ile Thr Ser Asn Pro Gln Ser Pro Pro Asp Leu Ala
            1220                1225

<210> SEQ ID NO 16
<211> LENGTH: 508
<212> TYPE: PRT
<213> ORGANISM: Mus musculus
```

<220> FEATURE:
<221> NAME/KEY: misc_feature
<222> LOCATION: (1)...(508)
<223> OTHER INFORMATION: AMYP_MOUSE (P00688)

<400> SEQUENCE: 16

```
Met Lys Phe Val Leu Leu Leu Ser Leu Ile Gly Phe Cys Trp Ala Gln
1               5                   10                  15

Tyr Asp Pro His Thr Ser Asp Gly Arg Thr Ala Ile Val His Leu Phe
            20                  25                  30

Glu Trp Arg Trp Val Asp Ile Ala Lys Glu Cys Glu Arg Tyr Leu Ala
        35                  40                  45

Pro Lys Gly Phe Gly Gly Val Gln Val Ser Pro Pro Asn Glu Asn Val
50                  55                  60

Val Val His Asn Pro Ser Arg Pro Trp Trp Glu Arg Tyr Gln Pro Ile
65                  70                  75                  80

Ser Tyr Lys Ile Cys Thr Arg Ser Gly Asn Glu Asp Glu Phe Arg Asp
                85                  90                  95

Met Val Thr Arg Cys Asn Asn Val Gly Val Arg Ile Tyr Val Asp Ala
            100                 105                 110

Val Ile Asn His Met Cys Gly Ala Gly Asn Pro Ala Gly Thr Ser Ser
        115                 120                 125

Thr Cys Gly Ser Tyr Leu Asn Pro Asn Asn Arg Glu Phe Pro Ala Val
130                 135                 140

Pro Tyr Ser Ala Trp Asp Phe Asn Asp Asn Lys Cys Asn Gly Glu Ile
145                 150                 155                 160

Asp Asn Tyr Asn Asp Ala Tyr Gln Val Arg Asn Cys Arg Leu Thr Gly
                165                 170                 175

Leu Leu Asp Leu Ala Leu Glu Lys Asp Tyr Val Arg Thr Lys Val Ala
            180                 185                 190

Asp Tyr Met Asn His Leu Ile Asp Ile Gly Val Ala Gly Phe Arg Leu
        195                 200                 205

Asp Ala Ala Lys His Met Trp Pro Arg Asp Ile Lys Ala Val Leu Asp
210                 215                 220

Lys Leu His Asn Leu Asn Thr Lys Trp Phe Ser Gln Gly Ser Arg Pro
225                 230                 235                 240

Phe Ile Phe Gln Glu Val Ile Asp Leu Gly Gly Glu Ala Ile Lys Gly
                245                 250                 255

Ser Glu Tyr Phe Gly Asn Gly Arg Val Thr Glu Phe Lys Tyr Gly Ala
            260                 265                 270

Lys Leu Gly Thr Val Ile Arg Lys Trp Asn Gly Glu Lys Met Ser Tyr
        275                 280                 285

Leu Lys Asn Trp Gly Glu Gly Trp Gly Leu Val Pro Ser Asp Arg Ala
290                 295                 300

Leu Val Phe Val Asp Asn His Asp Asn Gln Arg Gly His Gly Ala Gly
305                 310                 315                 320

Gly Ser Ser Ile Leu Thr Phe Trp Asp Ala Arg Met Tyr Lys Met Ala
                325                 330                 335

Val Gly Phe Met Leu Ala His Pro Tyr Gly Phe Thr Arg Val Met Ser
            340                 345                 350

Ser Tyr Arg Trp Asn Arg Asn Phe Gln Asn Gly Lys Asp Gln Asn Asp
        355                 360                 365

Trp Ile Gly Pro Pro Asn Asn Asn Gly Val Thr Lys Glu Val Thr Ile
370                 375                 380
```

```
Asn Ala Asp Thr Thr Cys Gly Asn Asp Trp Val Cys Glu His Arg Trp
385                 390                 395                 400

Arg Gln Ile Arg Asn Met Val Ala Phe Arg Asn Val Val Asn Gly Gln
            405                 410                 415

Pro Phe Ser Asn Trp Trp Asp Asn Asn Ser Asn Gln Val Ala Phe Ser
        420                 425                 430

Arg Gly Asn Arg Gly Phe Ile Val Phe Asn Asn Asp Trp Ala Leu
        435                 440                 445

Ser Ala Thr Leu Gln Thr Gly Leu Pro Ala Gly Thr Tyr Cys Asp Val
    450                 455                 460

Ile Ser Gly Asp Lys Val Asp Gly Asn Cys Thr Gly Leu Arg Val Asn
465                 470                 475                 480

Val Gly Ser Asp Gly Lys Ala His Phe Ser Ile Ser Asn Ser Ala Glu
            485                 490                 495

Asp Pro Phe Ile Ala Ile His Ala Asp Ser Lys Leu
        500                 505
```

<210> SEQ ID NO 17
<211> LENGTH: 121
<212> TYPE: PRT
<213> ORGANISM: Rattus norvegicus
<220> FEATURE:
<221> NAME/KEY: misc_feature
<222> LOCATION: (1)...(121)
<223> OTHER INFORMATION: ANFB_RAT (P13205)

<400> SEQUENCE: 17

```
Met Asp Leu Gln Lys Val Leu Pro Gln Met Ile Leu Leu Leu Leu Phe
1               5                   10                  15

Leu Asn Leu Ser Pro Leu Gly Gly His Ser His Pro Leu Gly Ser Pro
            20                  25                  30

Ser Gln Ser Pro Glu Gln Ser Thr Met Gln Lys Leu Leu Glu Leu Ile
        35                  40                  45

Arg Glu Lys Ser Glu Glu Met Ala Gln Arg Gln Leu Ser Lys Asp Gln
    50                  55                  60

Gly Pro Thr Lys Glu Leu Leu Lys Arg Val Leu Arg Ser Gln Asp Ser
65                  70                  75                  80

Ala Phe Arg Ile Gln Glu Arg Leu Arg Asn Ser Lys Met Ala His Ser
                85                  90                  95

Ser Ser Cys Phe Gly Gln Lys Ile Asp Arg Ile Gly Ala Val Ser Arg
            100                 105                 110

Leu Gly Cys Asp Gly Leu Arg Leu Phe
        115                 120
```

<210> SEQ ID NO 18
<211> LENGTH: 906
<212> TYPE: PRT
<213> ORGANISM: Pongo abelii
<220> FEATURE:
<221> NAME/KEY: misc_feature
<222> LOCATION: (1)...(906)
<223> OTHER INFORMATION: CADH2_PONAB (Q5R9X1)

<400> SEQUENCE: 18

```
Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
```

```
            35                  40                  45
Val His Glu Gly Gln Pro Leu Leu Asn Val Lys Phe Ser Asn Cys Asn
 50                  55                  60
Gly Lys Arg Lys Val Gln Tyr Glu Ser Ser Glu Pro Ala Asp Phe Lys
 65                  70                  75                  80
Val Asp Glu Asp Gly Met Val Tyr Ala Val Arg Ser Phe Pro Leu Ser
                     85                  90                  95
Ser Glu His Ala Lys Phe Leu Ile Tyr Ala Gln Glu Glu Thr Gln
                100                 105                 110
Glu Lys Trp Gln Val Ala Val Lys Leu Ser Leu Lys Pro Thr Leu Thr
            115                 120                 125
Glu Glu Ser Val Lys Glu Ser Ala Glu Val Glu Ile Val Phe Pro
        130                 135                 140
Arg Gln Phe Ser Lys His Ser Gly His Leu Gln Arg Gln Lys Arg Asp
145                 150                 155                 160
Trp Val Ile Pro Pro Ile Asn Leu Pro Glu Asn Ser Arg Gly Pro Phe
                165                 170                 175
Pro Gln Glu Leu Val Arg Ile Arg Ser Asp Arg Asp Lys Asn Leu Ser
                180                 185                 190
Leu Arg Tyr Ser Val Thr Gly Pro Gly Ala Asp Gln Pro Pro Thr Gly
            195                 200                 205
Ile Phe Ile Ile Asn Pro Ile Ser Gly Gln Leu Ser Val Thr Lys Pro
210                 215                 220
Leu Asp Arg Glu Gln Ile Ala Arg Phe His Leu Arg Ala His Ala Val
225                 230                 235                 240
Asp Ile Asn Gly Asn Gln Val Glu Asn Pro Ile Asp Ile Val Ile Asn
                245                 250                 255
Val Ile Asp Met Asn Asp Asn Arg Pro Glu Phe Leu His Gln Val Trp
            260                 265                 270
Asn Gly Thr Val Pro Glu Gly Ser Lys Pro Gly Thr Tyr Val Met Thr
            275                 280                 285
Val Thr Ala Ile Asp Ala Asp Asp Pro Asn Ala Leu Asn Gly Met Leu
        290                 295                 300
Arg Tyr Arg Ile Leu Ser Gln Ala Pro Ser Thr Pro Ser Pro Asn Met
305                 310                 315                 320
Phe Thr Ile Asn Asn Glu Thr Gly Asp Ile Ile Thr Val Ala Ala Gly
                325                 330                 335
Leu Asp Arg Glu Lys Val Gln Gln Tyr Thr Leu Ile Ile Gln Ala Thr
                340                 345                 350
Asp Met Glu Gly Asn Pro Thr Tyr Gly Leu Ser Asn Thr Ala Thr Ala
            355                 360                 365
Ile Ile Thr Val Thr Asp Val Asn Asp Asn Pro Pro Glu Phe Thr Ala
        370                 375                 380
Met Thr Phe Tyr Gly Glu Val Pro Glu Asn Arg Val Asp Val Ile Val
385                 390                 395                 400
Ala Asn Leu Thr Val Thr Asp Lys Asp Gln Pro His Thr Pro Ala Trp
                405                 410                 415
Asn Ala Val Tyr Arg Ile Ser Gly Gly Asp Pro Thr Gly Arg Phe Ala
            420                 425                 430
Ile Gln Thr Asp Pro Asn Ser Asn Asp Gly Leu Val Thr Val Val Lys
        435                 440                 445
Pro Ile Asp Phe Glu Thr Asn Arg Met Phe Val Leu Thr Val Ala Ala
    450                 455                 460
```

-continued

```
Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                    485                 490                 495

Phe Ala Pro Asn Pro Lys Ile Ile Arg Gln Glu Glu Gly Leu His Ala
                500                 505                 510

Gly Thr Met Leu Thr Thr Phe Thr Ala Gln Asp Pro Asp Arg Tyr Met
            515                 520                 525

Gln Gln Asn Ile Arg Tyr Thr Lys Leu Ser Asp Pro Ala Asn Trp Leu
        530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Gly Thr Gly Thr Leu Gln
                580                 585                 590

Ile Tyr Leu Leu Asp Ile Asn Asp Asn Ala Pro Gln Val Leu Pro Gln
            595                 600                 605

Glu Ala Glu Thr Cys Glu Thr Pro Asp Pro Asn Ser Ile Asn Ile Thr
        610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
                645                 650                 655

Leu Asn Gly Asp Phe Ala Gln Leu Asn Leu Lys Ile Lys Phe Leu Glu
                660                 665                 670

Ala Gly Ile Tyr Glu Val Pro Ile Ile Thr Asp Ser Gly Asn Pro
            675                 680                 685

Pro Lys Ser Asn Ile Ser Ile Leu Arg Val Lys Val Cys Gln Cys Asp
        690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Arg Asp Lys Glu
            740                 745                 750

Arg Gln Ala Lys Gln Leu Leu Ile Asp Pro Glu Asp Asp Val Arg Asp
        755                 760                 765

Asn Ile Leu Lys Tyr Asp Glu Glu Gly Gly Gly Glu Glu Asp Gln Asp
        770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
            820                 825                 830

Gly Asp Phe Ile Asn Glu Gly Leu Lys Ala Ala Asp Asn Asp Pro Thr
        835                 840                 845

Ala Pro Pro Tyr Asp Ser Leu Leu Val Phe Asp Tyr Glu Gly Ser Gly
        850                 855                 860

Ser Thr Ala Gly Ser Leu Ser Ser Leu Asn Ser Ser Ser Ser Gly Gly
865                 870                 875                 880
```

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
        900                 905

<210> SEQ ID NO 19
<211> LENGTH: 799
<212> TYPE: PRT
<213> ORGANISM: Rattus norvegicus
<220> FEATURE:
<221> NAME/KEY: misc_feature
<222> LOCATION: (1)...(799)
<223> OTHER INFORMATION: CADH8_RAT (O54800)

<400> SEQUENCE: 19

Met Pro Glu Arg Leu Ala Glu Thr Leu Leu Asp Leu Trp Thr Pro Leu
1               5                   10                  15

Ile Ile Leu Trp Ile Thr Leu Pro Ser Phe Val Tyr Met Ala Pro Met
            20                  25                  30

Asn Gln Ala His Val Leu Thr Thr Gly Ser Pro Leu Glu Leu Ser Arg
        35                  40                  45

Gln Ser Glu Glu Met Arg Ile Leu Asn Arg Ser Lys Arg Gly Trp Val
    50                  55                  60

Trp Asn Gln Met Phe Val Leu Glu Glu Phe Ser Gly Pro Glu Pro Ile
65                  70                  75                  80

Leu Val Gly Arg Leu His Thr Asp Leu Asp Pro Gly Ser Lys Lys Ile
                85                  90                  95

Lys Tyr Ile Leu Ser Gly Asp Gly Ala Gly Thr Ile Phe Gln Ile Asn
            100                 105                 110

Asp Ile Thr Gly Asp Ile His Ala Ile Lys Arg Leu Asp Arg Glu Glu
        115                 120                 125

Lys Ala Glu Tyr Thr Leu Thr Ala Gln Ala Val Asp Trp Glu Thr Asn
    130                 135                 140

Lys Pro Leu Glu Pro Pro Ser Glu Phe Ile Ile Lys Val Gln Asp Ile
145                 150                 155                 160

Asn Asp Asn Ala Pro Glu Phe Leu Asn Gly Pro Tyr His Ala Thr Val
                165                 170                 175

Pro Glu Met Ser Ile Leu Gly Thr Ser Val Thr Asn Val Thr Ala Thr
            180                 185                 190

Asp Ala Asp Asp Pro Val Tyr Gly Asn Ser Ala Lys Leu Val Tyr Ser
        195                 200                 205

Ile Leu Glu Gly Gln Pro Tyr Phe Ser Ile Glu Pro Glu Thr Ala Ile
    210                 215                 220

Ile Lys Thr Ala Leu Pro Asn Met Asp Arg Glu Ala Lys Glu Glu Tyr
225                 230                 235                 240

Leu Val Val Ile Gln Ala Lys Asp Met Gly Gly His Ser Gly Gly Leu
                245                 250                 255

Ser Gly Thr Thr Thr Leu Thr Val Thr Leu Thr Asp Val Asn Asp Asn
            260                 265                 270

Pro Pro Lys Phe Ala Gln Ser Leu Tyr His Phe Ser Val Pro Glu Asp
        275                 280                 285

Val Val Leu Gly Thr Ala Ile Gly Arg Val Lys Ala Asn Asp Gln Asp
    290                 295                 300

Ile Gly Glu Asn Ala Gln Ser Ser Tyr Asp Ile Ile Asp Gly Asp Gly
305                 310                 315                 320

Thr Ala Leu Phe Glu Ile Thr Ser Asp Ala Gln Ala Gln Asp Gly Val

```
                  325                 330                 335
Ile Arg Leu Arg Lys Pro Leu Asp Phe Glu Thr Lys Lys Ser Tyr Thr
                340                 345                 350
Leu Lys Val Glu Ala Ala Asn Ile His Ile Asp Pro Arg Phe Ser Gly
                355                 360                 365
Arg Gly Pro Phe Lys Asp Thr Ala Thr Val Lys Ile Val Val Glu Asp
            370                 375                 380
Ala Asp Glu Pro Pro Val Phe Ser Ser Pro Thr Tyr Leu Leu Glu Val
385                 390                 395                 400
His Glu Asn Ala Ala Leu Asn Ser Val Ile Gly Gln Val Thr Ala Arg
                405                 410                 415
Asp Pro Asp Ile Thr Ser Ser Pro Ile Arg Phe Ser Ile Asp Arg His
                420                 425                 430
Thr Asp Leu Glu Arg Gln Phe Asn Ile Asn Ala Asp Asp Gly Lys Ile
                435                 440                 445
Thr Leu Ala Thr Pro Leu Asp Arg Glu Leu Ser Val Trp His Asn Ile
                450                 455                 460
Ser Ile Ile Ala Thr Glu Ile Arg Asn His Ser Gln Ile Ser Arg Val
465                 470                 475                 480
Pro Val Ala Ile Lys Val Leu Asp Val Asn Asp Asn Ala Pro Glu Phe
                485                 490                 495
Ala Ser Glu Tyr Glu Ala Phe Leu Cys Glu Asn Gly Lys Pro Gly Gln
                500                 505                 510
Val Ile Gln Thr Val Ser Ala Met Asp Lys Asp Asp Pro Lys Asn Gly
                515                 520                 525
His Phe Phe Leu Tyr Ser Leu Leu Pro Glu Met Val Asn Asn Pro Asn
                530                 535                 540
Phe Thr Ile Lys Lys Asn Glu Asp Asn Ser Leu Ser Ile Leu Ala Lys
545                 550                 555                 560
His Asn Gly Phe Asn Arg Gln Lys Gln Glu Val Tyr Leu Leu Pro Ile
                565                 570                 575
Val Ile Ser Asp Ser Gly Asn Pro Pro Leu Ser Ser Thr Ser Thr Leu
                580                 585                 590
Thr Ile Arg Val Cys Gly Cys Ser Asn Asp Gly Val Val Gln Ser Cys
                595                 600                 605
Asn Val Glu Pro Tyr Val Leu Pro Ile Gly Leu Ser Met Gly Ala Leu
                610                 615                 620
Ile Ala Ile Leu Ala Cys Ile Ile Leu Leu Leu Val Ile Val Val Leu
625                 630                 635                 640
Phe Val Thr Leu Arg Arg His Lys Asn Glu Pro Leu Ile Ile Lys Asp
                645                 650                 655
Asp Glu Asp Val Arg Glu Asn Ile Ile Arg Tyr Asp Asp Glu Gly Gly
                660                 665                 670
Gly Glu Glu Asp Thr Glu Ala Phe Asp Ile Ala Thr Leu Gln Asn Pro
            675                 680                 685
Asp Gly Ile Asn Gly Phe Leu Pro Arg Lys Asp Ile Lys Pro Asp Leu
            690                 695                 700
Gln Phe Met Pro Arg Gln Gly Leu Ala Pro Val Pro Asn Gly Val Asp
705                 710                 715                 720
Val Asp Glu Phe Ile Asn Val Arg Leu His Glu Ala Asp Asn Asp Pro
                725                 730                 735
Thr Ala Pro Pro Tyr Asp Ser Ile Gln Ile Tyr Gly Tyr Glu Gly Arg
                740                 745                 750
```

```
Gly Ser Val Ala Gly Ser Leu Ser Leu Glu Ser Thr Thr Ser Asp
        755                 760                 765

Ser Asp Gln Asn Phe Asp Tyr Leu Ser Asp Trp Gly Pro Arg Phe Lys
770                 775                 780

Arg Leu Gly Glu Leu Tyr Ser Val Gly Glu Ser Asp Lys Glu Thr
785                 790                 795

<210> SEQ ID NO 20
<211> LENGTH: 97
<212> TYPE: PRT
<213> ORGANISM: Macaca mulatta
<220> FEATURE:
<221> NAME/KEY: misc_feature
<222> LOCATION: (1)...(97)
<223> OTHER INFORMATION: CCL11_MACMU (Q8MIT7)

<400> SEQUENCE: 20

Met Lys Val Ser Thr Thr Leu Leu Trp Leu Leu Val Ala Ala Ala
1               5                   10                  15

Phe Ser Pro Gln Gly Leu Thr Gly Pro Asp Ser Val Ala Thr Thr Cys
                20                  25                  30

Cys Phe Thr Leu Thr Asn Lys Lys Ile Pro Leu Gln Arg Leu Glu Ser
            35                  40                  45

Tyr Arg Arg Ile Ile Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Arg Lys Ser Pro Thr Pro Lys
                85                  90                  95

Pro

<210> SEQ ID NO 21
<211> LENGTH: 120
<212> TYPE: PRT
<213> ORGANISM: Macaca mulatta
<220> FEATURE:
<221> NAME/KEY: misc_feature
<222> LOCATION: (1)...(120)
<223> OTHER INFORMATION: CCL23_MACMU (Q8HYP4)

<400> SEQUENCE: 21

Met Lys Val Ser Val Ala Ala Leu Ser Cys Leu Met Leu Val Thr Ala
1               5                   10                  15

Leu Gly Ser Gln Ala Gln Val Thr Asn Asp Ala Glu Thr Gly Phe Met
                20                  25                  30

Met Ser Lys Leu Ser Leu Ala Asn Ser Glu Val Leu Asp Ser Phe His
            35                  40                  45

Ala Ile Asn Ala Asp Cys Cys Thr Ser Tyr Ile Pro Gly Ser Ile Pro
    50                  55                  60

Cys Ser Leu Leu Glu Ser Tyr Leu Glu Thr Ser Ser Cys Pro Lys
65                  70                  75                  80

Pro Gly Val Ile Phe Leu Thr Lys Asn Gly Arg Arg Leu Cys Val Ser
                85                  90                  95

Pro Ser Asn Lys Gln Val Leu Ala Cys Arg Ile Met Leu Lys Leu Ala
                100                 105                 110

Thr Arg Ile Lys Thr Arg Lys Asn
            115                 120
```

```
<210> SEQ ID NO 22
<211> LENGTH: 142
<212> TYPE: PRT
<213> ORGANISM: Homo sapiens
<220> FEATURE:
<221> NAME/KEY: misc_feature
<222> LOCATION: (1)...(142)
<223> OTHER INFORMATION: CYTD_HUMAN (P28325)

<400> SEQUENCE: 22

Met Met Trp Pro Met His Thr Pro Leu Leu Leu Thr Ala Leu Met
 1               5                  10                  15

Val Ala Val Ala Gly Ser Ala Ser Ala Gln Ser Arg Thr Leu Ala Gly
            20                  25                  30

Gly Ile His Ala Thr Asp Leu Asn Asp Lys Ser Val Gln Cys Ala Leu
            35                  40                  45

Asp Phe Ala Ile Ser Glu Tyr Asn Lys Val Ile Asn Lys Asp Glu Tyr
    50                  55                  60

Tyr Ser Arg Pro Leu Gln Val Met Ala Ala Tyr Gln Gln Ile Val Gly
65                  70                  75                  80

Gly Val Asn Tyr Tyr Phe Asn Val Lys Phe Gly Arg Thr Thr Cys Thr
                85                  90                  95

Lys Ser Gln Pro Asn Leu Asp Asn Cys Pro Phe Asn Asp Gln Pro Lys
            100                 105                 110

Leu Lys Glu Glu Glu Phe Cys Ser Phe Gln Ile Asn Glu Val Pro Trp
        115                 120                 125

Glu Asp Lys Ile Ser Ile Leu Asn Tyr Lys Cys Arg Lys Val
    130                 135                 140

<210> SEQ ID NO 23
<211> LENGTH: 1450
<212> TYPE: DNA
<213> ORGANISM: Artificial Sequence
<220> FEATURE:
<223> OTHER INFORMATION: synthetically constructed apyrase

<400> SEQUENCE: 23
tcgaaagctt ctagacaatt gccgccacca tgatgtcctt tgtctctctg ctcctggttg      60
gcatcctatt ccatgccacc caggccgagg tcctccctcc aggactgaag tatggtattg     120
tgctggatgc cgggtcttca gggacccgcg tctacgtgta tcaatggcca gcagaaaaag     180
agaataatac cggagtggtc agtcaaacct tcaaatgtag tgtgaaaggc tctggaatct     240
ccagctatgg aaataacccc caagatgtcc ccagagcctt tgaggagtgt atgcaaaaag     300
tcaaggggca ggttccatcc cacctccacg atccacccc cattcacctg ggagccacgg     360
ctgggatgcg cttgctgagg ttgcaaaacg aaacagcagc taatgaagtc cttgaaagca     420
tccaaagcta cttcaagtcc cagccctttg actttaggg tgctcaaatc atttctgggc     480
aagaagaagg ggtatatgga tggattacag ccaactattt aatgggaaat ttcctggaga     540
agaacctgtg gcacatgtgg gtgcacccgc atggagtgga accacgggt gccctggact     600 taggtggtgc ctccacccaa atatccttcg tggcaggaga agatggat ctgaacacca     660 gcgacatcat gcaggtgtcc ctgtatggct acgtatacac gctctacaca cacagcttcc     720
agtgctatgg ccggaatgag gctgagaaga gtttctggc aatgctcctg cagaattctc     780
ctaccaaaaa ccatctcacc aatccctgtt accctcggga ttatagcatc agcttccacc     840
tgggccatgt atttgatagc ctgtgcactg tggaccagag gccagaaagt tataaccca     900 atgatgtcat cactttttgaa ggaactgggg acccatctct gtgtaaggag aaggtggctt     960
```

```
ccatatttga cttcaaagct tgccatgatc aagaaacctg ttcttttgat ggggtttatc    1020
agccaaagat taaagggcca tttgtggctt ttgcaggatt ctactacaca gccagtgctt    1080
taaatctttc aggtagcttt tccctggaca ccttcaactc cagcacctgg aatttctgct    1140
cacagaattg gagtcagctc ccactgctgc tccccaaatt tgatgaggta tatgcccgct    1200
cttactgctt ctcagccaac tacatctacc acttgtttgt gaacggttac aaattcacag    1260
aggagacttg gccccaaata cactttgaaa agaagtggg gaatagcagc atagcctggt     1320
ctcttggcta catgctcagc ctgaccaacc agatcccagc tgaaagccct ctgatccgtc    1380
tgcccataga accacctgtc tgatgagatc tcgagttcga catcgataat caacctctgg    1440
attacaaaat                                                           1450

<210> SEQ ID NO 24
<211> LENGTH: 460
<212> TYPE: PRT
<213> ORGANISM: Artificial Sequence
<220> FEATURE:
<223> OTHER INFORMATION: synthetically constructed EN-apyrase

<400> SEQUENCE: 24

Met Met Ser Phe Val Ser Leu Leu Leu Val Gly Ile Leu Phe His Ala
1               5                   10                  15

Thr Gln Ala Glu Val Leu Pro Pro Gly Leu Lys Tyr Gly Ile Val Leu
            20                  25                  30

Asp Ala Gly Ser Ser Gly Thr Arg Val Tyr Val Tyr Gln Trp Pro Ala
        35                  40                  45

Glu Lys Glu Asn Asn Thr Gly Val Val Ser Gln Thr Phe Lys Cys Ser
    50                  55                  60

Val Lys Gly Ser Gly Ile Ser Ser Tyr Gly Asn Asn Pro Gln Asp Val
65                  70                  75                  80

Pro Arg Ala Phe Glu Glu Cys Met Gln Lys Val Lys Gly Gln Val Pro
                85                  90                  95

Ser His Leu His Gly Ser Thr Pro Ile His Leu Gly Ala Thr Ala Gly
            100                 105                 110

Met Arg Leu Leu Arg Leu Gln Asn Glu Thr Ala Ala Asn Glu Val Leu
        115                 120                 125

Glu Ser Ile Gln Ser Tyr Phe Lys Ser Gln Pro Phe Asp Phe Arg Gly
    130                 135                 140

Ala Gln Ile Ile Ser Gly Gln Glu Gly Val Tyr Gly Trp Ile Thr
145                 150                 155                 160

Ala Asn Tyr Leu Met Gly Asn Phe Leu Glu Lys Asn Leu Trp His Met
                165                 170                 175

Trp Val His Pro His Gly Val Glu Thr Thr Gly Ala Leu Asp Leu Gly
            180                 185                 190

Gly Ala Ser Thr Gln Ile Ser Phe Val Ala Gly Glu Lys Met Asp Leu
        195                 200                 205

Asn Thr Ser Asp Ile Met Gln Val Ser Leu Tyr Gly Tyr Val Tyr Thr
    210                 215                 220

Leu Tyr Thr His Ser Phe Gln Cys Tyr Gly Arg Asn Glu Ala Glu Lys
225                 230                 235                 240

Lys Phe Leu Ala Met Leu Leu Gln Asn Ser Pro Thr Lys Asn His Leu
                245                 250                 255

Thr Asn Pro Cys Tyr Pro Arg Asp Tyr Ser Ile Ser Phe Thr Met Gly
            260                 265                 270
```

```
His Val Phe Asp Ser Leu Cys Thr Val Asp Gln Arg Pro Glu Ser Tyr
    275                 280                 285

Asn Pro Asn Asp Val Ile Thr Phe Glu Gly Thr Gly Asp Pro Ser Leu
    290                 295                 300

Cys Lys Glu Lys Val Ala Ser Ile Phe Asp Phe Lys Ala Cys His Asp
305             310                 315                     320

Gln Glu Thr Cys Ser Phe Asp Gly Val Tyr Gln Pro Lys Ile Lys Gly
                325                 330                 335

Pro Phe Val Ala Phe Ala Gly Phe Tyr Tyr Thr Ala Ser Ala Leu Asn
                340                 345                 350

Leu Ser Gly Ser Phe Ser Leu Asp Thr Phe Asn Ser Ser Thr Trp Asn
            355                 360                 365

Phe Cys Ser Gln Asn Trp Ser Gln Leu Pro Leu Leu Leu Pro Lys Phe
            370                 375                 380

Asp Glu Val Tyr Ala Arg Ser Tyr Cys Phe Ser Ala Asn Tyr Ile Tyr
385                 390                 395                 400

His Leu Phe Val Asn Gly Tyr Lys Phe Thr Glu Glu Thr Trp Pro Gln
                405                 410                 415

Ile His Phe Glu Lys Glu Val Gly Asn Ser Ser Ile Ala Trp Ser Leu
                420                 425                 430

Gly Tyr Met Leu Ser Leu Thr Asn Gln Ile Pro Ala Glu Ser Pro Leu
            435                 440                 445

Ile Arg Leu Pro Ile Glu Pro Pro Val Thr Arg Met
450                 455                 460
```